(12) United States Patent
Pobezinsky et al.

(10) Patent No.: US 11,389,479 B2
(45) Date of Patent: Jul. 19, 2022

(54) T CELL DIFFERENTIATION AND FUNCTION REGULATION BY DECREASING LET7 EXPRESSION

(71) Applicant: University of Massachusetts, Boston, MA (US)

(72) Inventors: Leonid Pobezinsky, Leverett, MA (US); Elena Pobezinskaya, Leverett, MA (US)

(73) Assignee: University of Massachusetts, Boston, MA (US)

(*) Notice: Subject to any disclaimer, the term of this patent is extended or adjusted under 35 U.S.C. 154(b) by 575 days.

(21) Appl. No.: 16/097,467

(22) PCT Filed: May 2, 2017

(86) PCT No.: PCT/US2017/030657
§ 371 (c)(1),
(2) Date: Oct. 29, 2018

(87) PCT Pub. No.: WO2017/192601
PCT Pub. Date: Nov. 9, 2017

(65) Prior Publication Data
US 2019/0144857 A1 May 16, 2019

Related U.S. Application Data

(60) Provisional application No. 62/330,668, filed on May 2, 2016.

(51) Int. Cl.
| | |
|---|---|
| *A61K 35/17* | (2015.01) |
| *A61P 35/00* | (2006.01) |
| *A61P 31/00* | (2006.01) |
| *A61P 37/04* | (2006.01) |
| *A61K 45/06* | (2006.01) |
| *C12N 5/0783* | (2010.01) |
| *A61K 31/00* | (2006.01) |
| *C12N 5/00* | (2006.01) |
| *A61K 31/713* | (2006.01) |
| *C07K 14/47* | (2006.01) |
| *C12N 15/113* | (2010.01) |

(52) U.S. Cl.
CPC .............. *A61K 35/17* (2013.01); *A61K 31/00* (2013.01); *A61K 45/06* (2013.01); *A61P 35/00* (2018.01); *A61P 37/04* (2018.01); *C12N 5/0638* (2013.01); *A61K 31/713* (2013.01); *C07K 14/4703* (2013.01); *C12N 15/113* (2013.01); *C12N 2310/141* (2013.01); *C12N 2330/10* (2013.01)

(58) Field of Classification Search
CPC . C12N 5/0638; C12N 2310/141; A61K 35/17
See application file for complete search history.

(56) References Cited

U.S. PATENT DOCUMENTS

| | | |
|---|---|---|
| 2014/0328858 A1 | 11/2014 | Gregory et al. |
| 2014/0377263 A1 | 12/2014 | Lieberman et al. |
| 2015/0361431 A1 | 12/2015 | Brown et al. |

FOREIGN PATENT DOCUMENTS

WO  WO-2017192601 A1  11/2017

OTHER PUBLICATIONS

Wu et al, 2007 (PLoS One 2(10): e1020; pp. 1-11 as printed).*
"International Application Serial No. PCT/US2017/030657, International Search Report dated Aug. 17, 2017", 4 pgs.
"International Application Serial No. PCT/US2017/030657, Written Opinion dated Aug. 17, 2017", 4 pgs.
"Selected microRNAs define cell fate determination of murine central memory CD8 T cells", vol. 5 e1 1243, (Jun. 22, 2010), 10 pgs.
Beachy, et al., "Enforced expression of Lin28b leads to impaired T-cell development release of inflammatory cytokines and peripheral T-cell lymphoma", vol. 120, (Jun. 21, 2012), 13 pgs.
Pobezinsky, et al., "Let-7 microRNAs target the lineage-specific transcription factor PLZF to regulate terminal NKT cell differentiation and effector function", Nat Immunol vol. 16, (Jun. 4, 2015), 24 pgs.
Swaminathan, et al., "Differential regulation of the Let-7 family of microRNAs in CD4 T cells alters IL-b-10 expression", vol. 188, (May 14, 2012), 10 pgs.
Wells, et al., "Modulation of let-7 miRNAs controls the differentiatmon of effector CD8 T cells", vol. 6 e26398, (Jul. 24, 2014), 60 pgs.

* cited by examiner

*Primary Examiner* — Zachary C Howard
(74) *Attorney, Agent, or Firm* — Schwegman Lundberg & Woessner, P.A.

(57) ABSTRACT

Disclosed herein are compositions and methods for enhancing T-cell activity by modulating a miRNA so as to improve T-cell therapies, infectious disease therapies and downregulate auto-immune responses.

7 Claims, 34 Drawing Sheets

Specification includes a Sequence Listing.

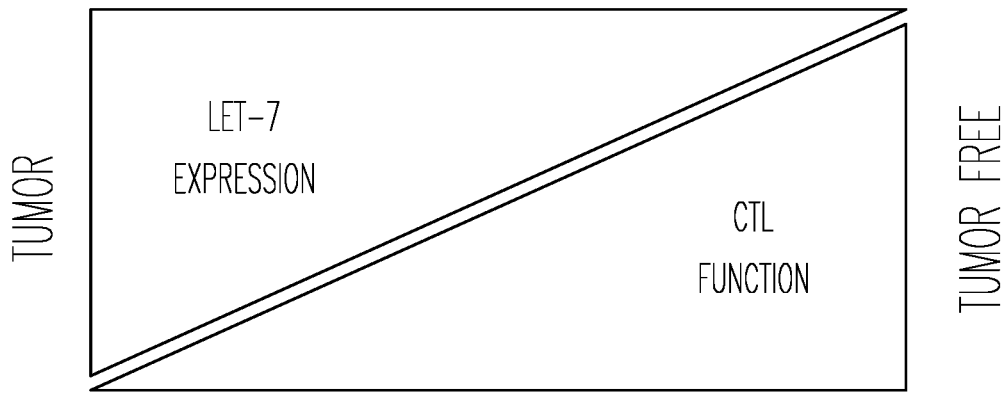
Fig. 1A
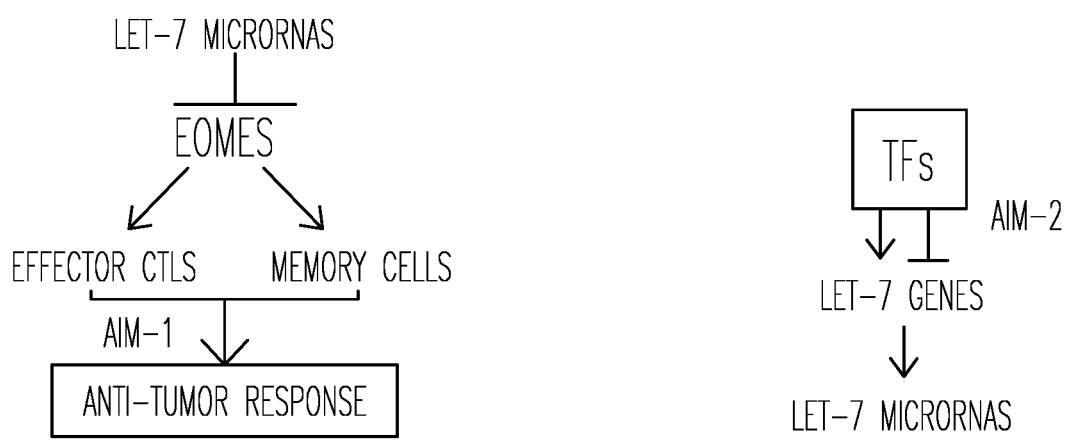
Fig. 1B
Fig. 1C

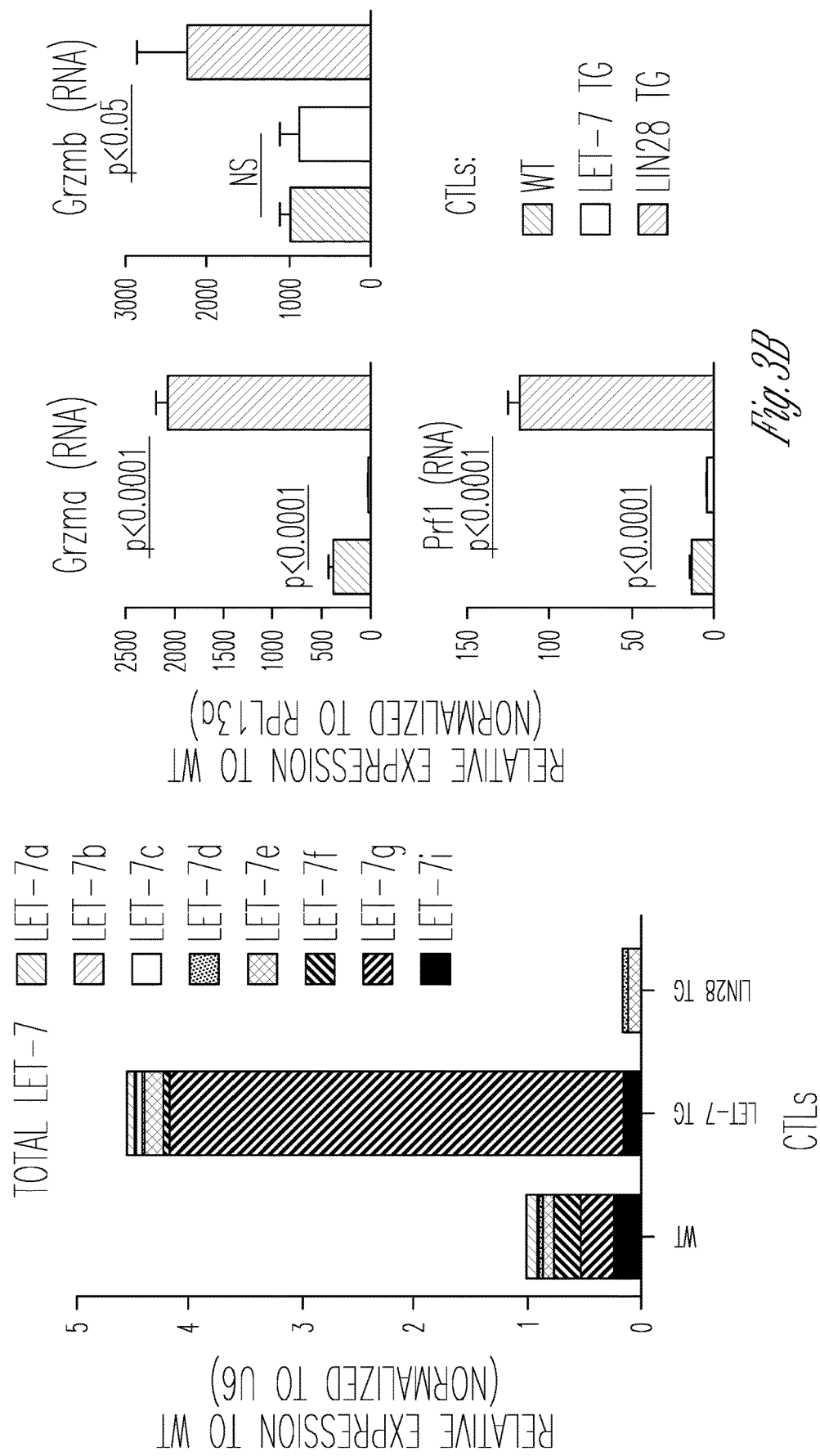

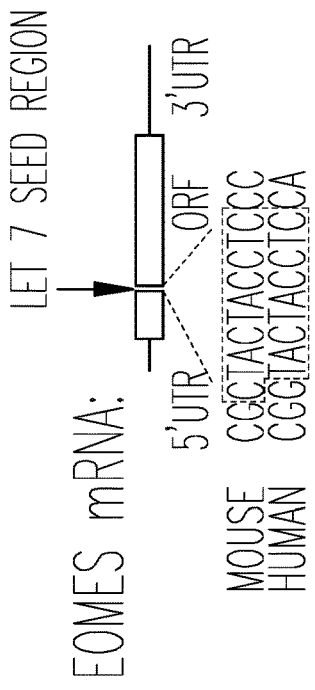
Fig. 4B
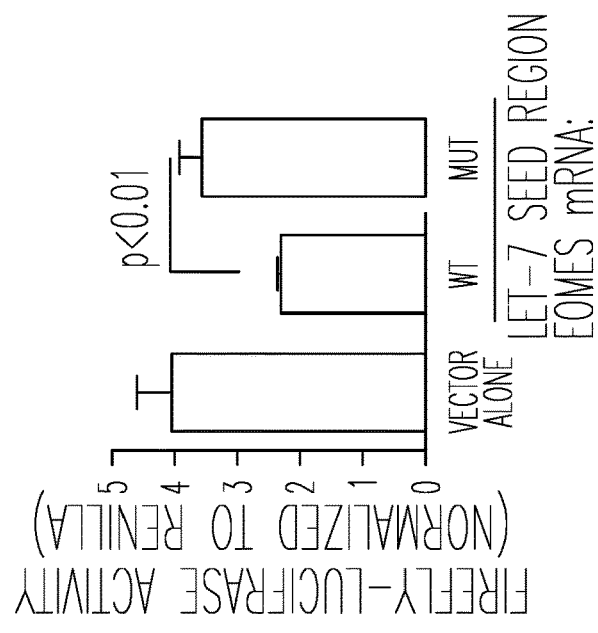
Fig. 4C
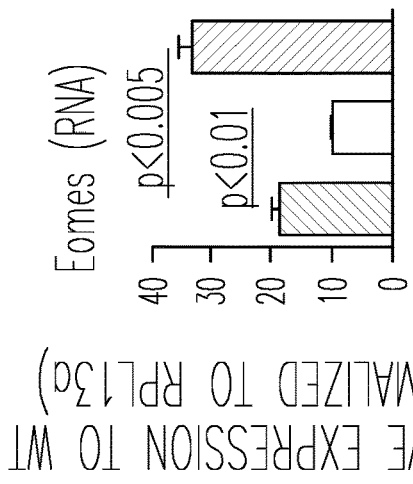
Fig. 4A
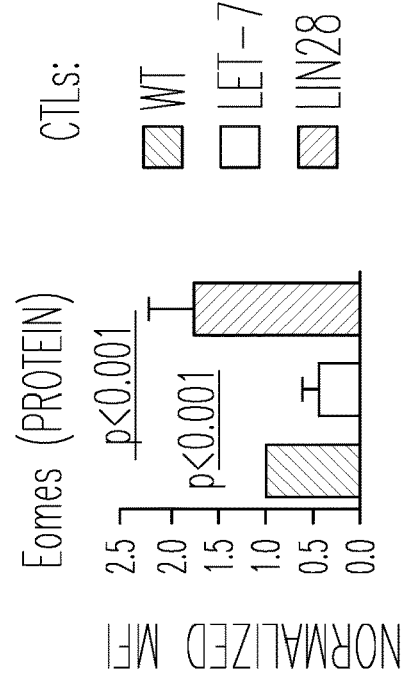

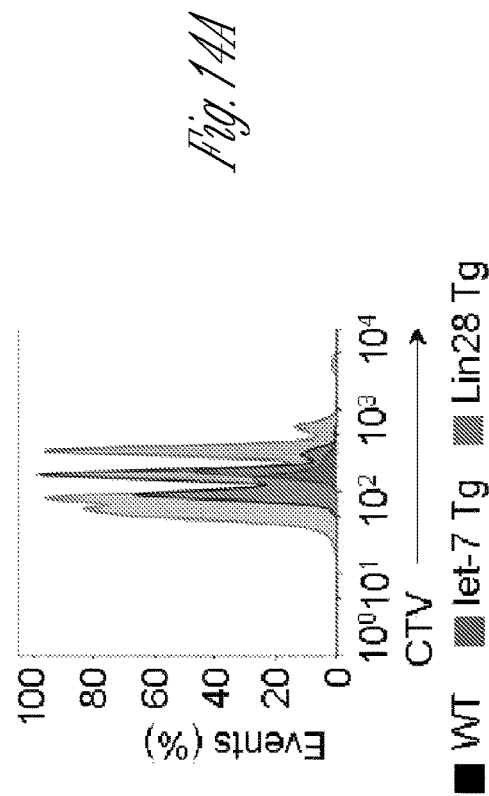
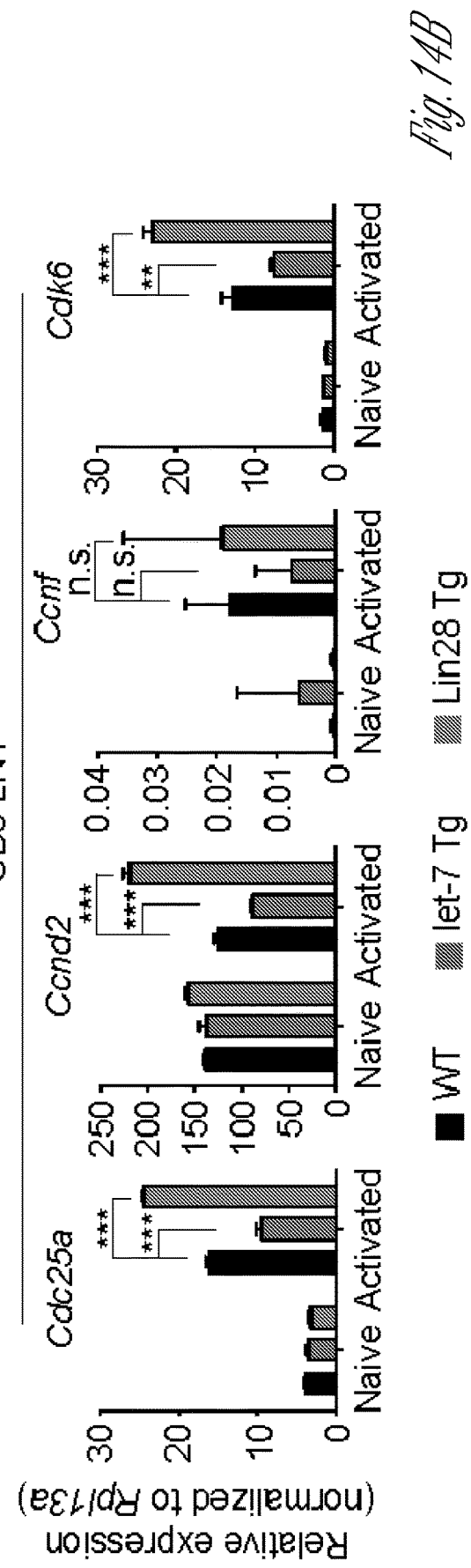
Fig. 14A
Fig. 14B

T CELL DIFFERENTIATION AND FUNCTION REGULATION BY DECREASING LET7 EXPRESSION

CROSS-REFERENCE TO RELATED APPLICATION

This application is a U.S. National Stage Filing under 35 U.S.C. 371 from International Application No. PCT/US2017/030657, filed on May 2, 2017, and published as WO 2017/192601, which claims the benefit of priority to U.S. Provisional Patent Application No. 62/330,668, filed on May 2, 2016. Both applications are incorporated herein by reference in their entireties.

BACKGROUND OF THE INVENTION

The immune system provides the only known intrinsic mechanism that eliminates malignant cells from an organism. Cytotoxic $CD8^+$ T Lymphocytes (CTLs), aided by T-helper cells, are the most potent killer-cells among all immuno-competent cell types involved in anti-tumor responses. Unfortunately, CTL-mediated immuno-surveillance is far from perfect. Malignant cells often escape the immune response by acquiring immunosuppressive properties or generating an immunosuppressive environment, making tumor-derived antigens less immunogenic than they might otherwise be.

SUMMARY OF THE INVENTION

Described herein is the discovery that miRNA (let7) regulates T cell responses (including both T-helpers and cytotoxic CD8+ Lymphocyte (CTLs)). Described herein are compositions and methods to increase the cytotoxic activity of CTLs and improve cancer immunotherapies. For example, reducing let7 expression in CTLs results in an increase in activation of these cells. Thus, let7 levels can be manipulated in vitro in adoptive cell therapies, such therapy can result in enhanced CTL anti-tumor responses when these cells are injected back into patients. Conversely, it is disclosed herein that when let7 expression levels are maintained or increased, CTLs are diminished in their ability to respond. Thus, delivery of let7 miRNA, or increasing its expression may serve to dampen the immune system in individuals with autoimmune disorders. As such, microRNA Let-7 is a master regulator of T cell differentiation and function.

One embodiment provides a composition comprising T cells with increased or decreased expression of let7 as compared to wild-type cells. Another embodiment provides a method to treat cancer comprising administering to a subject in need thereof an effective amount of T cells with decreased expression of let7 as compared to wild-type T cells. One embodiment provides a method to improve cancer therapy comprising administering to a subject in need thereof an effective amount of T cells with decreased expression of let7 as compared to wild-type T cells. Another method provides a method to treat or prevent an autoimmune disease comprising administering to a subject in need thereof an effective amount of T cells with increased expression of let7 as compared to wild-type T cells. One embodiment provides a method to increase cytotoxic activity of CTLs comprising decreasing the level of let7 expression in said CTL. In one embodiment, the let7 expression is increased or decreased by RNAi, shRNA, microRNA, knock out, mutation, increase in copy number of let7 or increase in expression by inserting a strong promoter in front of let7 coding region, in for example an expression vector or the cell genome itself.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A-C Let-7 microRNAs control CTL function.

FIGS. 3A-B Effect of let-7 expression on CTL differentiation: Expression of let-7 microRNAs in CTLs, 5 days of culture (A); mRNA expression of granzyme-A, B (Grzma, Grzmb) and perforin (Prf1) in CTLs, 5 days of culture (B).

FIGS. 4A-C Let-7 microRNAs inhibit expression of Eomes: mRNA and protein (mean fluorescence intensity-MFI) expression of eomes in CTLs, 5 days of culture (A); Eomes mRNA, including untranslated regions (UTRs) and open reading frame (ORF) with let-7 binding site (in red) in humans and mice (B) (SEQ ID NOs: 53 and 54); Luciferase reporter assay of targeting of the eomes ORF that contains wild type or mutant let-7 seed region by endogenous let-7 microRNAs in NIH-3T3 cells transfected with firefly-luciferase reporter (C).

FIGS. 7A-B FIG. 7. PD-1/PD-L1 expression. Surface expression (MFI) of PD-L1 on IFN-γ treated tumor cells (A). Surface expression (MFI) of PD-1 on in vitro generated CTLs (B).

FIGS. 14A-D let-7 miRNAs suppress the proliferation and metabolism of activated CD8 T cells (a) Analysis of the proliferation of CellTrace Violet-labeled naïve CD8 T cells from the indicated mice 72 hours after activation with anti-CD3. (b) Quantitative RT-PCR analysis of cell cycle regulators: Cdc25a (Cell division cycle 25A phosphatase), Ccnd2 (Cyclin D2), Ccnf (Cyclin F), Cdk6 (Cyclin dependent kinase 6) in naïve and activated wild type, let-7 Tg, and Lin28 Tg CD8 T cells 3 days after anti-CD3 stimulation, presented relative to the ribosomal protein Rpl13a. (c) Quantitative RT-PCR analysis of Myc and Tfap4 (Transcription factor AP-4) in CD8 T cells after stimulation with anti-CD3, presented relative to the ribosomal protein Rpl13a. Wild type, let-7 Tg, and Lin28 Tg CD8 T cells were stimulated with anti-CD3 and differentiated for the indicated time. (d) Quantitative RT-PCR analysis of the expression of genes involved in the metabolic switch: Glut1 (Glucose transporter 1), Glut3 (Glucose transporter 3), Gpd2 (Glycerol-3-phosphate dehydrogenase 2), Pfk1 (Phosphofructokinase 1), Hk2 (Hexokinase 2), Tpi (Triose phosphate isomerase), Pkm (Pyruvate kinase muscle isozyme), Ldha (Lactate dehydrogenase A), Yars (Tyrosyl-tRNA synthetase) in wild type, let-7 Tg, and Lin28 Tg CD8 T cells three days after stimulation with anti-CD3, presented relative to the ribosomal protein, Rpl13a. n.s., not significant ($P>0.05$), * $P<0.05$,  $P<0.01$, and * $P<0.001$, compared with wild type using two-tailed Student's t-test. (b, c, d; one experiment representative of three independent experiments (a) or mean and s.e.m. of technical triplicates (b,c,d)).

DETAILED DESCRIPTION OF THE INVENTION

Figure 2:
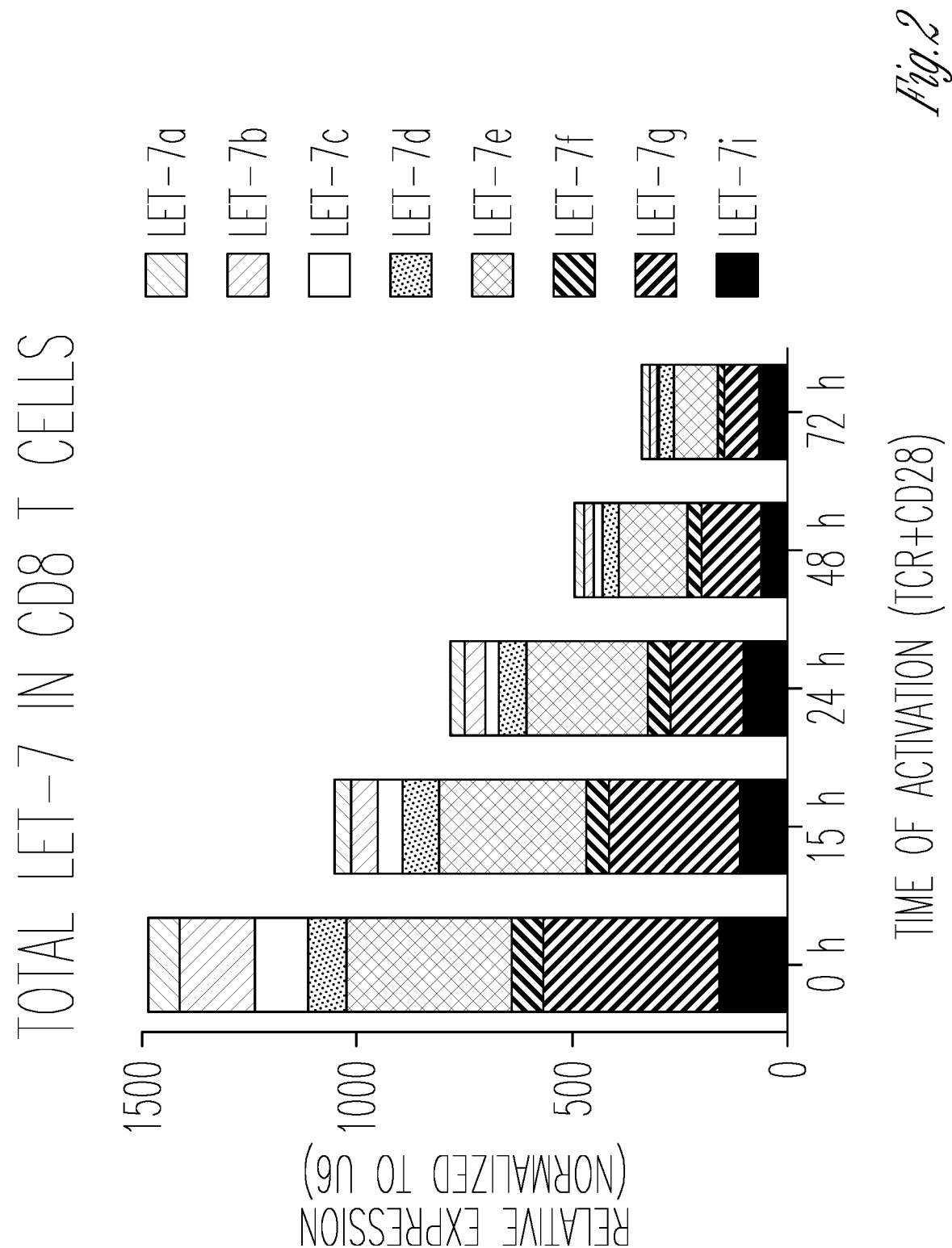
FIG. 2 Let-7 is down-regulated in activated T cells. Changes in let-7 microRNAs expression upon stimulation (anti-TCR and anti-CD28 mAbs) of naïve $CD8^+$ T cells over time.

Disclosed herein are compositions and methods for enhancing T-cell activity by modulating a miRNA so as improve T-cell therapies and down-regulate auto-immune responses. Further disclosed herein is the discovery of compositions and methods that can improve cancer immunotherapies; in particular those that are based on adoptive T cell transfer (e.g., compatible with new and existing methods for T-cell therapies). For example, the methods and compositions disclosed herein can improve T-Cell therapy and can dampen the immune response in autoimmune disorders.

For the purposes of clarity and a concise description, features can be described herein as part of the same or separate embodiments; however it will be appreciated that the scope of the invention may include embodiments having combinations of all or some of the features described.

The terminology used herein is for the purpose of describing particular embodiments only and is not intended to be limiting of the invention.

As used herein, the indefinite articles "a", "an" and "the" should be understood to include plural reference unless the context clearly indicates otherwise.

The phrase "and/or," as used herein, should be understood to mean "either or both" of the elements so conjoined, e.g., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, e.g., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

As used herein, the term "about" means plus or minus 10% of the indicated value. For example, about 100 means from 90 to 110.

As used herein, the term "subject" refers to any animal (e.g., mammals, birds, reptiles, amphibians, fish), including, but not limited to, humans, non-human primates, rodents, and the like, which is to be the recipient of a particular treatment. Typically, the terms "subject" and "patient" may be used interchangeably herein in reference to a subject.

As used herein, the term "administering" refers to providing a therapeutically effective amount of a chemical or biological compound or pharmaceutical composition to a subject. The chemical or biological compound of the present invention can be administered alone, but may be administered with other compounds, excipients, fillers, binders, carriers or other vehicles selected based upon the chosen route of administration and standard pharmaceutical practice. Administration may be by way of carriers or vehicles, such as injectable solutions, including sterile aqueous or non-aqueous solutions, or saline solutions; creams; lotions; capsules; tablets; granules; pellets; powders; suspensions, emulsions, or microemulsions; patches; micelles; liposomes; vesicles; implants, including microimplants; eye drops; ear drops; sprays, including nasal sprays; other proteins and peptides; synthetic polymers; microspheres; nanoparticles; and the like.

The chemical or biological compound or pharmaceutical composition of the present invention may also be included, or packaged, with other non-toxic compounds, such as pharmaceutically acceptable carriers, excipients, binders and fillers including, but not limited to, glucose, lactose, gum acacia, gelatin, mannitol, xanthan gum, locust bean gum, galactose, oligosaccharides and/or polysaccharides, starch paste, magnesium trisilicate, talc, corn starch, starch fragments, keratin, colloidal silica, potato starch, urea, dextrans, dextrins, and the like. Moreover, the packaging material may be biologically inert or lack bioactivity, such as plastic polymers, silicone, etc. and may be processed internally by the subject without affecting the effectiveness of the agent packaged and/or delivered therewith.

The term "effective amount," as applied to the compound(s), biologics and pharmaceutical compositions described herein, means the quantity necessary to render the desired therapeutic result. For example, an effective amount is a level effective to treat, cure, or alleviate the symptoms of a disorder for which the therapeutic compound, biologic or composition is being administered. Amounts effective for the particular therapeutic goal sought will depend upon a variety of factors including the disorder being treated and its severity and/or stage of development/progression; the bioavailability, and activity of the specific compound, biologic or pharmaceutical composition used; the route or method of administration and introduction site on the subject; the rate of clearance of the specific compound or biologic and other pharmacokinetic properties; the duration of treatment; inoculation regimen; drugs used in combination or coincident with the specific compound, biologic or composition; the age, body weight, sex, diet, physiology and general health of the subject being treated; and like factors well known to one of skill in the relevant scientific art. Some variation in dosage can occur depending upon the condition of the subject being treated, and the physician or other individual administering treatment will, in any event, determine the appropriate dose for an individual patient.

As used herein, "disorder" refers to a disorder, disease or condition, or other departure from healthy or normal biological activity, and the terms can be used interchangeably. The terms would refer to any condition that impairs normal function. The condition may be caused by sporadic or heritable genetic abnormalities. The condition may also be caused by non-genetic abnormalities. The condition may also be caused by injuries to a subject from environmental factors, such as, but not limited to, cutting, crushing, burning, piercing, stretching, shearing, injecting, or otherwise modifying a subject's cell(s), tissue(s), organ(s), system(s), or the like.

As used herein, "treatment" or "treating" refers to arresting or inhibiting, or attempting to arrest or inhibit, the development or progression of a disorder and/or causing, or attempting to cause, the reduction, suppression, regression, or remission of a disorder and/or a symptom thereof. As would be understood by those skilled in the art, various clinical and scientific methodologies and assays may be used to assess the development or progression of a disorder, and similarly, various clinical and scientific methodologies and assays may be used to assess the reduction, regression, or remission of a disorder or its symptoms. Additionally, treatment can be applied to a subject or to a cell culture.

microRNA

A micro RNA (abbreviated miRNA) is a small non-coding RNA molecule (containing about 22 nucleotides) found in plants, animals and some viruses, that functions in RNA silencing and post-transcriptional regulation of gene expression.

Encoded by eukaryotic nuclear DNA in plants and animals and by viral DNA in certain viruses whose genome is based on DNA, miRNAs function via base-pairing with complementary sequences within mRNA molecules. As a result, these mRNA molecules are silenced, by one or more of the following processes: cleavage of the mRNA strand into two pieces; destabilization of the mRNA through shortening of its poly(A) tail; and less efficient translation of the mRNA into proteins by ribosomes.

miRNAs resemble the small interfering RNAs (siRNAs) of the RNA interference (RNAi) pathway, except miRNAs derive from regions of RNA transcripts that fold back on themselves to form short hairpins, whereas siRNAs derive from longer regions of double-stranded RNA.

The first miRNA was discovered in the early 1990s. However, miRNAs were not recognized as a distinct class of biological regulators until the early 2000s. miRNA research revealed different sets of miRNAs expressed in different cell types and tissues and multiple roles for miRNAs in plant and animal development and in many other biological processes. Aberrant miRNA expression are implicated in disease states. MiRNA-based therapies are under investigation.

The mature miRNA is part of an active RNA-induced silencing complex (RISC) containing Dicer and many associated proteins. RISC is also known as a microRNA ribonucleoprotein complex (miRNP); RISC with incorporated miRNA is sometimes referred to as "miRISC."

Dicer processing of the pre-miRNA is thought to be coupled with unwinding of the duplex. Generally, only one strand is incorporated into the miRISC, selected on the basis of its thermodynamic instability and weaker base-pairing on the 5' end relative to the other strand. The position of the stem-loop may also influence strand choice. The other strand, called the passenger strand due to its lower levels in the steady state, is denoted with an asterisk (*) and is normally degraded. In some cases, both strands of the duplex are viable and become functional miRNA that target different mRNA populations.

Gene silencing may occur either via mRNA degradation or preventing mRNA from being translated. For example, miR16 contains a sequence complementary to the AU-rich element found in the 3'UTR of many unstable mRNAs, such as TNF alpha or GM-CSF. It has been demonstrated that given complete complementarity between the miRNA and target mRNA sequence, Ago2 can cleave the mRNA and lead to direct mRNA degradation. Absent complementarity, silencing is achieved by preventing translation. The relation of miRNA and its target mRNA(s) can be based on the simple negative regulation of a target mRNA, but it seems that a common scenario is the use of a "coherent feed-forward loop," "mutual negative feedback loop" (also termed double negative loop) and "positive feedback/feed-forward loop" Some miRNAs work as buffers of random gene expression changes arising due to stochastic events in transcription, translation and protein stability. Such regulation is typically achieved by the virtue of negative feedback loops or incoherent feed-forward loop uncoupling protein output from mRNA transcription.

miRNA let7

The Let-7 microRNA precursor was identified from a study of developmental timing in *C. elegans*, (Rougvie, A E (2001) Nature Reviews Genetics 2 (9): 690-701) and was later shown to be part of a much larger class of non-coding RNAs termed microRNAs (Ambros, V (2001) Cell 107 (7): 823-826). miR-98 microRNA precursor from human is a let-7 family member. Let-7 miRNAs have now been predicted or experimentally confirmed in a wide range of species (MIPF0000002). miRNAs are initially transcribed in long transcripts (up to several hundred nucleotides) called primary miRNAs (pri-miRNAs), which are processed in the nucleus by Drosha and Pasha to hairpin structures of about ~70 nucleotide. These precursors (pre-miRNAs) are exported to the cytoplasm by exportin5, where they are subsequently processed by the enzyme Dicer to a ~22 nucleotide mature miRNA. The involvement of Dicer in miRNA processing demonstrates a relationship with the phenomenon of RNA interference.

In the human genome, the cluster let-7a-1/let-7f-1/let-7d is inside the region B at 9q22.3, with the defining marker D9S280-D9S 1809. One minimal LOH (loss of heterozygosity) region, between loci D11S1345-D11S1316, contains the cluster miR-125b1/let-7a-2/miR-100. The cluster miR-99a/let-7c/miR-125b-2 is in a 21p 11.1 region of HD (homozygous deletions). The cluster let-7g/miR-135-1 is in region 3 at 3p21.1-p21.2 (Calin et al. (2003) PNAS 101 (9): 2999-3004).

The sequences, expression timing, as well as genomic clustering of the vertebrate miRNAs members are all conserved across species (Rodriguez A.; et al. (2004) Genome Res. 14 (10A): 1902-1910.) The direct role of let-7 family in vertebrate development has not been clearly shown as in less complex organisms, yet the expression pattern of let-7 family is indeed temporal during developmental processes (Kloosterman W. P. and Plasterk R. H. (2006) Dev. Cell 11 (4): 441-450). Let-7 sequences (both human and mouse) and accession ## are provided below (modifications of these sequences are included as part of the invention, including use of non-natural nucleotides and those sequences which are at least about 95% identical):

```
>hsa-let-7a-5p MIMAT0000062
                                (SEQ ID NO: 1)
UGAGGUAGUAGGUUGUAUAGUU >hsa-let-7b-5p MIMAT0000063
                                (SEQ ID NO: 2)
UGAGGUAGUAGGUUGUGUGGUU >hsa-let-7c-5p MIMAT0000064
                                (SEQ ID NO: 3)
UGAGGUAGUAGGUUGUAUGGUU >hsa-let-7d-5p MIMAT0000065
                                (SEQ ID NO: 4)
AGAGGUAGUAGGUUGCAUAGUU >hsa-let-7e-5p MIMAT0000066
                                (SEQ ID NO: 5)
UGAGGUAGGAGGUUGUAUAGUU >hsa-let-7f-5p MIMAT0000067
                                (SEQ ID NO: 6)
UGAGGUAGUAGAUUGUAUAGUU >hsa-let-7g-5p MIMAT0000414
                                (SEQ ID NO: 7)
UGAGGUAGUAGUUUGUACAGUU >hsa-let-7i-5p MIMAT0000415
                                (SEQ ID NO: 8)
UGAGGUAGUAGUUUGUGCUGUU >hsa-miR-98-5p MIMAT0000096
                                (SEQ ID NO: 9)
UGAGGUAGUAAGUUGUAUUGUU >mmu-let-7a-5p MIMAT0000521
                                (SEQ ID NO: 10)
UGAGGUAGUAGGUUGUAUAGUU >mmu-let-7b-5p MIMAT0000522
                                (SEQ ID NO: 11)
UGAGGUAGUAGGUUGUGUGGUU >mmu-let-7c-5p MIMAT0000523
                                (SEQ ID NO: 12)
UGAGGUAGUAGGUUGUAUGGUU >mmu-let-7d-5p MIMAT0000383
                                (SEQ ID NO: 13)
AGAGGUAGUAGGUUGCAUAGUU >mmu-let-7e-5p MIMAT0000524
                                (SEQ ID NO: 14)
UGAGGUAGGAGGUUGUAUAGUU >mmu-let-7f-5p MIMAT0000525
                                (SEQ ID NO: 15)
UGAGGUAGUAGAUUGUAUAGUU >mmu-let-7g-5p MIMAT0000121
                                (SEQ ID NO: 16)
UGAGGUAGUAGUUUGUACAGUU >mmu-let-7i-5p MIMAT0000122
                                (SEQ ID NO: 17)
UGAGGUAGUAGUUUGUGCUGUU >mmu-miR-98-5p MIMAT0000545
                                (SEQ ID NO: 18)
UGAGGUAGUAAGUUGUAUUGUU
```

Modulate Expression of Let7

Let7 expression can be modulated via various techniques available to an art worker. For example, it can be knocked down (through mutation for example) or knocked out/deleted. Further, silencing RNA, such as miRNA, shRNA, RNAi etc. can be used to decrease expression of the let7. Further inhibitory proteins can be used to downregulate the expression and/or activity of let7 (e.g., Lin-28). To increase its expression, vector expressing let7 can be introduced into a cell (transient or stable transfection/transduction), such as a T cell, or a strong promoter can be inserted in front the let7 coding sequence. Methods are further discussed herein below.

Also, LIN28 expression is reciprocal to that of mature let-7 (Viswanathan S. R. et al. (2008) Science 320 (5872): 97-100). LIN28 selectively binds the primary and precursor forms of let-7, and inhibits the processing of pri-let-7 to form the hairpin precursor (Newman M. A. et al. (2008) RNA 14: 1539-49). This binding is facilitated by the conserved loop sequence of primary let-7 family members and RNA-binding domains of LIN28 proteins (Piskounova E. et al. (2008). J. Biol. Chem. 283: 21310-21314). Thus, alteration of the expression of LIN28, such as through knock down (through mutation for example) or knock out/deleted methods can be used to modulate the expression of let7. Also, an antibody can be used to bind to LIN28 and decrease/inhibit its activity. To increase its expression, a vector expressing LIN28 can be introduced into a cell (transient or stable transfection/transduction), such as a T cell, or a strong promoter can be inserted in front the LIN28 coding sequence. Methods are further discussed herein below.

Also, expression of let-7 members can be controlled by MYC binding to their promoters. Therefore, let-7 expression can be modulated by modulating MYC expression.

As used herein, "inhibit" refers to a reduction (e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100%) in the activity of let 7 as compared to the activity of let7 in the absence of an expression modifier.

Cancer/Autoimmune/Infectious Disorders/Diseases

Just as miRNA is involved in the normal functioning of eukaryotic cells, dysregulation of miRNA is associated with disease. The first human disease known to be associated with miRNA deregulation was chronic lymphocytic leukemia.

One embodiment provided herein is a method to treat cancer, autoimmune or infectious disorders/diseases, by administering to a subject in need thereof a composition that modulates the expression of let7, or cells that have been altered to have let expression modulated.

Cancer

Cancer is a group of diseases involving abnormal cell growth with the potential to invade or spread to other parts of the body. Not all tumors are cancerous; benign tumors do not spread to other parts of the body. Possible signs and symptoms include a lump, abnormal bleeding, prolonged cough, unexplained weight loss and a change in bowel movements. Over 100 cancers affect humans.

A number of cancers are recognized, including but not limited to, Bladder cancer, Lung cancer, Brain cancer, Melanoma, Breast cancer, Non-Hodgkin lymphoma, Cervical cancer, Ovarian cancer, Adrenal Cancer, Anal Cancer, Bile Duct Cancer, Bladder Cancer, Bone Cancer, Brain/CNS Tumors In Adults, Brain/CNS Tumors In Children, Breast Cancer, Breast Cancer In Men, Cancer in Adolescents, Cancer in Children, Cancer in Young Adults, Cancer of Unknown Primary, Castleman Disease, Cervical Cancer, Colon/Rectum Cancer, Endometrial Cancer, Esophagus Cancer, Ewing Family Of Tumors, Eye Cancer, Gallbladder Cancer, Gastrointestinal Carcinoid Tumors, Gastrointestinal Stromal Tumor (GIST), Gestational Trophoblastic Disease, Hodgkin Disease, Kaposi Sarcoma, Kidney Cancer, Laryngeal and Hypopharyngeal Cancer, Leukemia, Leukemia—Acute Lymphocytic (ALL) in Adults, Leukemia—Acute Myeloid (AML), Leukemia—Chronic Lymphocytic (CLL), Leukemia—Chronic Myeloid (CML), Leukemia—Chronic Myelomonocytic (CMML), Leukemia in Children, Liver Cancer, Lung Cancer, Lung Cancer—Non-Small Cell, Lung Cancer—Small Cell, Lung Carcinoid Tumor, Lymphoma, Lymphoma of the Skin, Malignant Mesothelioma, Multiple Myeloma, Myelodysplastic Syndrome, Nasal Cavity and Paranasal Sinus Cancer, Nasopharyngeal Cancer, Neuroblastoma, Non-Hodgkin Lymphoma, Non-Hodgkin Lymphoma In Children, Oral Cavity and Oropharyngeal Cancer, Osteosarcoma, Ovarian Cancer, Pancreatic Cancer, Penile Cancer, Pituitary Tumors, Prostate Cancer, Retinoblastoma, Rhabdomyosarcoma, Salivary Gland Cancer, Sarcoma—Adult Soft Tissue Cancer, Skin Cancer, Skin Cancer—Basal and Squamous Cell, Skin Cancer—Melanoma, Skin Cancer—Merkel Cell, Small Intestine Cancer, Stomach Cancer, Testicular Cancer, Thymus Cancer, Thyroid Cancer, Uterine Sarcoma, Vaginal Cancer, Vulvar Cancer, Waldenstrom Macroglobulinemia, and Wilms Tumor.

Autoimmune Disease

Autoimmune diseases arise from an abnormal immune response of the body against substances and tissues normally present in the body (autoimmunity). This may be restricted to certain organs (e.g. in autoimmune thyroiditis) or involve a particular tissue in different places (e.g. Goodpasture's disease which may affect the basement membrane in both the lung and the kidney). The treatment of autoimmune diseases is typically with immunosuppression-medication that decreases the immune response.

A number of autoimmune diseases are recognized, including but not limited to: Acute disseminated encephalomyelitis (ADEM); Addison's disease; Agammaglobulinemia; Alopecia areata; Amyotrophic lateral sclerosis (Lou Gehrig's disease; Motor Neuron Disease); Ankylosing Spondylitis; Antiphospholipid syndrome; Antisynthetase syndrome; Atopic allergy I; Atopic dermatitis I; Autoimmune aplastic anemia; Autoimmune cardiomyopathy; Autoimmune enteropathy; Autoimmune hemolytic anemia; Autoimmune hepatitis; Autoimmune inner ear disease; Autoimmune lymphoproliferative syndrome;Autoimmune pancreatitis; Autoimmune peripheral neuropathy; Autoimmune polyendocrine syndrome; Autoimmune progesterone dermatitis; Autoimmune thrombocytopenic purpura; Autoimmune urticaria; Autoimmune uveitis; Balo disease/Balo concentric sclerosis; Behcet's disease; Berger's disease; Bickerstaffs encephalitis; Blau syndrome; Bullous pemphigoid; Cancer; Castleman's disease; Celiac disease; Chagas disease; Chronic inflammatory demyelinating polyneuropathy; Chronic obstructive pulmonary disease; Chronic recurrent multifocal osteomyelitis; Churg-Strauss syndrome Cicatricial pemphigoid; Cogan syndrome; Cold agglutinin disease; Complement component 2 deficiency; Contact dermatitis; Cranial arteritis; CREST; Crohn's disease; Cushing's Syndrome; Cutaneous leukocytoclastic angiitis; Dego's disease; Dercum's disease; Dermatitis herpetiformis; Dermatomyositis; Diabetes mellitus type 1; Diffuse cutaneous systemic sclerosis; Discoid lupus erythematosus; Dressler's; Drug-induced lupus; Eczema; Endometriosis; Enthesitis-related arthritis; Eosinophilic fasciitis; Eosinophilic gastroenteritis; Eosinophilic pneumonia; Epidermolysis bullosa acquisita; Erythema nodosum; Erythroblastosis fetalis; Essential mixed cryoglobulinemia; Evan's syndrome; Fibrodysplasia ossificans progressive; Fibrosing alveolitis (or Idiopathic pulmonary fibrosis); Gastrointestinal pemphigoid; Glomerulonephritis; Goodpasture's syndrome; granulomatosis with polyangiitis; Graves' disease; Guillain-Barré syndrome (GBS); Hashimoto's encephalopathy; Hashimoto's thyroiditis; Henoch-Schonlein purpura; Herpes gestationis; Hidradenitis suppurativa; Hughes-Stovin syndrome; Hypogammaglobulinemia; Idiopathic inflammatory demyelinating diseases (a variant of multiple sclerosis); Idiopathic pulmonary fibrosis; Idiopathic thrombocytopenic purpura; Inclusion body myositis; Chronic inflammatory demyelinating polyneuropathy; Interstitial cystitis; Juvenile idiopathic arthritis; Kawasaki's disease; Lambert-Eaton myasthenic syndrome; Leukocytoclastic vasculitis; Lichen planus; Lichen sclerosus; Linear IgA disease (LAD); Lupoid hepatitis; Lupus erythematosus; Majeed syndrome; Meniere's disease; Miller-Fisher syndrome; Mixed connective tissue disease; Morphea; Mucha-Habermann disease; Multiple sclerosis; Myasthenia gravis; Microscopic colitis; Myositis; Narcolepsy; Neuromyelitis optica; Neuromyotonia; Occular cicatricial pemphigoid; Opsoclonus myoclonus syndrome; Ord's thyroiditis; Palindromic rheumatism; PANDAS (pediatric autoimmune neuropsychiatric disorders associated with *streptococcus*); Paraneoplastic cerebellar degeneration; Paroxysmal nocturnal hemoglobinuria (PNH); Parry Romberg syndrome; Parsonage-Turner syndrome; Pars planitis; Pemphigus vulgaris; Pernicious anaemia; Perivenous encephalomyelitis; POEMS syndrome; Polyarteritis *nodosa*; Polymyalgia rheumatic; Polymyositis; Primary biliary cirrhosis; Primary sclerosing cholangitis; Progressive inflammatory neuropathy; Psoriasis; Psoriatic arthritis; Pyoderma gangrenosum; Pure red cell aplasia; Rasmussen's encephalitis; Raynaud phenomenon; Relapsing polychondritis; Reiter's syndrome; Rheumatic fever; Sarcoidosis; Schizophrenia; Schmidt syndrome; Schnitzler syndrome; Scleritis; Scleroderma; Serum Sickness; Sjögren's syndrome; Spondyloarthropathy; Still's disease; Stiff person syndrome; Subacute bacterial endocarditis; Susac's syndrome; Sweet's syndrome; Sydenham chorea; Sympathetic ophthalmia; Systemic lupus erythematosus; Takayasu's arteritis; Temporal arteritis; Thrombocytopenia; Tolosa-Hunt syndrome; Transverse myelitis; Ulcerative colitis; Undifferentiated connective tissue disease; Undifferentiated spondyloarthropathy; Urticarial vasculitis; Vasculitis; and Vitiligo.

Infectious Disease

Infection is the invasion of an organism's body tissues by disease-causing agents, their multiplication, and the reaction of host tissues to these organisms and the toxins they produce. Infectious disease, also known as transmissible disease or communicable disease, is illness resulting from an infection.

Infections are caused by infectious agents including viruses, viroids, prions, bacteria, nematodes, such as parasitic roundworms and pinworms, arthropods such as ticks, mites, fleas, and lice, fungi such as ringworm, and other macroparasites such as tapeworms and other helminths.

Hosts can fight infections using their immune system. Mammalian hosts react to infections with an innate response, often involving inflammation, followed by an adaptive response.

Treating Cancer, Autoimmune or Infections Disease/Disorder

Disclosed herein are methods of treating cancer or an autoimmune disease or symptom thereof in a subject need thereof.

Adoptive Cell Transfer

Adoptive cell transfer (ACT) is the transfer of cells into a patient. The cells may have originated from the patient him- or herself and then been altered before being transferred back, or, they may have come from another individual. The cells are most commonly derived from the immune system, with the goal of transferring improved immune functionality and characteristics along with the cells back to the patient. For example, T cells can be isolated, or differentiated from less mature cells, their let7 expression can be modulated and then the T cells/cells with modulated let7 expression can be placed in the patient.

Genetically Modified Cells and Methods for Genetically Modifying Cells

T cells can be isolated, or differentiated from less mature cells. They can then be genetically modified ex vivo. For example, a subject's T cells are isolated. The cells are then genetically altered to increase or decrease let7 expression. The cells can then be screened or selected ex vivo to identify those cells which have been successfully altered, and these cells can be introduced into the subject, either locally or systemically. The cells can then provide a stably-transfected source of cells that can express the desired level of let7. Especially where the patient's own cells are the source of the cells, this method provides an immunologically safe method for producing cells for transplant.

Cells isolated by the methods described herein can be genetically modified by introducing DNA or RNA into the cell by a variety of methods available to those of skill in the art. These methods are generally grouped into four major categories: (1) viral transfer, including the use of DNA or RNA viral vectors, such as retroviruses, including lentiviruses (Mochizuki, H., et al., 1998; Martin, F., et al. 1999; Robbins, et al. 1997; Salmons, B. and Gunzburg, W. H., 1993; Sutton, R., et al., 1998; Kafri, T., et al., 1999; Dull, T., et al., 1998), Simian virus 40 (SV40), adenovirus (see, for example, Davidson, B. L., et al., 1993; Wagner, E., et al., 1992; Wold, W., *Adenovirus Methods and Protocols*, Humana Methods in Molecular Medicine (1998), Blackwell Science, Ltd.; Molin, M., et al., 1998; Douglas, J., et al., 1999; Hofmann, C., et al., 1999; Schwarzenberger, P., et al., 1997), alpha virus, including Sindbis virus (U.S. Pat. No. 5,843,723; Xiong, C., et al., 1989; Bredenbeek, P. J., et al., 1993; Frolov, I., et al., 1996), herpes virus (Laquerre, S., et al., 1998) and bovine papillomavirus, for example; (2) chemical transfer, including calcium phosphate transfection and DEAE dextran transfection methods; (3) membrane fusion transfer, using DNA-loaded membranous vesicles such as liposomes (Loeffler, J. and Behr, J., 1993), red blood cell ghosts and protoplasts, for example; and (4) physical transfer techniques, such as microinjection, microprojectile J. Wolff in "Gene Therapeutics" (1994) at page 195. (see J. Wolff in "Gene Therapeutics" (1994) at page 195; Johnston, S. A., et al., 1993; Williams, R. S., et al., 1991; Yang, N. S., et al., 1990), electroporation, nucleofection or direct "naked" DNA transfer.

Cells can be genetically altered by insertion of preselected isolated DNA, by substitution of a segment of the cellular genome with pre-selected isolated DNA, or by deletion of or inactivation of at least a portion of the cellular genome of the cell. Deletion or inactivation of at least a portion of the cellular genome can be accomplished by a variety of means, including but not limited to genetic recombination, by antisense technology (which can include the use of peptide nucleic acids or PNAs), or by ribozyme technology, for example. Insertion of one or more preselected DNA sequences can be accomplished by homologous recombination or by viral integration into the host cell genome. Methods of non-homologous recombination are also known, for example, as described in U.S. Pat. Nos. 6,623,958, 6,602,686, 6,541,221, 6,524,824, 6,524,818, 6,410,266, 6,361,972, the contents of which are specifically incorporated by reference for their entire disclosure relating to methods of non-homologous recombination.

The desired gene sequence can also be incorporated into the cell, particularly into its nucleus, using a plasmid expression vector and a nuclear localization sequence. Methods for directing polynucleotides to the nucleus have been described in the art. For example, signal peptides can be attached to plasmid DNA, as described by Sebestyen, et al. (1998), to direct the DNA to the nucleus for more efficient expression.

The genetic material can be introduced using promoters that will allow for the gene of interest to be positively or negatively induced using certain chemicals/drugs, to be eliminated following administration of a given drug/chemical, or can be tagged to allow induction by chemicals (including but not limited to the tamoxifen responsive mutated estrogen receptor) in specific cell compartments (including, but not limited to, the cell membrane).

Any of transfection or transduction technique can also be applied to introduce a transcriptional regulatory sequence into cells to activate a desired endogenous gene. This can be done by both homologous (e.g., U.S. Pat. No. 5,641,670) or non-homologous (e.g., U.S. Pat. No. 6,602,686) recombination. These patents are incorporated by reference for teaching of methods of endogenous gene activation.

Successful transfection or transduction of target cells can be demonstrated using genetic markers, in a technique that is known to those of skill in the art. The green fluorescent protein of *Aequorea victoria*, for example, has been shown to be an effective marker for identifying and tracking genetically modified hematopoietic cells (Persons, D., et al., 1998). Alternative selectable markers include the (β-Gal gene, the truncated nerve growth factor receptor, drug selectable markers (including but not limited to NEO, MTX, hygromycin).

Formulations, Dosage Forms and Routes of administration

Cells can be administered systemically or locally. The route of administration used can depend upon the disease/disorder being treated or prevented.

For the purposes described herein, either autologous, allogeneic or xenogeneic cells, or their differentiated progeny, can be administered to a subject, either in differentiated or undifferentiated form, genetically altered or unaltered, by direct injection to a tissue site, systemically, on a surface, on or around the surface of an acceptable matrix, encapsulated or in combination with a pharmaceutically acceptable carrier.

The cells can be provided in a pharmaceutical composition. The pharmaceutical composition can comprise pharmaceutically acceptable diluent(s), excipient(s), or carrier(s). The pharmaceutical compositions can include other medicinal or pharmaceutical agents, carriers, adjuvants, such as preserving, stabilizing, wetting or emulsifying agents, solution promoters, salts for regulating the osmotic pressure, and/or buffers.

Methods well known in the art for making formulations are to be found in, for example, Remington: The Science and Practice of Pharmacy, (20th ed.) ed. A. R. Gennaro A R., 2000, Lippencott Williams & Wilkins. Formulations for parenteral administration may, for example, contain as excipients sterile water or saline, polyalkylene glycols such as polyethylene glycol, oils of vegetable origin, or hydrogenated naphthalenes, biocompatible, biodegradable lactide polymer, or polyoxyethylene-polyoxypropylene copolymers may be used to control the release of the present factors.

Other potentially useful parenteral delivery systems for the factors include ethylene-vinyl acetate copolymer particles, osmotic pumps, implantable infusion systems, and liposomes. Formulations for inhalation may contain as excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally.

The appropriate dosage of cells will depend, for example, on the condition to be treated, the severity and course of the condition, whether the cells are administered for preventive or therapeutic purposes, previous therapy, the patient's clinical history and response to cells, the type of cells used, and the discretion of the attending physician. Cells are suitably administered to the patient at one time or over a series of treatments and may be administered to the patient at any time as necessary for treatment or prevention of disease/disorder. Cells may be administered as the sole treatment or in conjunction with other drugs or therapies useful in treating the condition in question.

The quantity of cells to be administered will vary for the subject being treated. In one embodiment, between about $10^4$ to about $10^8$, such as about $10^5$ to about $10^7$ and including, about $3 \times 10^7$ stem cells can be administered to a human subject. However, the precise determination of what would be considered an effective dose may be based on factors individual to each patient, including their size, age, disease or injury, amount of damage, amount of time since the damage occurred and factors associated with the mode of delivery (direct injection—lower doses, intravenous—higher doses). Dosages can be readily ascertained by those skilled in the art from this disclosure and the knowledge in the art.

Preferable ranges of purity in populations comprising cells, or their differentiated progeny, are about 50-55%, about 55-60%, and about 65-70%. In some embodiments, the purity is about 70-75%, about 75-80%, about 80-85%; and including the purity of about 85-90%, about 90-95%, and about 95-100%. However, populations with lower purity can also be useful, such as about 25-30%, about 30-35%, about 35-40%, about 40-45% and about 45-50%. Purity of cells can be determined according to the gene expression profile within a population.

The skilled artisan can readily determine the amount of cells and optional additives, vehicles, or carrier in compositions to be administered in methods of the invention. Typically, additives (in addition to the cell(s) and/or cytokine(s)) are present in an amount of about 0.001 to about 50 wt % solution in phosphate buffered saline, and the active ingredient is present in the order of micrograms to milligrams, such as about 0.0001 to about 5 wt %, about 0.0001 to about 1 wt %, about 0.0001 to about 0.05 wt % or about 0.001 to about 20 wt %, about 0.01 to about 10 wt %, and about 0.05 to about 5 wt %. Of course, for any composition to be administered to an animal or human, and for any particular method of administration, it is practical to determine therefore: toxicity, such as by determining the lethal dose (LD) and $LD_{50}$ in a suitable animal model e.g., a rodent, such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. Additionally, the time for sequential administrations can be ascertained without undue experimentation.

When administering a therapeutic composition of the present invention, it will generally be formulated in a unit dosage injectable form (solution, suspension, emulsion). The pharmaceutical formulations suitable for injection include sterile aqueous solutions and dispersions. The carrier can be a solvent or dispersing medium containing, for example, water, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells.

Sterile injectable solutions can be prepared by incorporating the cells utilized in practicing the present invention in the required amount of the appropriate solvent with various amounts of the other ingredients, as desired.

In one embodiment, cells can be administered initially, and thereafter maintained by further administration of cells. For instance, cells can be administered by one method of injection, and thereafter further administered by a different or the same type of method.

Examples of compositions comprising cells include liquid preparations for administration, including suspensions, and, preparations for direct or intravenous administration (e.g., injectable administration), such as sterile suspensions or emulsions. Such compositions may be in admixture with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE," 17th edition, 1985, incorporated herein by reference, may be consulted to prepare suitable preparations, without undue experimentation.

Compositions are conveniently provided as liquid preparations, e.g., isotonic aqueous solutions, suspensions, emulsions or viscous compositions, which may be buffered to a selected pH. Liquid preparations are normally easier to prepare than gels, other viscous compositions and solid compositions. Additionally, liquid compositions are somewhat more convenient to administer, especially by injection. Viscous compositions, on the other hand, can be formulated within the appropriate viscosity range to provide longer contact periods with specific tissues.

The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Solutions, suspensions and gels normally contain a major amount of water (preferably purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose), may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is one option for buffers containing sodium ions.

Viscosity of the compositions, if desired, can be maintained at the selected level using a pharmaceutically acceptable thickening agent. Methylcellulose can be used as it is readily and economically available and is easy to work with. Other suitable thickening agents include, for example, xanthan gum, carboxymethyl cellulose, hydroxypropyl cellulose, carbomer, and the like. The concentration of the thickener will depend upon the agent selected and the desired viscosity. Viscous compositions are normally prepared from solutions by the addition of such thickening agents.

A pharmaceutically acceptable preservative or cell stabilizer can be employed to increase the life of the compositions. If preservatives are necessary, it is well within the purview of the skilled artisan to select compositions that will not affect the viability or efficacy of the cells described in the present invention.

Those skilled in the art will recognize that the components of the compositions should be selected to be chemically inert. This will present no problem to those skilled in chemical and pharmaceutical principles, or problems can be readily avoided by reference to standard texts or simple experiments (not involving undue experimentation), from this disclosure and the documents cited herein.

Suitable regimes for initial administration and further doses or for sequential administrations also are variable, may include an initial administration followed by subsequent administrations; but nonetheless, can be ascertained by the skilled artisan, from this disclosure, the documents cited herein, and the knowledge in the art.

Combined Treatment

The cells and composition of the invention can be combined with other, including current, therapies to treat the cancer, autoimmune disease or infectious disease.
For example cells and composition of the invention can be combined with other treatments, including other cancer treatments, such as chemotherapy, radiation and/or other immunotherapies, such as CAR T therapy, dendritic cell-based pump-priming. T-cell adoptive transfer, immune enhancement therapy, genetically engineered T cells, immune recovery and/or vaccination. For autoimmune diseases, the cells and composition of the invention can be combined with other treatments, such as suppression immunotherapies, include immunosuppressive drugs. For infectious diseases, the cells and composition of the invention can be combined with other treatments, such as antibiotics, antivirals, antifungals, antiprotozoals, and antihelminthics.

EXAMPLES

The following examples are provided in order to demonstrate and further illustrate certain embodiments and aspects of the present invention and are not to be construed as limiting the scope thereof.

INTRODUCTION

Current cancer immunotherapies: Cancer immunotherapies have evolved rapidly and are poised to become the most promising cancer treatment available. Significant progress recently has been made with three therapeutic approaches. The first is "immune checkpoint therapy" which was developed by James Allison and is largely focused on the development of more efficient inhibitors of immunosuppressive signals found in the tumor microenviroment (4-6). The second is "adoptive cell therapy," pioneered by Steven Rosenberg and is based on the in vitro expansion (>1000 fold) of tumor-derived infiltrating T cells and subsequent injection back into patients (7, 8). Although both methods demonstrated improvement ofT cell responses, significant cancer regression was shown only in cases with highly immunogenic tumors. The third approach uses the adoptive transfer of T cells that are engineered to express anti-tumor T cell receptors (TCR) (9, 10) or chimeric antigen receptors (CARs) (11, 12) that in turn increase tumor "immunovisibility." Despite the fact that this therapy has been successful for a few types of cancer, it remains highly personalized and expensive. Herein it is proposed to increase the efficacy of CTL based immunotherapies with a novel strategy using a cell-intrinsic mechanism of gene regulation, namely, down-regulation of let-7 microRNA expression, which as shown in the results provided herein, substantially increases the cytotoxic activity of the CTLs.

Let-7 microRNA Biology:

MicroRNA-mediated post-transcriptional regulation of gene expression and cell function is an exciting and emerging field. In humans, let-7 is the largest conserved family of microRNAs with 14 gene paralogs encoded on 10 different chromosomes. All members of the let-7 family share the same sequence that determines their specificity towards targeted mRNAs. Let-7 microRNAs have been shown to play a role in embryogenesis and cancer (13, 14). In fact, let-7 has been recently characterized as a potent tumor-suppressor factor (14). In T cells the let-7 family of microRNAs plays a role in lymphocyte development and differentiation (3). Specifically, let-7 microRNAs directly target the key transcription factor for NKT cell differentiation and subsequent programming of their effector functions. Furthermore, the data show that let-7 may play a role in the global regulation of $CD4^+$ and $CD8^+$ T cell-mediated immune responses. Thus, understanding of the mechanisms that regulate let-7 expression is potentially important for therapeutic applications. Herein it is proposed to identify the transcription factors that are responsible for let-7 expression in T cells as these will provide new targets for therapy.

The goal was to identify factors that will improve immune responses against tumors/enhancement of CTL function in human tumor-infiltrating lymphocytes. The overall objective was to determine the molecular mechanism that directly enhances differentiation and effector functions of anti-tumor CTLs in vivo. Several lines of evidence have shown that genetic manipulations that promote CTL differentiation result in improvement of their anti-tumor activity (1, 2). Results presented herein show that a unique microRNA (let-7) is a "master regulator" of T cell responses (including both T-helpers and CTLs): a reduction of let-7 expression results in enhanced effector functions, and upregulation diminishes the ability to respond. Specifically for CTLs, as described herein, it has been determined that let-7 microRNAs regulate CTL differentiation through direct targeting of the transcription factor Eomes. Herein it disclosed that the success of the CTL-mediated anti-tumor immune response can be significantly impacted by expression of let-7 in T lymphocytes (FIG. 1A). To define the role of let-7 microRNAs in anti-tumor CTL-mediated immunity and identify molecular mechanisms of regulation of let-7 expression the following was undertaken.

Example 1—Results

It was found that let-7 is the most abundantly expressed family of microRNAs in T lymphocytes (3) and is reduced in differentiating T cells (FIG. 2). These data suggest that a functional reduction of let-7 plays a role in the differentiation and function of effector T cells. In line with other published results (15), the data herein suggest that let-7 is a "master regulator" of T cell responses (including both T-helpers and CTLs) where a reduction of let-7 results in enhanced effector function, and overexpression diminishes the ability to respond.

Tools for Manipulation of Let-7 Levels.

Mice were generated with T cell-specific expression of the Lin28 protein, which selectively blocks let-7 microRNA biogenesis (3, 16-19). Lin28 protein binds to the extended loop region of let-7 precursor molecules and prevents them from being processed into functional mature microRNAs. Also, a doxycycline-inducible let-7 transgenic mouse line was generated to overexpress a single member (let-7g) of the let-7 microRNA family (20), which because of the conserved RNA binding site of let-7 family members, results in an increase of generic activity of let-7 in induced cells. The overall development of conventional T cells that develop in let-7 and Lin28 transgenic mice is similar to that of wild-type (non-transgenic) control animals (3). These tools allow one to experimentally turn let-7 expression off and on.

Let-7 Regulates Eomes, a Transcriptional Factor for CTL Differentiation.

The data show that knockdown of let-7 (Lin28 transgene) increases expression of effector molecules in differentiated CTLs in vitro, while let-7 overexpression (let-7 transgene) does the opposite (FIG. 3A,B). Specifically, let-7-deficient CTLs express very high levels of cytolytic proteins (Granzyme-A, Granzyme-B and Perforin), while let-7 transgenic CTLs have very low levels. The activation and the proliferation rate of these T cells in vitro were similar to control wild-type cells. Furthermore, it was found that let-7 microRNAs actively suppress expression of Eomesodermin (Eomes), a T cell-specific transcription factor (TF) that regulates the differentiation and function of CTLs (21), while lin28-mediated knockdown of let-7 microRNAs induces upregulation of Eomes expression (FIG. 4A). In fact, a let-7 binding motif was identified within the open reading frame (ORF) of Eomes mRNA that is conserved between mice and humans (FIG. 4B). Using a luciferase reporter assay, it was confirmed that let-7 does target this sequence (FIG. 4C). These results suggest that let-7 suppresses CTL maturation through direct targeting of Eomes mRNA.

Let-7 Controls CTL Function.

Figure 5A:
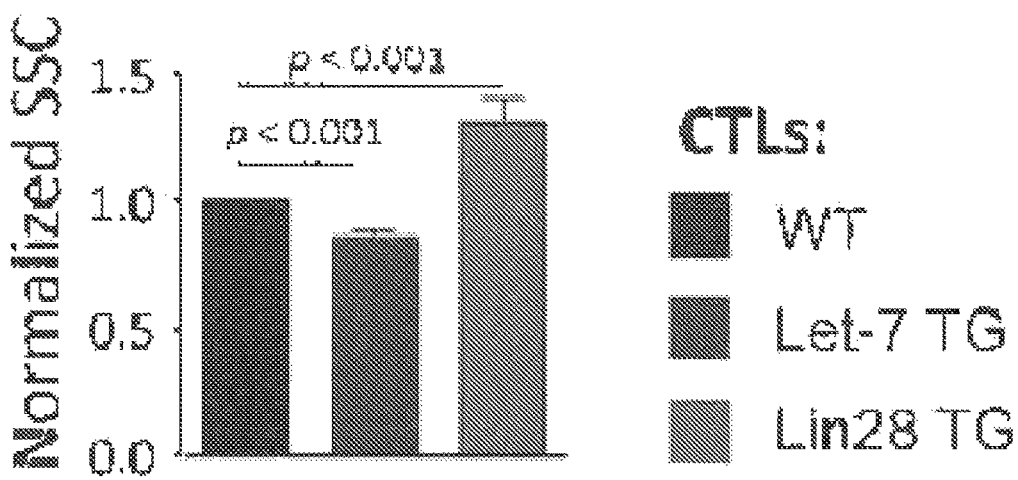
FIGS. 5A-D Let-7 regulates CTL function: Side scatter (SSC) parameter for CTLs on the 5th day of differentiation culture (n=3) (A). Number of granzyme-B positive granules in CTLs (B). Experimental design of cytotoxic assays: CTLs with P14 T cell receptors will recognize gp33 peptide in the complex with MHC class I on the surface of splenocytes. This interaction will trigger CTL cytotoxic activity towards splenocytes (C). Cytotoxic assay: P14 CTL-mediated lysis of wild type (C57/BL6) splenocytes loaded with gp33 peptide (filled) or control peptide (open) (n=3) (D).
Figure 5B:
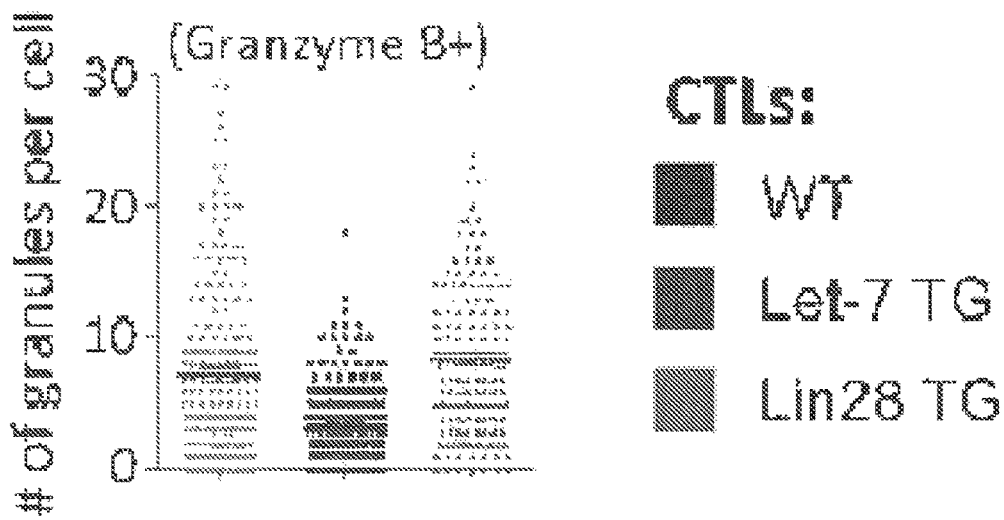
Figure 5C:
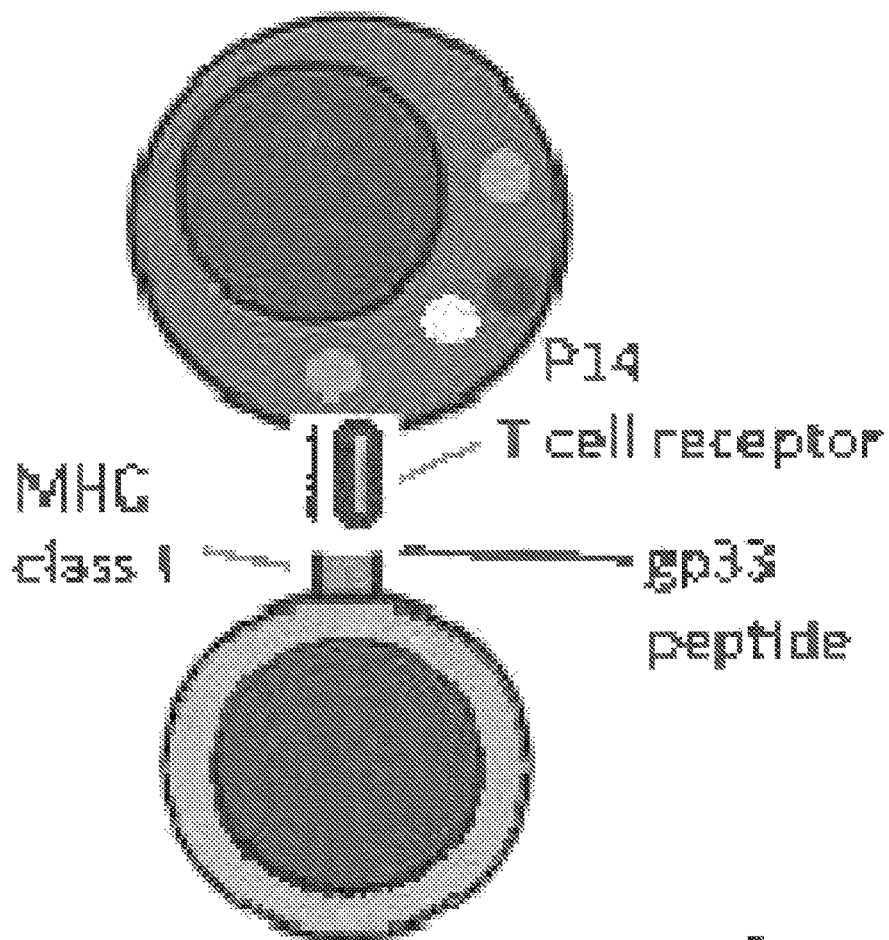
Figure 5D:
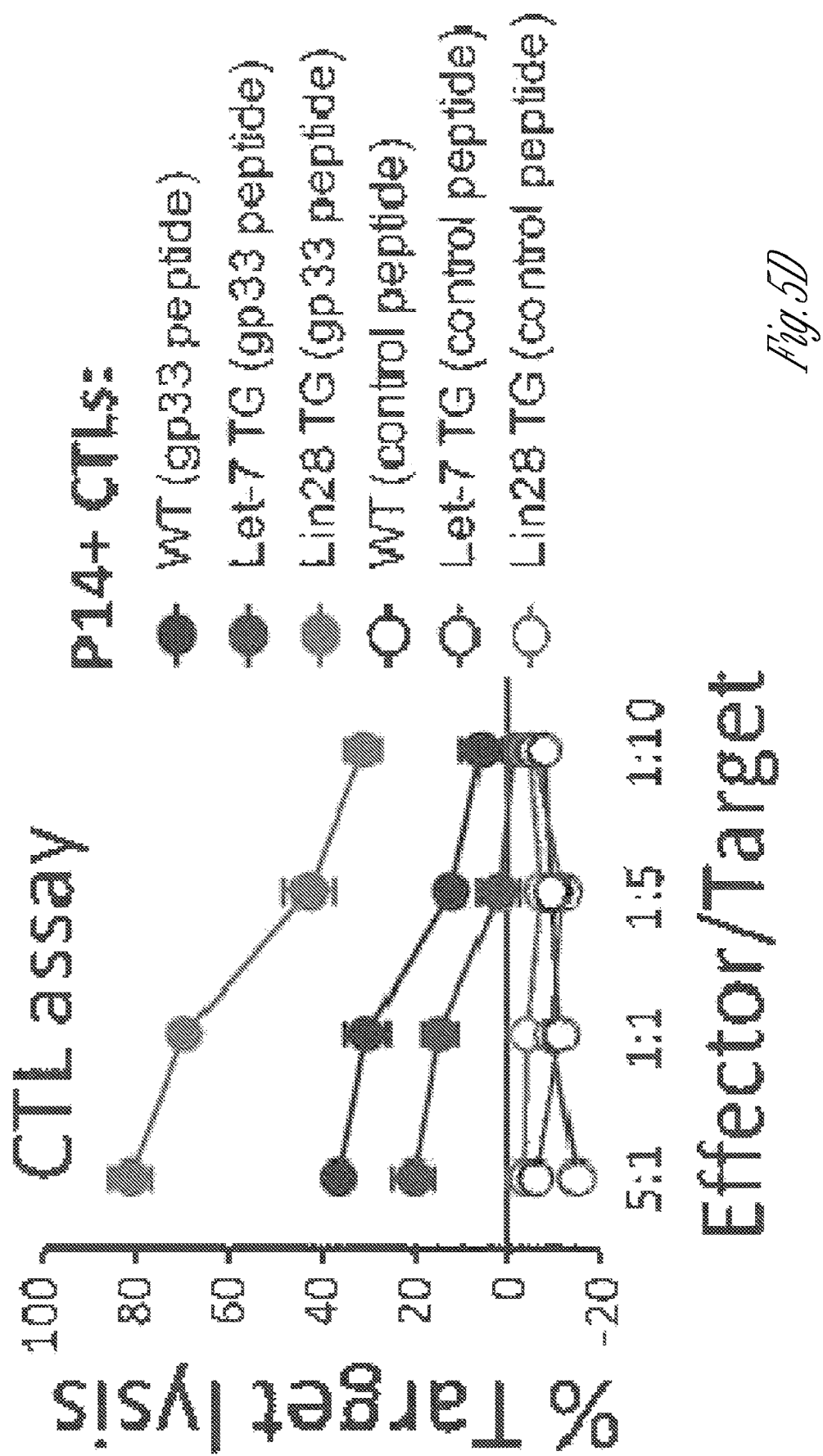

The pore forming protein perforin and pro-apoptotic enzymes granzymes are packed in cytotoxic granules in CTL. Release of these granules at the CTL and target cell synapse causes target cell apoptosis/lysis. Overexpression of these cytolytic proteins in response to the Lin28 transgene correlates with an increase in granularity/internal complexity of CTLs, while decreased expression in response to the let-7 transgene correlates with less granularity/complexity as measured by side scatter compared to control (wild-type) CTLs (FIG. 5A). These changes in internal complexity are directly due to changes in the numbers of cytotoxic granules determined using the Amnis imaging flow cytometer (FIG. 5B). Since it is known that CTL granules contain cytolytic proteins, these results suggest a better cytotoxic activity of CTLs with decreased let-7 microRNA expression. This notion was confirmed by directly testing the impact of let-7 microRNAs on CTL function using effector cells with low (wild type control), high (let-7 transgenic) and depleted (Lin28 transgenic) let-7 expression in an in vitro non-radioactive cytotoxic assay (22). For this experiment CTLs were differentiated in vitro (5-7 days) from T cells of P14+, P14+Let-7TG+ and P14+Lin28TG+ transgenic mice (where P14 is the CD8-specific T cell receptor that recognizes a specific antigen, the LCMV-derived gp33 peptide in the context of MHC class I molecules). gp33-peptide pulsed wild-type splenocytes were used as specific cell targets for the P14+, P14+Let-7+ and P14+Lin28TG+ CTL-mediated lysis (FIG. 5C). It was observed that let-7 deficient CTLs (P14+Lin28TG+) were 50-fold more efficient in the killing of specific targets than the control wild-type cells (P14+), while let-7 transgenic CTLs had substantially decreased cytotoxic activity (FIG. 5D). Furthermore, it was demonstrated that the enhanced cytotoxic response of Lin28 transgenic CTLs is indeed due to let-7 deficiency because re-expression of let-7 in Lin28 transgenic CTLs leads to a reduction of cytotoxicity to a wild-type level (data not shown). These results indicate that lin28-mediated knockdown of let-7 microRNAs in CD8 T cells promotes differentiation and effector function of CTLs in vitro and suggest that similar mechanisms will operate in vivo.

DISCUSSION

The involvement of let-7 microRNAs has been demonstrated in many biological processes. Moreover, let-7 therapeutic potentials in cancer have been appreciated since the original discovery of microRNAs with let-7 having been well-recognized as a tumor suppressor (13, 23-25). However, the role of let-7 in the immune system was only recently assessed during hematopoiesis, albeit indirectly (26) and T cell development (3). Besides a weak inhibitory effect of let-7-containing exosomes on T helper-1 cells (15) and let-7-mediated modulation of CD4 T cell metabolism (27), there is no direct evidence of the regulatory activity of let-7 microRNAs in T cells. Herein it discussed whether down-regulation of let-7 expression in CTLs results in enhanced cytotoxic responses and improved survival in mouse tumor models. The research and conclusions are innovative, new and unique because it focuses on the generation of anti-tumor CTLs with markedly enhanced cytotoxic activity (dubbed "SUPER-CTLs") by down-regulating the levels of let-7 expression in CD8 T cells, which has never been done before. The Lin28-mediated let-7 knockdown in CTLs results in a 50-fold increase of cytotoxic activity. The idea to improve the anti-tumor response by enhancing CTL cytotoxic function is novel and can be the basis of innovative translational application. The methods and compositions described herein will generate new therapeutic horizons for cancer immunotherapies. In addition, the advances made with modulation of let-7 expression in T cells is transferable to other immunological models to enhance or suppress T cell mediated immunity.

Example 2—Let-7 microRNA Expression can Control CTL-Mediated Anti-Tumor Responses Genetic tools have been developed that allowed the investigation of the role of let-7 microRNAs in tumor-specific CTLs in vitro and in vivo. Based on the results demonstrating that let-7 microRNAs profoundly suppress the differentiation of CTLs, it is believed that let-7-deficient T cells differentiate into enhanced tumor-specific CTLs (FIG. 1B). To test this, mouse tumor models will be used to address the role of let-7 microRNAs in CTLs during anti-tumor responses in vivo. Specifically, the impact of the tumor immunosuppressive environment on let-7 regulated CTL functions with and without the synergistic effect of immune blockade therapy will be investigated. Furthermore, the role of let-7 in the generation of anti-tumor memory T cells will be investigated.

In vitro experiments (see above) have demonstrated that let-7 deficient CTLs have superior cytotoxic function (FIG. 5D). Based on data presented herein, it is believed that let-7 microRNA will suppress, while let-7 deficiency will enhance anti-tumor CTL responses. The effector function of CTLs and memory T cells against tumor cell lines will be tested both in vitro and in vivo by specifically manipulating the levels of let-7 expression.

Figure 6A:
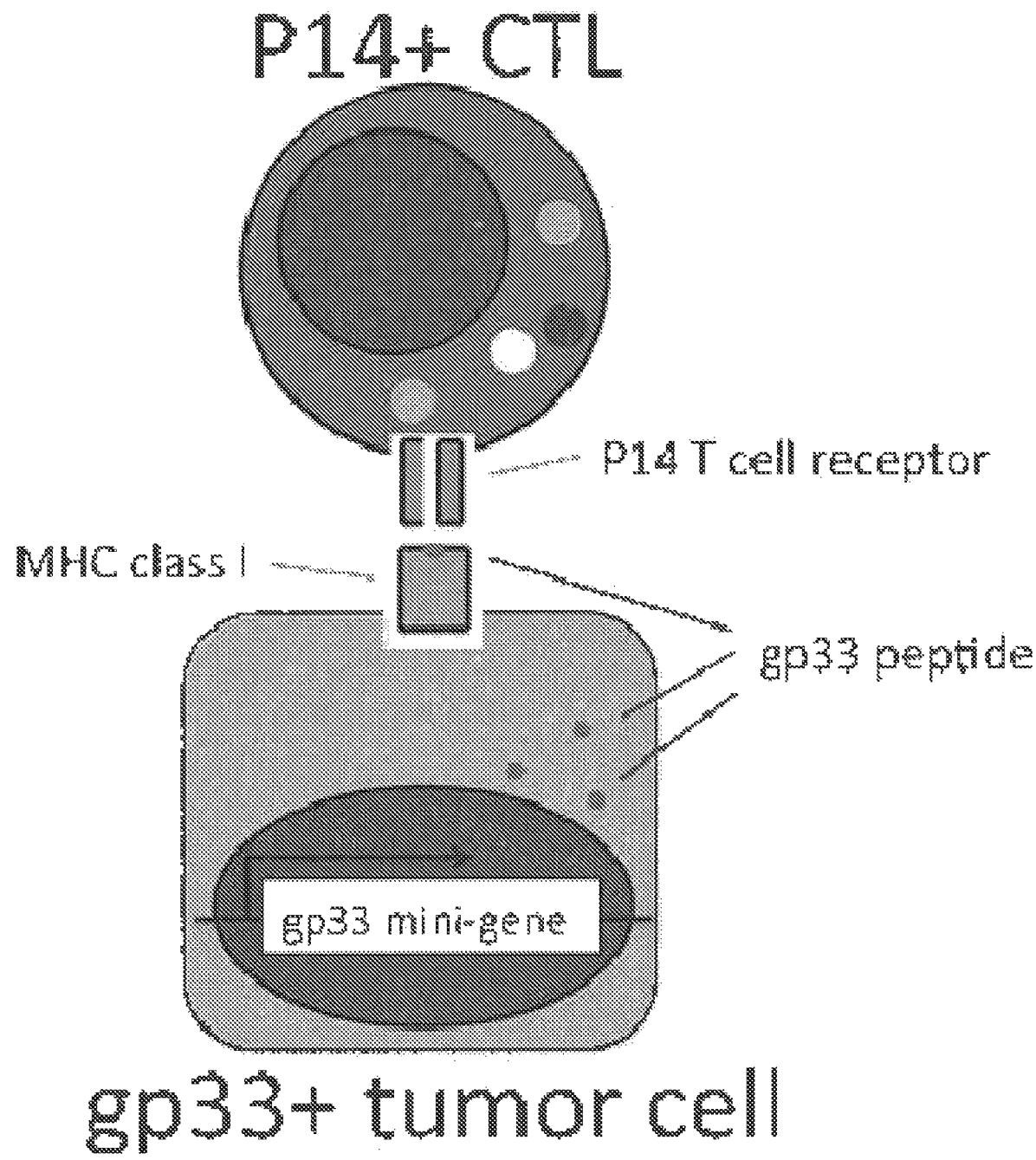
FIGS. 6A-B CTLs with P14 T cell receptors will recognize gp33 peptide in the complex with MHC class I on the surface of tumor cells. This interaction will trigger CTL cytotoxic activity towards tumor cells (A). Schematic overview of mouse tumor models.

To eliminate bystander effects from other T cells on the development and differentiation/function of CTLs (3,26,35) and to focus CTL responses on a single antigen, two double transgenic mouse strains P14+Lin28+ and P14+Let-7+ on RAG2-knockout background (where P14 is the CD8-specific T cell receptor that recognizes a specific antigen, the LCMV-derived gp33 peptide) were developed. To ensure antigen-specific tumor recognition by P14 CTLs, tumor cell lines were transduced with a mini-gene encoding the gp33 peptide36 and a GFP reporter (gp33-IRES-GFP) (FIG. 6A). GFP expression was used in these tumor cell lines to adjust the expression levels of peptide for in vitro and in vivo experiments. As specificity controls, tumor cell lines that are transduced with empty vector (IRES-GFP) and a mini-gene encoding the control non-specific LCMV-derived np396 peptide (np396-IRES-GFP) will be used. For in vivo studies, tumor cell lines will be transduced with a luciferase-based reporter in addition to the gp33 mini-gene. With the retroviral vector encoding the enhanced firefly luciferase (eLuc-IRES-Thy1.1) that generates over 100 times more light than conventional luciferase37, the Thy1.1 reporter will be used to adjust the expression levels of luciferase in tumor cells for in vivo experiments. The luciferase reporter in tumor cells will allow one to monitor the efficiency of CTL-mediated tumor killing and tumor mass regression in live animals using full body bioluminescence imaging via the IVIS Spectrum™ µCT.

In vitro anti-tumor activity of CTLs will be assessed with different levels of let-7 microRNA expression. Prior to in vivo experiments it will be validated that P14+ CTLs can target and eliminate gp33 positive tumor cells in vitro. The cytotoxic function of P14+ wild-type, P14+Lin28TG+ and P14+Let-7TG+ CTLs will be tested against syngeneic tumor cell lines that express the gp33 mini-gene in an in vitro non-radioactive cytotoxicity assay (22). Briefly, electronically sorted naïve (CD8+, CD44$^{low}$, CD122$^{low}$) P14+ T cells will be stimulated with anti-CD3 (5 ug/ml) and anti-CD28 (5 ug/ml) antibodies for two days, then pre-activated P14+ T cells will be cultured in the presence of IL-2 for an additional 3-5 days to generate fully mature CTLs. For cytotoxic assays the four C57BL/6-derived tumor cell lines (EL-4, 3LL, MCA-38, B16F10) will be used as targets that have different origins and have been previously characterized in mouse tumor models. These experiments will quantify the anti-tumor cell activity of CTLs in vitro providing information to optimize the in vivo experiments.

It will be determined experimentally whether let-7 deficiency in T cells will facilitate the anti-tumor immune response and will overcome the tolerance that is induced by the tumor-mediated immunosuppressive microenvironment. One main difference between tumor cell lines and actual tumors is the acquisition of a tumor microenvironment. It has been well documented that tumors can use different cell types to create an immunosuppressive environment that inhibits and prevents immune responses against cancer (4, 38). As a part of the immunosuppressive milieu, T regulatory cells (Tregs), myeloid derived suppressor cells (MDSCs) and tumor associated macrophages (TAMs) are very often found in high numbers in tumors, where they actively inhibit immune responses against cancer cells (38-41). It is believed that transferring let-7 deficient CD8 T cells will increase the therapeutic efficacy of various forms of T cell-based immunotherapy, by overcoming the immunosuppressive tumor microenvironment.

Figure 6B:
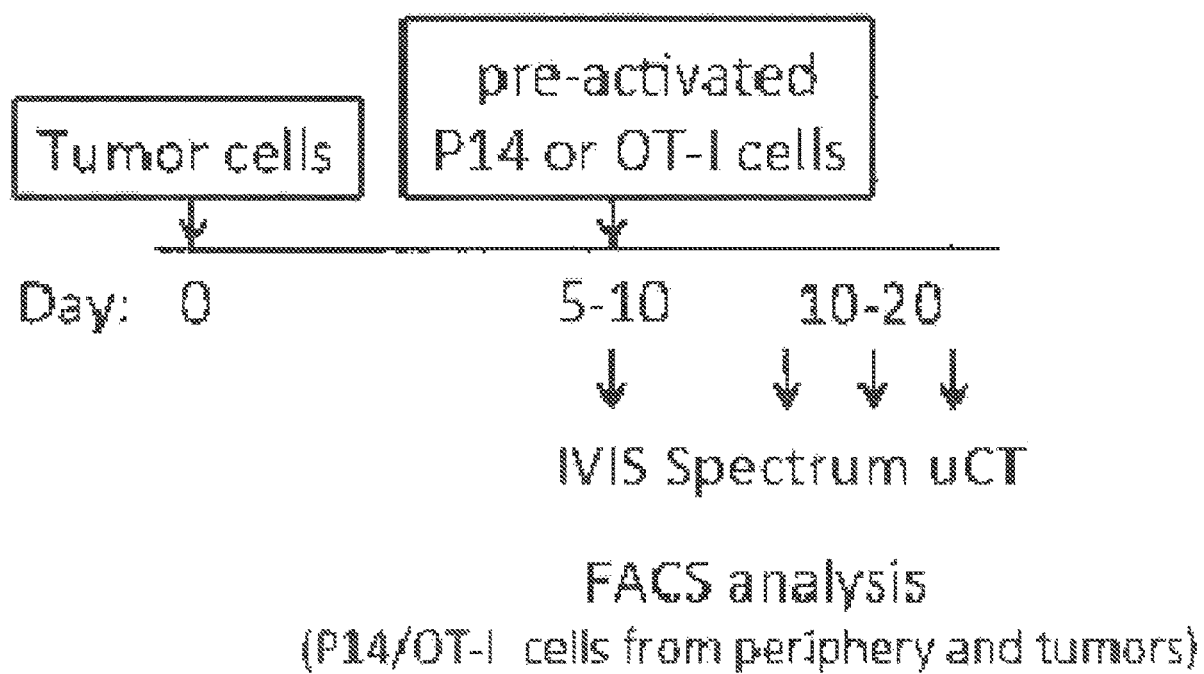

LCMV-gp33 specific CTLs and several gp33-expressing tumor cell line will be used to test the anti-tumor activity of wild-type, let-7 deficient or let-7 transgenic T cells in vivo, and to determine the impact of the tumor immunosuppressive environment on the cytotoxic function of these CTLs (FIG. 6B). Solid tumors will be generated by s.c. injection of EL-4 lymphoma, 3LL lung carcinoma and MCA-38 colon adenocarcinoma tumor cell lines, which generate profound immunosuppressive tumor micro-environment in vivo by recruiting an ensemble of Tregs, MDSCs and TAMs (33, 42-47). In vitro pre-activated (for 24-48 hours) P14+ (TCR transgenic, gp33-specific) T cells will be adoptively transferred into mice bearing EL-4-gp33-luc, 3LL-gp33-luc and MCA-38-gp33-luc tumors for 5-10 days. Different CD45 congenic animals will be used to discriminate between donor (CD45.2) and host (CD45.1) T cells upon transfer. CTL-mediated tumor clearance will be monitored by disappearance of luciferase activity in live mice using the IVIS Spectrum.iCT and mouse survival. To define the degree of maturation of CTLs with different levels of let-7 during anti-tumor responses, tumor infiltrating P14+ CTLs will be isolated ex vivo and the expression of a variety of activation and differentiation markers will be measured including KLRG-1, perforin, granzyme A/B, and CD107, in addition to Eomes, the key transcription factor for CTLs. Using in vitro restimulation culture in the presence of gp33 or control peptide, the production of the effector cytokines, IFN-γ and TNF-α will also be assessed. Total splenocytes or tumor-infiltrating effector CTLs from experimental mice will be isolated and re-stimulated in the presence of gp33 or control peptide. Next, the impact of the tumor immunosuppressive environment on P14+ wild-type, P14+Lin28TG+, or P14+Let-7TG+ CTLs will be analyzed using markers that are known to appear on suppressed or exhausted T cells (PD-1, LAG-3, Tim-3, CD160, 2B4). The expression of all these markers will be measured at the protein level by FACS analysis.

To confirm the results, OT-I, another well-established mouse model, whose CD8+ T cells express a transgenic TCR that recognizes the ovalbumin (OVA) peptide, SIINFEKL, that is expressed by 3LL-OVA tumors, will be used. Pre-activated OT-I+ let-7-deficient or control (OT-I+ wild-type, OT-I+Let-7TG+) CD8+ T cells will be adoptively transferred into mice bearing similar size 3LL-OVA-luc Lewis lung carcinoma tumors. Tumor growth and mouse survival will be tested. In addition, the phenotype of effector cells will be analyzed as described above.

It is expected that the expression of let-7 will inversely correlate with the status of CTL differentiation/function, where let-7 deficient T cells will become tumor "SUPER-killers," while the cytotoxic activity of let-7 transgenic cells will be greatly reduced or absent. let-7 deficient cells will be less sensitive to Treg/MDSC/TAM-mediated suppression while let-7 transgenic CTLs will be more prone to inhibition, in comparison to the control (wild type) cells. In addition these models will allow one to determine the optimal activation status of let-7 deficient P14+ cells for the best performance in future experiments.

The information from these experiments will advance the understanding of the mechanisms that are involved in inhibition of anti-tumor CTL-mediated responses and be useful in guiding the development of more effective cancer immunotherapies.

Figure 7A:
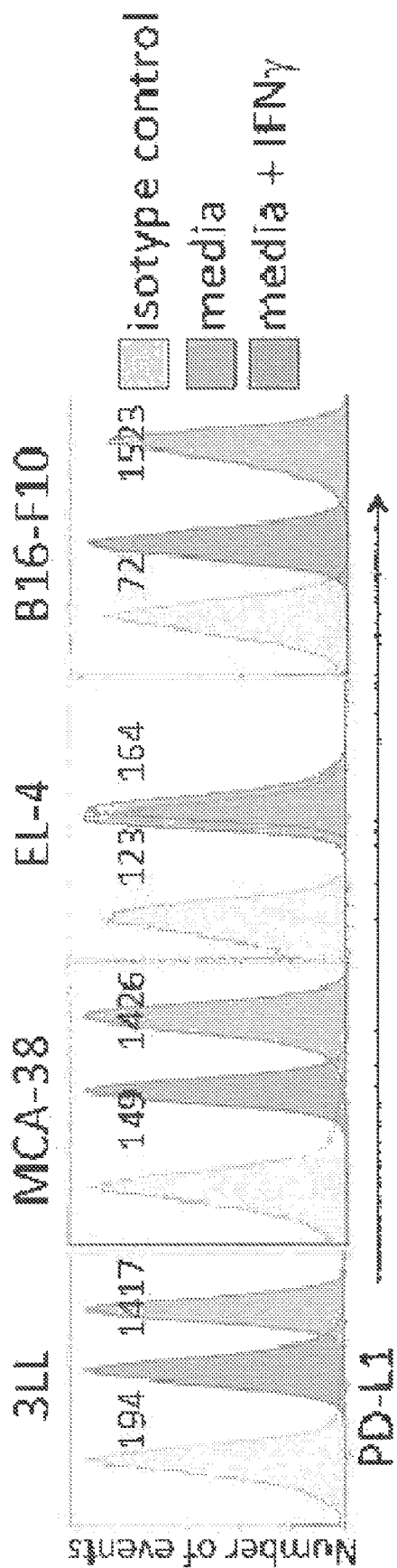
Figure 7B:
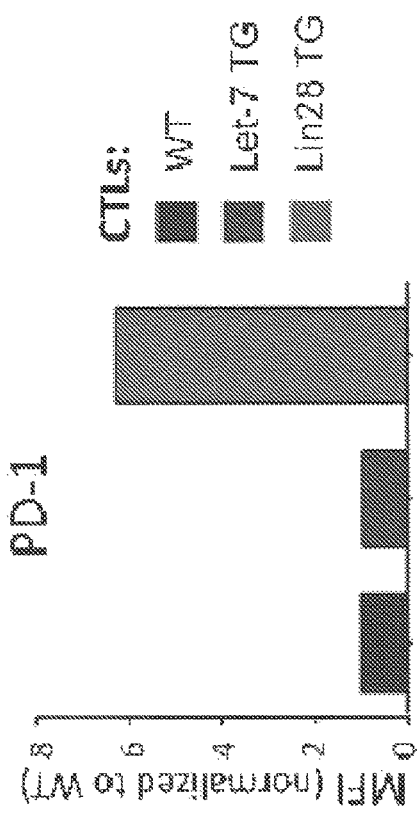

The possibility to further enhance the anti-tumor response of let-7 deficient CTLs by using checkpoint therapy will be explored. Recent advances in checkpoint blockade based therapy demonstrate impressive clinical responses (6, 48, 49). Immunosuppressive resistance of many types of tumors can be partially overcome with antibody treatment that provides CTLA-4 and PD-1/PD-L1 blockade. Anti-PD-1/PD-L1 antibody treatment promotes activation and differentiation of effector T cells. PD-1 is a receptor that is expressed on activated/differentiated T cells, including CTLs. Engagement of PD-1 receptor by its ligand PD-L1, negatively regulates T cell responses. Different stimuli including exposure to IFNs can induce the expression of PD-L1 molecules on tumor infiltrating lymphocytes and other leukocytes such as MDSCs & TAMs and tumor cells themselves (FIG. 7A). Elevated levels of PD-L1 can lead to T cell exhaustion, which is characterized by compromised proliferation and effector function of T cells (50, 51). The data show that let-7 deficient CTLs express higher levels of the PD-1 receptor and IFN-γ than let-7 sufficient or transgenic cells (FIG. 7B). Based on these results it is believed that PD-1/PD-L1 blockade will further improve the anti-tumor immune responses that are mediated by let-7 deficient CTLs.

To test this, a tumor model testing reactivity against the LCMV-gp33 antigen as described above will be used. Two 3LL-gp33-luc and MCA-38-gp33-luc tumor cell line will be used. Repeated treatment of gp33-tumor bearing mice with anti-PD-1/PD-L1 antibodies (i.p. 200 ug per mouse) on day 6, 9 and 12 after adoptive transfer of pre-activated P14+ Lin28TG+ or control, wild-type P14+ cells will occur. Tumor growth/elimination and mouse survival will be monitored.

Figure 8A:
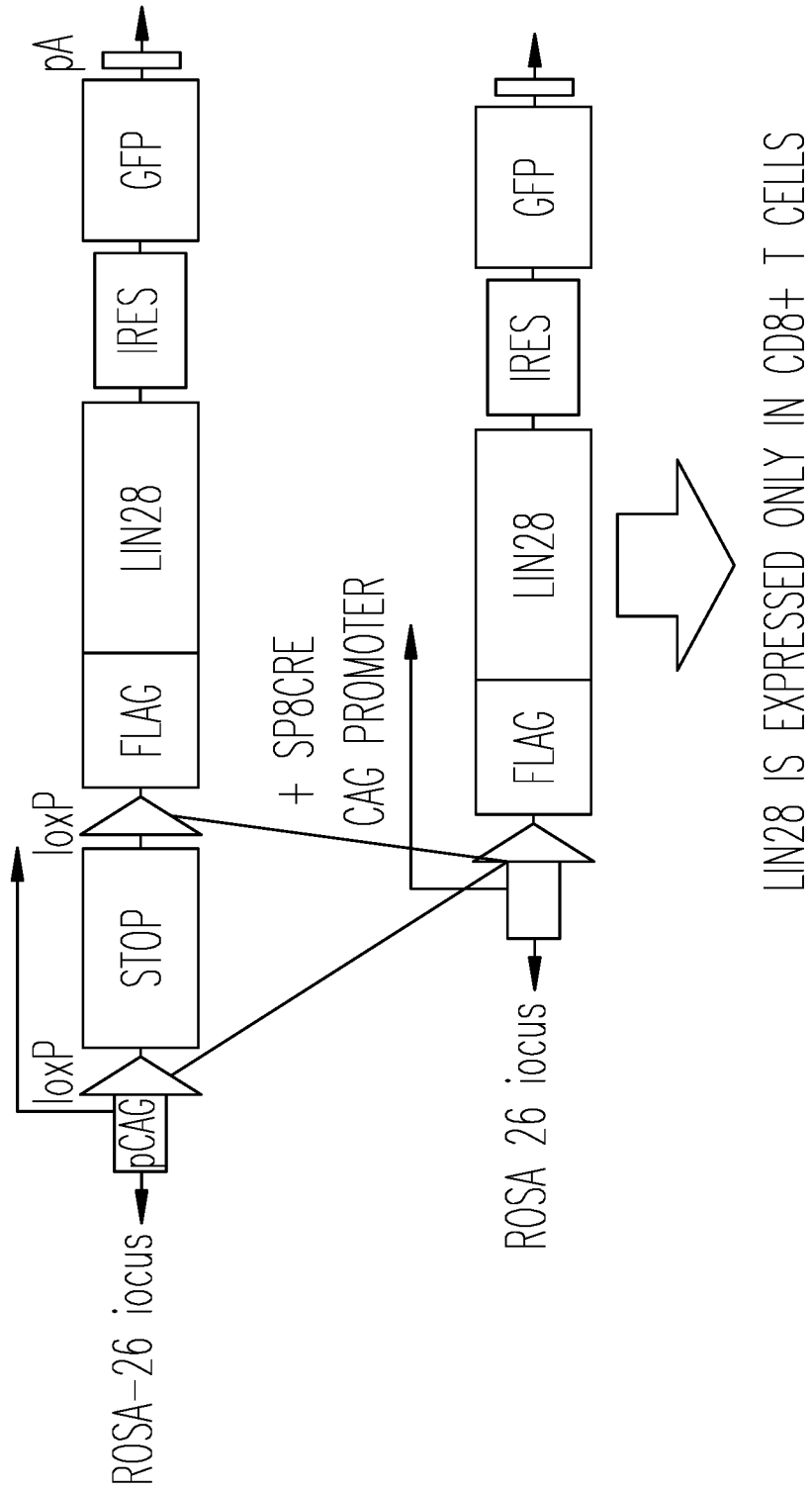
FIGS. 8A-B STOPLIN28GFP knockin mice. Expression of Lin28-GFP knockin is regulated by tissue specific CRE recombinase (A). Schematic overview of mouse tumor treatment protocol.
Figure 8B:
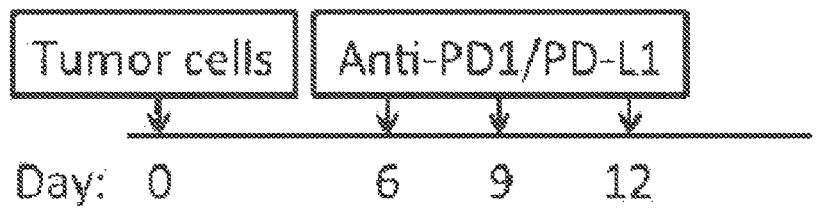

Next, to investigate whether let-7 mediated effects on CTL function are not restricted to P14+ T cells, it will be tested whether genetic ablation of let-7 expression in a polyclonal population of CD8 T cells, together with PD-1/PD-L1 blockade will enhance tumor rejection and improve animal survival. To selectively knockdown let-7 expression in all mature CD8 T cells double transgenic mice (SP8CRE+ STOPLIN28GFP+) were generated from intercross between CD8-specific CRE (SP8CRE+) (52) and loxP-STOP-loxP-Lin28-GFP (STOPLIN28GFP+) transgenic knockin animals (FIG. 8A). Melanoma B16F10-luc will be injected into experimental SP8CRE+STOPLIN28GFP+ and control STOPLIN28GFP+ groups of mice. These mice will be repeatedly treated with anti-PD-1/PD-L1 antibodies (ip 200 ug per mouse, on day 6, 9 and 12) to enhance the cytotoxic activity of endogenously generated CTLs (FIGS. 8B and 49). Data will be collected, analyzed and compared from the experiment as it is described above. Tumor growth/elimination and mouse survival will monitored.

Together, these experiments will demonstrate the impact of let-7 on the anti-tumor function of CTLs in vitro, and in vivo. Additionally, these results will support the use of Lin28 itself to reprogram CTLs in adoptive cell therapy for human cancer treatment.

The superior performance of anti-tumor let-7 deficient CTLs will be further improved with PD-1/PD-L1 blockade and will result in tumor elimination and animal survival. The information from these experiments can be used for further developing cancer immunotherapies and in particular to greatly increase the efficiency of CTL-mediated adoptive tumor infiltrating cell therapy.

The role of let-7 microRNAs in CD8-mediated anti-tumor memory formation will be investigated. In addition to the immunosuppressive tumor microenvironment, a major concern for adoptive immunotherapy against cancer is the rapid disappearance of tumor-antigen specific T cells after infusion, leading to poor clinical activity (54, 55). An effective vaccination strategy that can generate long-lasting tumor-specific memory T cells is highly desirable, but not yet achieved. It has been shown that the induction of Eomes expression during the differentiation of CD8 T cells plays a key role in establishing the memory program in CTLs (56, 57). The data presented herein clearly indicate that let-7 microRNAs control expression of Eomes in effector T cells, with let-7 deficient CTLs exhibiting elevated levels of Eomes (FIG. 3). It was also determined that CD8 T cells with a memory-like phenotype express lower levels of let-7 microRNAs than their naïve counterparts. Based on these results it is believed that memory generation in let-7 deficient CTLs is superior to that displayed by let-7 wild-type CTLs.

Based on the results from above, the optimal protocol where full CTL-mediated tumor rejection is achieved will be chosen. Donor pre-activated CD45.2+P14+ T cells that express different levels of let-7 microRNA (P14+ wild type, P14+Lin28TG+ and P14+Let-7TG+) will be injected into CD45.1+CD45.2+ mice bearing the chosen tumor-gp33-luc (established by s.c. injection 5-10 days earlier).Fully mature memory cells will develop in 45-60 days after CTL transfer. Two approaches will be used to explore the effect of let-7 microRNA expression on the generation of anti-tumor memory T cells. First, the presence of memory P14+ T cells in the experimental mice will be determined. Using flow cytometry, the phenotype of the P14+ memory population present in the lymph nodes and spleens of experimental animals will be analyzed. It has been shown that different subtypes of memory T cells have different longevity (58). Focus will be on three main populations of memory T cells, central memory (CD44+, CD62L+, CCR7+, eomeshi, CD122hi, CXCR3+), effector memory (CD44+, CD62L−, CCR7−, eomeslow, CD122hi, CXCR3+) and stem cell memory (CD44−, CD62L+, CCR7+, Sca1+, CD122hi, CXCR3+, Bc12+)59. The results from these experiments will reveal the role of let-7 microRNAs in the generation of memory T cell subsets that have different properties in the memory response (60).

Next, the efficacy of the recall anti-tumor response mediated by P14+ T cells with different levels of let-7 expression in mice following reimplantation of their luciferase-labeled target tumor will be tested. Tumor rejection/growth in these mice using bioluminescence imaging via the IVIS Spectrum™ μCT and mouse survival will be monitored. Next, the mice that have already generated gp33-specific memory T cells will be challenged with a different bystander tumor. Very aggressive melanoma B16F10-gp33-luc, elimination of which requires a very strong CTL immune response, was chosen (49, 61). An additional advantage of this model is that potential host-driven memory immune responses will be practically eliminated due to the fact that B16F10 melanoma shares only one antigen with the initial tumor, gp33. Thus, the survival of these mice will be solely dependent on the efficacy of the immune responses mediated by P14+(gp33 specific) memory T cells against B16F10 melanoma cells. Again, tumor rejection/growth in these mice using bioluminescence imaging by the IVIS Spectrum™ µCT will be monitored. The differentiation status of memory-derived CTLs during the secondary response will be monitored by evaluating production of the effector cytokines INF-gamma, TNF-alpha, and IL-2 following in vitro restimulation with gp33 or control peptide pulsed syngenic splenocytes which provide antigen presenting cells. The results from these experiments will provide information about the efficacy of let-7 deficient memory T cells in anti-tumor immune responses.

Based on the data it is expected that let-7 deficient T cells will generate long-term central memory (CD44+, CD62L+, CCR7+, eomeshi, CD122hi, CXCR3+) T cells that will have superior effector functions during the secondary response to tumor.

Example 3—T Cell-Specific Transcription Factors (TFs) that Control Let-7 Expression Previously it has been reported that undifferentiated mature T cells express very high levels of let-7 microRNAs (Pobezinsky L. A. et al. Nature Immunology, 2015; 3). It is believed that T cells have unique mechanisms that control the expression of let-7 microRNAs (FIG. 1C). The TFs that regulate let-7 microRNA genes in T cells will be identified using two methods: (1) computational analysis and (2) high throughput unbiased screen employing CRISPR-Cas9 technology. Identified candidate TFs will be tested in vitro and in vivo for their ability to control let-7 expression in T lymphocytes.

Figure 9A:
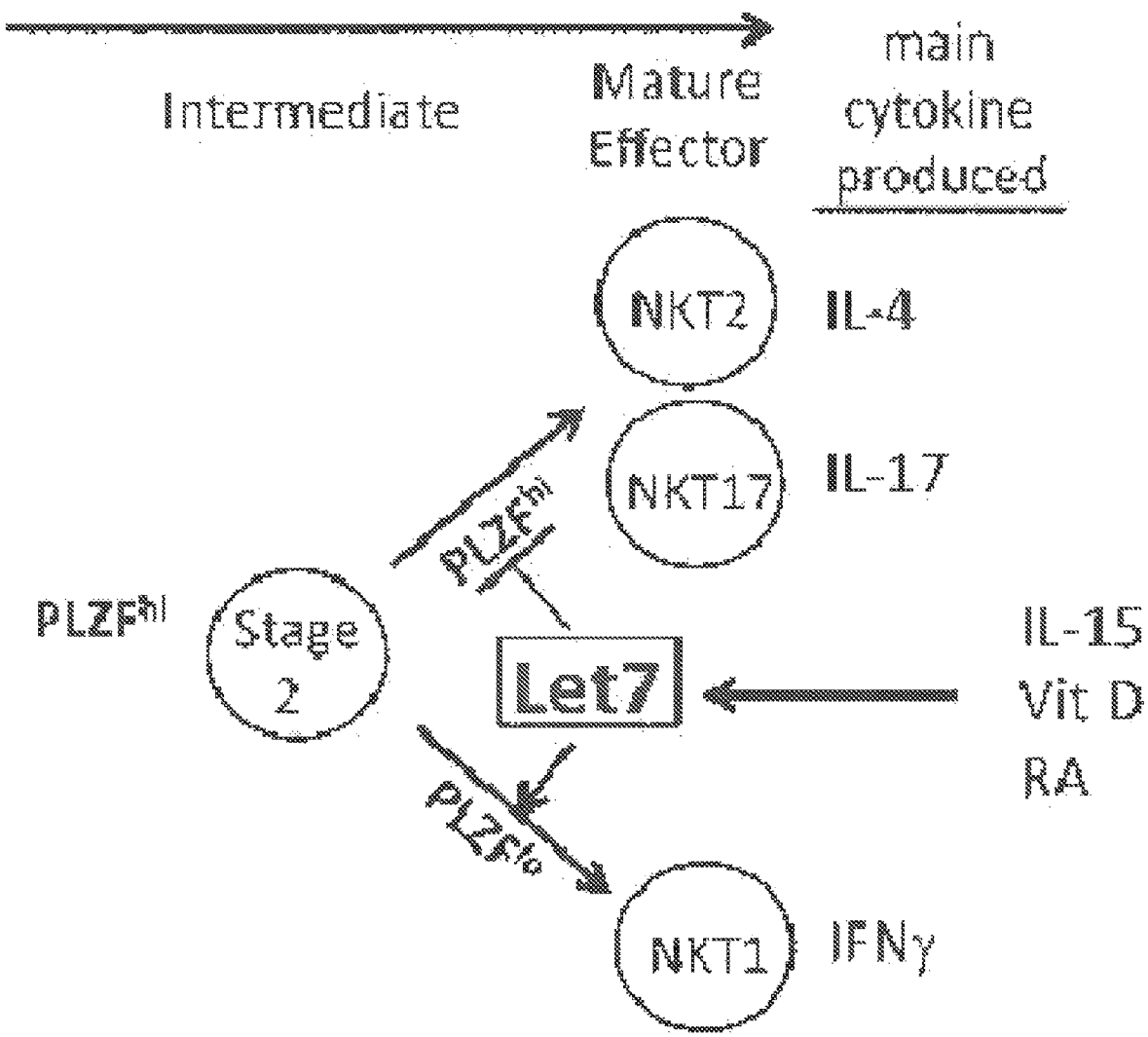
FIGS. 9A-C Role of let-7 microRNAs in the immune system. Let-7 controls differentiation of NKT cells (A). Loss of body weight in lymphopenic mice caused by injection of $CD4^+$ T cells isolated from wild-type (WT) and let-7 transgenic (Let-7TG) mice (B). Clinical score of EAE disease in wild-type (WT) and Let-7 transgenic (Let-7TG) animals.
Figure 9B:
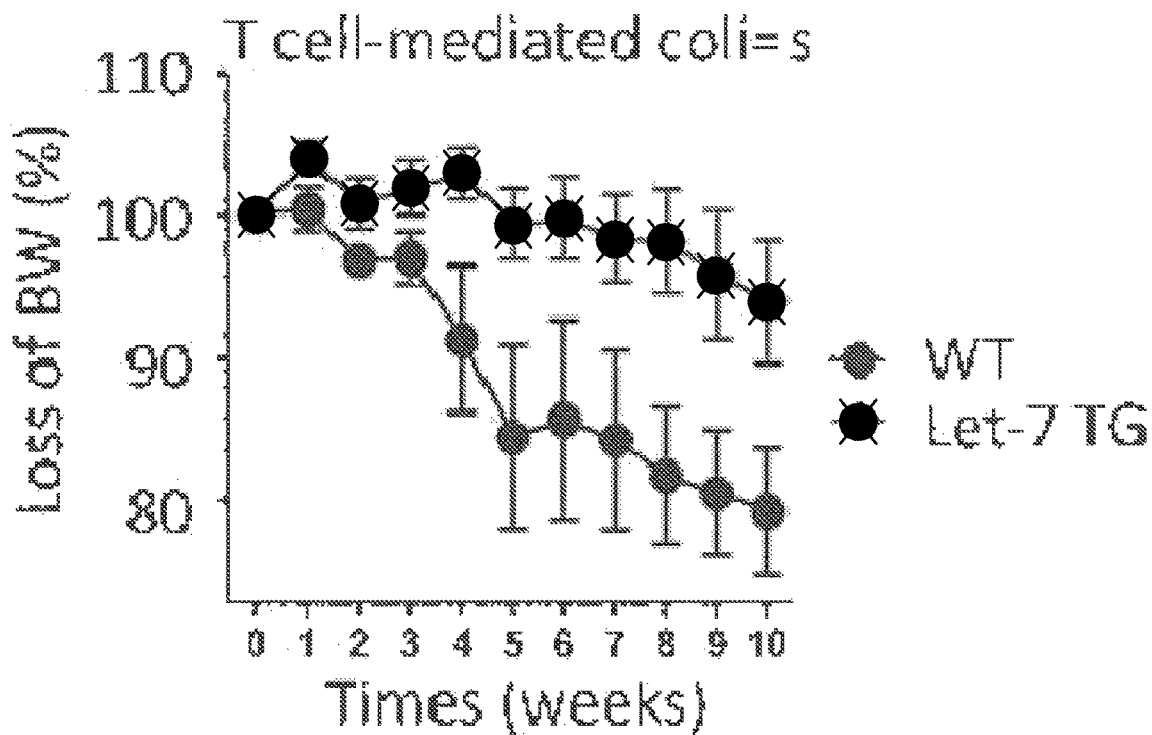
Figure 9C:
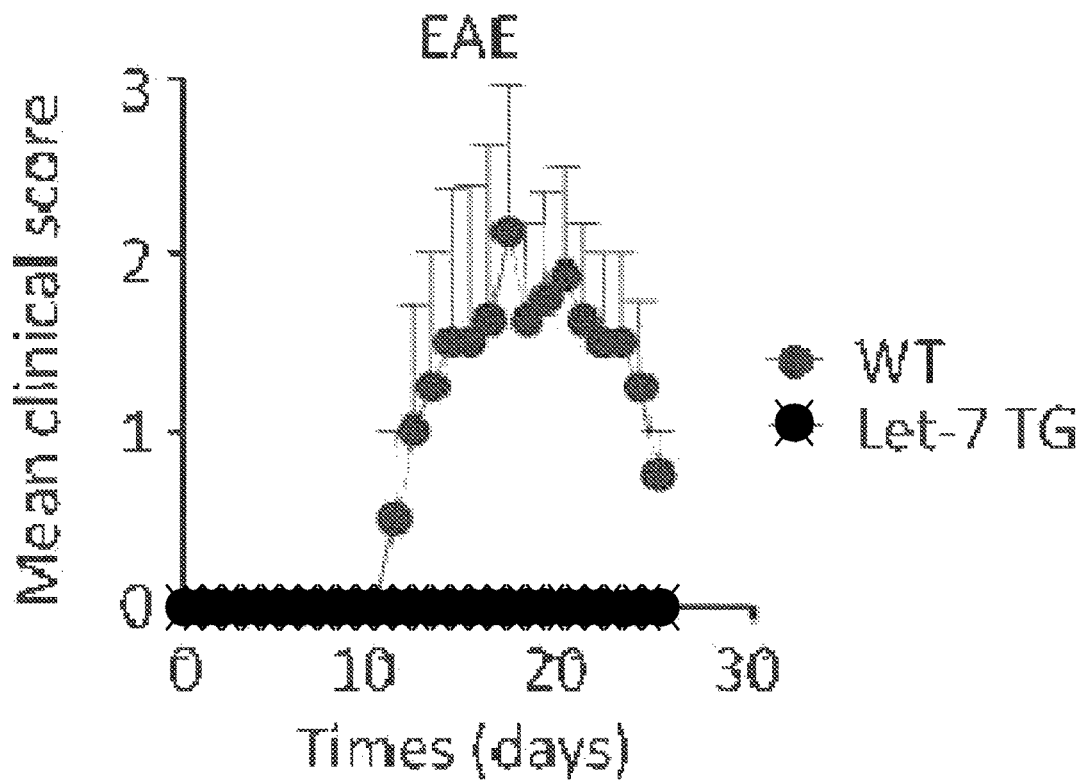

Based on the data it is believed that let-7 microRNA expression suppresses CTL responses. In addition, it has been demonstrated that the let-7 family of microRNAs plays a role in T cell lineage commitment, and in the differentiation of NKT cells3 (FIG. 9A). In line with other published results (15, 27), the data suggest that let-7 expression is also involved in CD4 T cell differentiation, and may have regulatory functions in autoimmune settings such as T cell-mediated colitis and EAE (experimental autoimmune encephalomyelitis) (FIG. 9B,C). Despite let-7 importance, the understanding of the mechanisms of let-7 expression in T lymphocytes is very limited (3).

It is believed that T cells possess specific mechanisms that control let-7 microRNA expression. By targeting these mechanisms, one will be able to directly suppress expression of let-7 microRNAs in CTLs, and consequently dramatically improve the anti-tumor-CTL responses. Two independent strategies have been chosen to investigate the regulation of let-7 in T cells. First, using in silico analysis one can predict and test transcription factors (TFs) that can potentially drive let-7 microRNA expression in T cells. Second, an unbiased genome-wide screen will be performed to identify novel mechanisms that directly control let-7 expression in T cells. Molecules identified from this screen that are predicted to be TFs will be the focus of further experiments.

TFs that control expression of let-7 genes using computational analysis. To enhance CTL function the upstream transcriptional mechanisms that regulate let-7 microRNA expression in T cells will be explored. TFs that have binding sites on let-7 promoters and regulatory elements will be predicted. Surprisingly, all let-7 genes in T cells responded to TCR stimulation by reducing their expression (FIG. 1). These data suggest that the expression of different let-7 microRNAs in T cells is regulated by the same molecular mechanism. Since there are so many paralogs of let-7 genes, the prediction analysis can be enhanced for conservation of TF binding sites both within and across species.

Figure 10A:
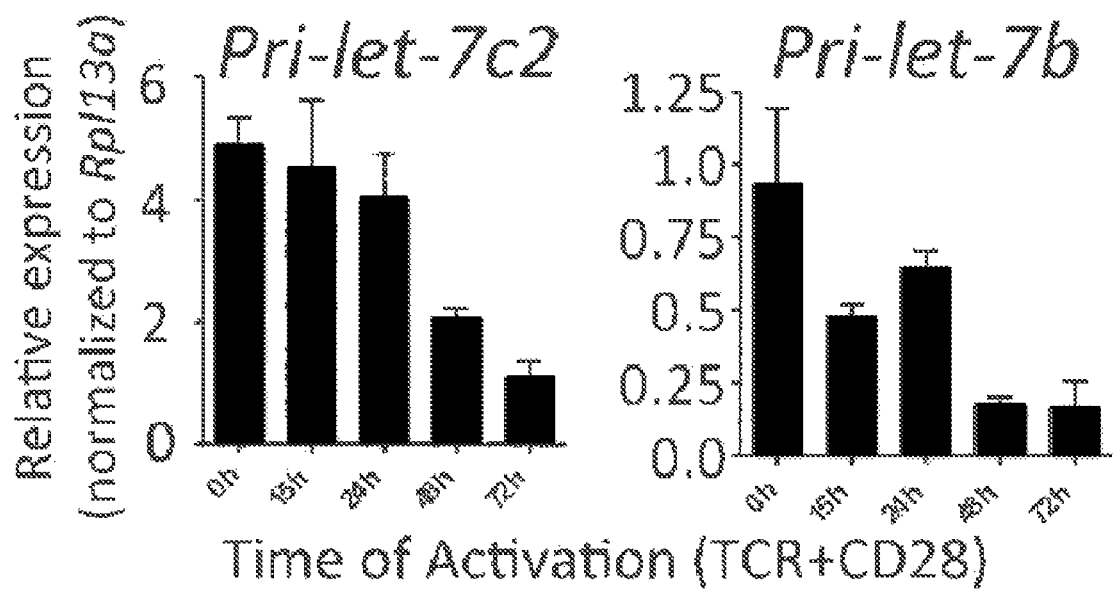
FIGS. 10A-C Analysis of transcriptional control of let-7 genes. Changes in pri-let-7 microRNAs expression in stimulated (anti-TCR and anti-CD28 mAbs) naïve $CD8^+$ T cells over time (A). Identification of CNS regions in the human let-7 locus on chromosome 9 based on degree of conservation between human and mouse genome (B). Results of ChIP-seq data analysis of predicted let-7 promoter (largest CNS region in this locus) using UCSC genome browser and data from ENCODE project (C).

The data suggest that expression of let-7 microRNAs is transcriptionally regulated through T cell receptor (TCR) signaling (FIG. 10A). Specifically, it was found that expression of the immature nuclear transcript of let-7 genes (pri-let-7) in CD8 T cells is reduced after TCR stimulation, which correlates with the loss of mature forms of let-7 (FIG. 2). Using computational analysis (VISTA browser and Genomatix software) 121 different let-7-associated conserved noncoding sequences (CNS) that are conserved between both humans and mice3 (FIG. 10OB) were identified.

Figures 10B, 10C:
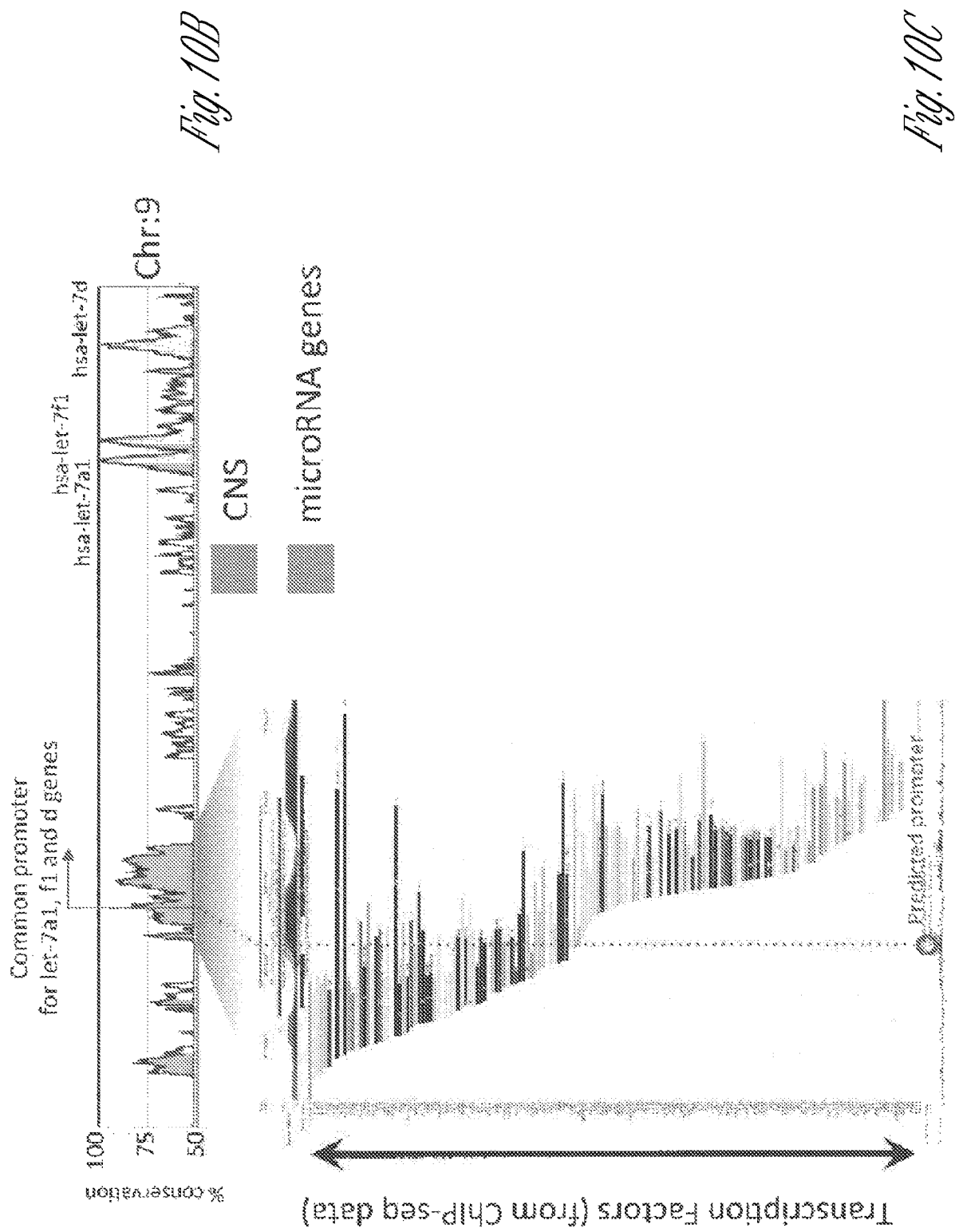

First, in order to find TFs that control expression of let-7 genes in T cells, T cell-specific regulatory elements in let-7 CNS will be identified by analyzing available ATAC-seq data sets for T cells. Next, to determine what factors bind to T cell-specific let-7 associated CNS a publically available database from the UCSC Genome Bioinformatics browser, with integrated results from The Factorbook of The Encyclopedia of DNA Elements (ENCODE) consortium will be utilized. Using this computational pipeline, ChIP-seq data for 161 currently available TFs in 91 cell types will be analyzed to identify occupancy regions for each factor and motif sites within the let-7 associated CNS (FIG. 10C). Using a similar approach the following TFs have been identified: STAT3, STAT5, VDR and RARA3. In addition, the available T cell-specific ChIP-seq data will be analyzed and overlaid. Furthermore, these results will be profiled using computational analysis of gene expression provided by the "Immunological Genome Project" online browser. This database will allow one to filter candidate TFs that are specifically expressed in T cells. Next, all TFs with binding sites that are common in the promoters and CNS of most let-7 genes will be selected, then the expression levels of the chosen TFs in CTLs by qPCR will be validated. Their role in the control of let-7 expression will be tested (discussed further below).

TFs that can potentially bind regulatory elements of let-7 genes will be predicted.

Figure 11:
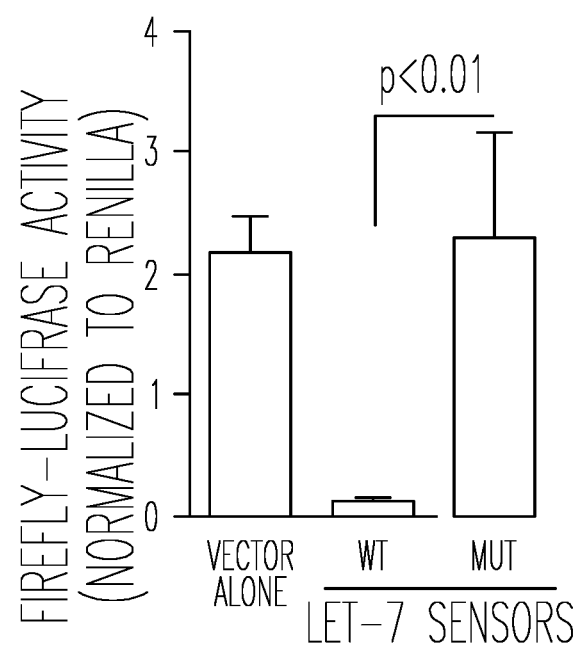
FIG. 11 Let-7 sensors. Luciferase reporter assay demonstrating targeting of the let-7b sensor that contains let-7 wild type or mutant binding site by endogenous let-7 microRNAs in NIH-3T3 cells transfected with firefly-luciferase reporter.

A genome-wide screen to identify mechanisms that regulate let-7 microRNA expression will be performed. Sensors to monitor let-7 activity in live cells were generated. These sensors contain the let-7 binding-sites downstream of a GFP or luciferase reporter (FIG. 11). A CRISPR-Cas9 genetic screen in Jurkat cells, a human T cell line that will be stably transfected with the let-7-GFP-sensors, will be employed. Due to let-7 expression, these cells will be GFP-negative/low. Next, the cells will be transduced with the lentiviral genome-scale CISPR/Cas9 knockout (GeCKO) library and subjected to a positive selection screen based on the level of GFP expression. Individual cells with increased GFP expression (indicating a reduction of let-7 expression) will be sorted, and targeted genes will be identified by deep sequencing. To achieve this goal the protocol described by the Zheng's laboratory (62) will be followed. Briefly, DNA will be extracted from the GFP-positive cells and subjected to a two-step PCR. The first PCR will be done to amplify lentiCRISPR sgRNAs. The second PCR will be performed to attach Illumina adapters, and to barcode samples. The product of the second PCR will be size selected using Ampure beads. Library quality will be assayed using a bioanalyzer, and libraries will be sequenced using the MiSeq (Illumina). Sequencing qualities will be assessed using Fastx. Sequences will be mapped to the hg38 genome using Bowtie, and hits mapped to genes using Cufflinks (63, 64) and the hg38.gtf file from the UCSC genome browser. Hits will be identified by comparing the distribution of sgRNAs before and after the positive GFP selection and candidate genes essential for let-7 expression will be identified by focusing on the sgRNAs whose frequency are significantly increased, with differential expression determined using edgeR65. To rank the top hits RNAi Gene Enrichment Ranking (RIGER) and/or Redundant siRNA Activity (RSA) algorithms will be used. Genes that are involved in the control of let-7 microRNA expression in T cells will be identified.

Validation of the regulation of let-7 transcription by the TFs obtained. Regulation of let-7 transcription by TFs obtained from in silico analyses (above) and from the CRISPER-Cas9 screen (above) will be validated by loss and gain of function experiments both in vitro and in vivo. Chromatin immunoprecipitation and promoter/enhancer-luciferase-reporter assays will be used to confirm the binding of identified TFs to let-7 microRNA genes. Next, using retroviral-based transduction of in vitro proliferating CTLs, the function of TFs that are responsible for let-7 expression in T cells will be assessed using loss (shRNA-mediated knockdown) and gain (cDNA overexpression) of function experiments. Furthermore, the anti-tumor response of these CTLs will be tested in vivo with the mouse tumor models described above. Briefly, P14+ T cells pre-activated in vitro will be transduced with shRNA-expressing retroviruses (shRNA-RV) or cDNA-expressing retroviruses to knockdown or overexpress the candidate TFs, respectively. For loss of function experiments, three shRNA-RV vectors, per every gene, containing a ZsGreen-reporter will be purchased from Transomic Technology. For gain of function experiments, cDNA will be synthesized and cloned into an IRES-GPF-containing retroviral vector. Retrovirally-transduced ZsGreen or GFP positive P14 blasts will be sorted and further expanded in the presence of IL-2. The changes in let-7 expression will be evaluated and TF-knockdown efficiency will be validated by qPCR and WB. Next, CD45.2+ reporter positive P14+ CTLs will be adoptively transferred into CD45.1+CD45.2+ mice bearing MCA-gp33-luc tumors for 5-10 days. The tumor regression will be surveyed by performing whole live animal bioluminescence imaging as described above. These independent approaches will identify endogenous mechanisms that control let-7 levels in CTLs, providing tools to enhance CTL-mediated immune responses.

shRNA-mediated knockdown of identified TFs in CTLs will lead to the loss of let-7 expression and consequently enhance the anti-tumor response, while cDNA-mediated overexpression of TFs will increase let-7 expression and suppress the immune response. Thus, the results from these experiments will identify molecular entities responsible for let-7 miroRNA expression providing novel therapeutic targets.

CONCLUSION

In addition to extending the knowledge of let-7 mediated molecular mechanisms in T cell biology, this technology will significantly improve anti-tumor CTL responses by genetically manipulating (suppressing) the levels of let-7 microRNAs in $CD8^+$ T lymphocytes. The experiments described herein define let-7 as a novel therapeutic target. Furthermore, the discovery of regulators of let-7 expression in T cells will provide information about new levels of regulation in the immune system and identify additional targets for manipulation of anti-cancer immune responses.

Additionally, as let-7 controls effector functions of T cells, then this provides implications for enhancing immune responses against pathogens or suppressing autoimmunity and preventing graft rejection.

BIBLIOGRAPHY

1. Sierra, R. A. et al. Rescue of notch-1 signaling in antigen-specific CD8+ T cells overcomes tumor-induced T-cell suppression and enhances immunotherapy in cancer. Cancer Immunol Res 2, 800-11 (2014).
2. Ji, Y. et al. miR-155 augments CD8+ T-cell antitumor activity in lymphoreplete hosts by enhancing responsiveness to homeostatic gammac cytokines. Proc Natl Acad Sci USA 112, 476-81 (2015).
3. Pobezinsky, L. A. et al. Let-7 microRNAs target the lineage-specific transcription factor PLZF to regulate terminal NKT cell differentiation and effector function. Nat Immunol 16, 517-24 (2015).
4. Chen, D. S. & Mellman, I. Oncology meets immunology: the cancer-immunity cycle. Immunity 39, 1-10 (2013).
5. Wolchok, J. D. & Chan, T. A. Cancer: Antitumour immunity gets a boost. Nature 515, 496-8 (2014).
6. Sharma, P. & Allison, J. P. The future of immune checkpoint therapy. Science 348, 56-61 (2015).
7. Morgan, R. A. et al. Cancer regression in patients after transfer of genetically engineered lymphocytes. Science 314, 126-9 (2006).
8. Rosenberg, S. A. & Restifo, N. P. Adoptive cell transfer as personalized immunotherapy for human cancer. Science 348, 62-8 (2015).
9. Parkhurst, M. R. et al. T cells targeting carcinoembryonic antigen can mediate regression of metastatic colorectal cancer but induce severe transient colitis. Mol Ther 19, 620-6 (2011).
10. Robbins, P. F. et al. Tumor regression in patients with metastatic synovial cell sarcoma and melanoma using genetically engineered lymphocytes reactive with NY-ESO-1. J Clin Oncol 29, 917-24 (2011).
11. Kalos, M. et al. T cells with chimeric antigen receptors have potent antitumor effects and can establish memory in patients with advanced leukemia. Sci Transl Med 3, 95ra73 (2011).
12. Brentjens, R. J. et al. CD19-targeted T cells rapidly induce molecular remissions in adults with chemotherapy-refractory acute lymphoblastic leukemia. Sci Transl Med 5, 177ra38 (2013).
13. Viswanathan, S. R. et al. Lin28 promotes transformation and is associated with advanced human malignancies. Nat Genet 41, 843-8 (2009).
14. Thornton, J. E. & Gregory, R. I. How does Lin28 let-7 control development and disease? Trends Cell Biol 22, 474-82 (2012).
15. Okoye, I. S. et al. MicroRNA-containing T-regulatory-cell-derived exosomes suppress pathogenic T helper 1 cells. Immunity 41, 89-103 (2014).
16. Heo, I. et al. Lin28 mediates the terminal uridylation of let-7 precursor MicroRNA. Mol Cell 32, 276-84 (2008).
17. Viswanathan, S. R., Daley, G. Q. & Gregory, R. I. Selective blockade of microRNA processing by Lin28. Science 320, 97-100 (2008).

18. Nam, Y., Chen, C., Gregory, R. I., Chou, J. J. & Sliz, P. Molecular basis for interaction of let-7 microRNAs with Lin28. Cell 147, 1080-91 (2011).
19. Piskounova, E. et al. Lin28A and Lin28B inhibit let-7 microRNA biogenesis by distinct mechanisms. Cell 147, 1066-79 (2011).
20. Zhu, H. et al. The Lin28/let-7 axis regulates glucose metabolism. Cell 147, 81-94 (2011).
21. Pearce, E. L. et al. Control of effector CD8+ T cell function by the transcription factor Eomesodermin. Science 302, 1041-3 (2003).
22. Barber, D. L., Wherry, E. J. & Ahmed, R. Cutting edge: rapid in vivo killing by memory CD8 T cells. J Immunol 171, 27-31 (2003).
23. Johnson, S. M. et al. RAS is regulated by the let-7 microRNA family. Cell 120, 635-47 (2005).
24. Johnson, C. D. et al. The let-7 microRNA represses cell proliferation pathways in human cells. Cancer Res 67, 7713-22 (2007).
25. Sampson, V. B. et al. MicroRNA let-7a down-regulates MYC and reverts MYC-induced growth in Burkitt lymphoma cells. Cancer Res 67, 9762-70 (2007).
26. Yuan, J., Nguyen, C. K., Liu, X., Kanellopoulou, C. & Muljo, S. A. Lin28b reprograms adult bone marrow hematopoietic progenitors to mediate fetal-like lymphopoiesis. Science 335, 1195-200 (2012).
27. Marcais, A. et al. microRNA-mediated regulation of mTOR complex components facilitates discrimination between activation and anergy in CD4 T cells. J Exp Med 211, 2281-95 (2014).
28. Logunova, N. N. et al. Restricted MHC-peptide repertoire predisposes to autoimmunity. J Exp Med 202, 73-84 (2005).
29. Pobezinsky, L. A. et al. Clonal deletion and the fate of autoreactive thymocytes that survive negative selection. Nat Immunol 13, 569-78 (2012).
30. Tai, X. et al. Basis of CTLA-4 function in regulatory and conventional CD4(+) T cells. Blood 119, 5155-63 (2012).
31. Kimura, M. Y. et al. IL-7 signaling must be intermittent, not continuous, during CD8(+) T cell homeostasis to promote cell survival instead of cell death. Nat Immunol 14, 143-51 (2013).
32. Katz, G. et al. T cell receptor stimulation impairs IL-7 receptor signaling by inducing expression of the microRNA miR-17 to target Janus kinase 1. Sci Signal 7, ra83 (2014).
33. Sukumar, M. et al. Inhibiting glycolytic metabolism enhances CD8+ T cell memory and antitumor function. J Clin Invest 123, 4479-88 (2013).
34. Ji, Y. & Gattinoni, L. miR-155 releases the brakes on antitumor T cells. Oncoimmunology 4, e1026533 (2015).
35. Weinreich, M. A., Odumade, O. A., Jameson, S. C. & Hogquist, K. A. T cells expressing the transcription factor PLZF regulate the development of memory-like CD8+ T cells. Nat Immunol 11, 709-16 (2010).
36. Prevost-Blondel, A. et al. Tumor-infiltrating lymphocytes exhibiting high ex vivo cytolytic activity fail to prevent murine melanoma tumor growth in vivo. J Immunol 161, 2187-94 (1998).
37. Rabinovich, B. A. et al. Visualizing fewer than 10 mouse T cells with an enhanced firefly luciferase in immunocompetent mouse models of cancer. Proc Natl Acad Sci USA 105, 14342-6 (2008).
38. Joyce, J. A. & Fearon, D. T. T cell exclusion, immune privilege, and the tumor microenvironment. Science 348, 74-80 (2015).
39. Gabrilovich, D. I., Ostrand-Rosenberg, S. & Bronte, V. Coordinated regulation of myeloid cells by tumours. Nat Rev Immunol 12, 253-68 (2012).
40. Arina, A. & Bronte, V. Myeloid-derived suppressor cell impact on endogenous and adoptively transferred T cells. Curr Opin Immunol 33, 120-5 (2015).
41. Savage, P. A., Malchow, S. & Leventhal, D. S. Basic principles of tumor-associated regulatory T cell biology. Trends Immunol 34, 33-40 (2013).
42. Ghiringhelli, F. et al. Tumor cells convert immature myeloid dendritic cells into TGF-beta-secreting cells inducing CD4+CD25+ regulatory T cell proliferation. J Exp Med 202, 919-29 (2005).
43. Lesokhin, A. M. et al. Monocytic CCR2(+) myeloid-derived suppressor cells promote immune escape by limiting activated CD8 T-cell infiltration into the tumor microenvironment. Cancer Res 72, 876-86 (2012).
44. Weiss, J. M. et al. Neuropilin 1 is expressed on thymus-derived natural regulatory T cells, but not mucosa-generated induced Foxp3+ T reg cells. J Exp Med 209, 1723-42, S1 (2012).
45. Sonda, N. et al. miR-142-3p prevents macrophage differentiation during cancer-induced myelopoiesis. Immunity 38, 1236-49 (2013).
46. Parker, K. H. et al. HMGB1 enhances immune suppression by facilitating the differentiation and suppressive activity of myeloid-derived suppressor cells. Cancer Res 74, 5723-33 (2014).
47. Ries, C. H. et al. Targeting tumor-associated macrophages with anti-CSF-1R antibody reveals a strategy for cancer therapy. Cancer Cell 25, 846-59 (2014).
48. Pardoll, D. M. The blockade of immune checkpoints in cancer immunotherapy. Nat Rev Cancer 12, 252-64 (2012).
49. Twyman-Saint Victor, C. et al. Radiation and dual checkpoint blockade activate non-redundant immune mechanisms in cancer. Nature 520, 373-7 (2015).
50. Freeman, G. J. et al. Engagement of the PD-1 immunoinhibitory receptor by a novel B7 family member leads to negative regulation of lymphocyte activation. J Exp Med 192, 1027-34 (2000).
51. Keir, M. E., Butte, M. J., Freeman, G. J. & Sharpe, A. H. PD-1 and its ligands in tolerance and immunity. Annu Rev Immunol 26, 677-704 (2008).
52. Maekawa, Y. et al. Notch2 integrates signaling by the transcription factors RBP-J and CREB1 to promote T cell cytotoxicity. Nat Immunol 9, 1140-7 (2008).
53. Matter, M. et al. Decreased tumor surveillance after adoptive T-cell therapy. Cancer Res 67, 7467-76 (2007).
54. Sadelain, M., Brentjens, R. & Riviere, I. The promise and potential pitfalls of chimeric antigen receptors. Curr Opin Immunol 21, 215-23 (2009).
55. Jena, B., Dotti, G. & Cooper, L. J. Redirecting T-cell specificity by introducing a tumor-specific chimeric antigen receptor. Blood 116, 1035-44 (2010).
56. Intlekofer, A. M. et al. Effector and memory CD8+ T cell fate coupled by T-bet and eomesodermin. Nat Immunol 6, 1236-44 (2005).
57. Zhou, X. et al. Differentiation and persistence of memory CD8(+) T cells depend on T cell factor 1. Immunity 33, 229-40 (2010).
58. Sallusto, F., Geginat, J. & Lanzavecchia, A. Central memory and effector memory T cell subsets: function, generation, and maintenance. Annu Rev Immunol 22, 745-63 (2004).

59. Gattinoni, L. et al. Wnt signaling arrests effector T cell differentiation and generates CD8+ memory stem cells. Nat Med 15, 808-13 (2009).
60. Klebanoff, C. A. et al. Central memory self/tumor-reactive CD8+ T cells confer superior antitumor immunity compared with effector memory T cells. Proc Natl Acad Sci USA 102, 9571-6 (2005).
61. Overwijk, W. W. et al. Tumor regression and autoimmunity after reversal of a functionally tolerant state of self-reactive CD8+ T cells. J Exp Med 198, 569-80 (2003).
62. Shalem, O. et al. Genome-scale CRISPR-Cas9 knockout screening in human cells. Science 343, 84-7 (2014).
63. Langmead, B., Trapnell, C., Pop, M. & Salzberg, S. L. Ultrafast and memory-efficient alignment of short DNA sequences to the human genome. Genome Biol 10, R25 (2009).
64. Trapnell, C. et al. Differential gene and transcript expression analysis of RNA-seq experiments with TopHat and Cufflinks. Nat Protoc 7, 562-78 (2012).
65. Robinson, M. D., McCarthy, D. J. & Smyth, G. K. edgeR: a Bioconductor package for differential expression analysis of digital gene expression data. Bioinformatics 26, 139-40 (2010).
66. Ha, M. & Kim, V. N. Regulation of microRNA biogenesis. Nat Rev Mol Cell Biol 15, 509-24 (2014).
67. Mehrotra, S. et al. A coreceptor-independent transgenic human TCR mediates anti-tumor and anti-self-immunity in mice. J Immunol 189, 1627-38 (2012).

Example 3—Modulation of Let-7 miRNAs Controls the Differentiation of Effector CD8 T Cells Through Regulation of Myc and Eomesodermin Abstract The differentiation of naïve CD8 T cells into effector cytotoxic T lymphocytes upon antigen stimulation is necessary for successful anti-viral, and anti-tumor immune responses. Herein a dual role for the let-7 microRNAs in the regulation of CD8 T cell responses is described, where maintenance of the quiescent phenotype in naïve CD8 T cells requires high levels of let-7 expression, while generation of cytotoxic T lymphocytes depends upon T cell receptor mediated let-7 downregulation. Decrease of let-7 expression in activated T cells enhances clonal expansion, metabolic reprogramming, and acquisition of effector function through derepression of the let-7 targets, Myc and Eomesodermin. Ultimately, let-7 microRNAs has been identified as a novel molecular transmitter of TCR signaling, which controls the magnitude of CD8 T cell-mediated immunity.

INTRODUCTION

CD8+ T cells are responsible for the rapid clearance of virally infected, and cancerous cells in the organism. Prior to encounter with antigen, naïve CD8 T cells exhibit a quiescent state that is characterized by very low rates of proliferation, and a "quiet" transcriptional landscape with no expression of any effector molecules. After antigen recognition, activated CD8 T cells undergo blastogenesis and rapid clonal expansion, which is followed by differentiation into effector cytotoxic T lymphocytes (CTLs), and memory T cells that are both capable of producing effector cytokines and killing target cells. These changes in T cells are accompanied by metabolic reprograming from oxidative phosphorylation to aerobic glycolysis that provides energy and larger amounts of the biomacromolecular intermediates needed to support growth (1).

The productive differentiation of CD8 T cells requires three definitive signals; one is from the T cell receptor (TCR) during antigen recognition, the second is from costimulation, and the third is due to cytokines. It has been extensively studied how these signals execute the CD8 T cell differentiation program by activation of a complex network of transcription factors such as Myc, Notch-1, Tbet, Eomes, Blimp-1, Zbtb32, Runx3, and Zeb2 (2-5). However, the global regulation of these processes is not yet fully understood.

Post-transcriptional regulatory mechanisms provide broad regulation of gene expression. The most efficient post-transcriptional regulatory machinery involves RNA interference mediated by microRNAs (miRNAs), small non-coding RNAs that target mRNA in a sequence-specific manner to prevent protein synthesis, and the expression of which is both inducible, and tissue-specific (6-7). The importance of this type of regulation for T cells was first demonstrated through the ectopic expression of various miRNAs during hematopoiesis (8). Later, it was found that miRNA depletion achieved by a T cell-specific deletion of Dicer, an enzyme involved in the biogenesis of mature miRNAs, resulted in severe defects, including aberrant proliferation, differentiation, and function of T lymphocytes (9-11). Further research corroborated these earlier studies, identifying the role of specific miRNAs in these processes. MiR-181 was shown to modulate TCR sensitivity and signal strength in developing and mature T cells (12-13). In CD4 T cells, miR-29 was shown to control the T helper response through the direct targeting of IFN-γ mRNA (14), as well as the transcription factors T-bet and Eomes (15). In CD8 T cells, the upregulation of miR-130/301 (16) and the miR-17-92 cluster (15, 17, 18) was demonstrated to be needed for the initiation of differentiation upon antigen stimulation.

Let-7 miRNAs are the largest and most abundant family of miRNAs in lymphocytes, yet very little is known about their function. It has been shown that let-7 miRNAs are needed for the differentiation and function of natural killer T cells, an innate-like subset of T cells (19-20). It has also been suggested that let-7 miRNAs may regulate T helper responses (21-22) and play a role in the suppressive function of Tregs (23). However, the extent to which let-7 miRNAs regulate the differentiation or function of CD8 T cells has yet to be explored.

Provided herein is the examination of the role of let-7 miRNA expression in naïve and differentiating CD8 T cells. It was found that in naïve CD8 T cells high levels of let-7 miRNAs are necessary to maintain the quiescent state of cells, while TCR-mediated down-regulation of let-7 levels in activated cells is needed for the effective differentiation and function of CTLs. In fact, experimentally forced let-7 expression severely impairs the proliferation and differentiation of CD8 T cells, while let-7 deficiency significantly enhances the cytotoxic function of CTLs and consequently immune responses in vivo. Given these findings, a model is proposed in which let-7 acts as a molecular hub by converting the strength of TCR signaling into the strength of CD8 T cell function.

Materials and Methods

Animals

C57BL/6J (CD45.2$^+$ wild type, stock no. 000664), B6.SJL-PtprcaPepcb/BoyJ (CD45.1$^+$ wild type, stock no. 002014), B6(Cg)- Rag2$^{Tm1.1Cgmn}$J (Rag2$^{-/-}$, stock no.

008449), B6 Tg(CD4-cre)1Cwi/BfluJ (CD4-Cre, stock no. 017336), and B6.129S1 (Cg)-Eome$^{stm1.1Bflu}$/J (Eomes$^{fl/fl}$, stock no. 017293) were obtained from the Jackson Laboratory. B6.Cg-CollA1$^{tm3(tetO-Mirlet7g/Mir21)Gqda}$/J (let-7g, stock no. 023912) and B6.Cg-Gt(ROSA)26 Sor$^{tm1(rtTA*M2)Jae}$/J (M2rtTA, stock no. 006965) were also obtained from the Jackson Laboratory and subsequently crossed to generate let-7 Tg mice. Mice with the Lin28B transgene (Lin28Tg) driven under the control of the human CD2 promoter (19), and B6 Tg(TcrLCMV)327Sdz/JDvs/J (P14) mice were a generous gift from Alfred Singer (NCI, NIH). P14$^+$ mice, and wild type C57Bl/6J mice on a Rag2$^{-/-}$ background were crossed to generate wild type P14 mice. let-7 Tg mice, and P14$^+$ mice were crossed on a Rag2$^{-/-}$ background to generate P14 doxycycline-inducible let-7 transgenic mice. Lin28B Tg mice were crossed with P14+ mice on a Rag2$^{-/-}$ background to generate P14 let-7 deficient mice. let-7 Tg, Lin28B Tg, P14$^+$ mice were crossed on a Rag2$^-$ background to generate 4Tg mice. CD4-Cre and Eomes$^{fl/fl}$ mice were crossed to generate mice with a T cell-specific conditional knockout of Eomes. CD4-Cre, Eomes$^{fl/fl}$ Lin28B Tg, P14$^+$ mice were crossed to generate let-7 deficient mice with a T cellspecific deletion of Eomes. Doxycycline-mediated induction of let-7 transgene expression Mice were fed with 2 mg/mL doxycycline in drinking water supplemented with 10 mg/mL sucrose. In vitro, lymphocytes were cultured with 2 μg/mL doxycycline in CTL culture media (see cell sorting and in vitro culture below).

Flow Cytometry Analysis

For in vitro differentiation studies, 2×10$^6$ cells were stimulated with phorbol myristate acetate (PMA) and Ionomycin for 4 h at 37° C. and Monensin A for 2 h at 37° C. Cells were first stained for surface proteins then fixed, permeablized, and stained for intracellular proteins according to the manufacturer's instructions (BD Pharmingen, eBio). Flow cytometry data were acquired on a BD Fortessa or a MilliPore Amnis ImageStream. The following monoclonal antibodies were used: CD8α (53-6.7, eBioscience; CT-CD8α, Invitrogen), CD8β (YTS156.7.7, BioLegend), CD4 (RM4-5, BioLegend), CD44 (IM7, BD Pharmingen), CD25 (PC61, BioLegend; PC61.5 eBioscience), CD122 (TM-β1, BioLegend), Granzyme A (3G8.5 BioLegend; eBioscience), Granzyme B (GB 11, BioLegend), IFN-γ (XMG1.2, eBioscience), Eomes (Dan 1 1mag, eBioscience), Ki67 (SolA15, eBioscience), T-bet (04-46, BD Pharmingen), PE-Streptavadin (BioLegend).

For LCMV studies, 2×10$^6$ cells were stimulated for 4 hr at 37° C. with 2 μg/mL of GP33-41 or NP396-404 peptides, and 1 μl/mL GolgiPlug (BD Pharmingen). Cells were first stained for surface proteins then fixed, permeablized, and stained for intracellular proteins according to the manufacturer's instructions (BD Pharmingen). The following monoclonal antibodies were used: CD8β (YTS156.7.7; BioLegend), CD45.1 (A20; BD Pharmingen), CD45.2 (104; BD Pharmingen), KLRG1 (2F1; BD Pharmingen), CD44 (IM7; BD Pharmingen), TNF-α (MP6-XT22; BD Pharmingen), IFN-γ (XMG1.2; BD Pharmingen). Flow cytometry data were acquired on a BD LSR II. All flow cytometry data was analyzed with FlowJo software (TreeStar). MilliPore Amnis ImageStream data was analyzed with IDEAS software (EMD Millipore).

Cell Sorting and In Vitro Culture

Lymph nodes were harvested and gently tweezed to remove lymphocytes. CD8 lymph node T cells were enriched for via antibody-mediated depletion of B cells using magnetic beads (Qiagen). CD4 T cells were removed via magnetic beads (BioMag, Qiagen) following incubation with anti-mouse CD4 antibodies conjugated with Rat IgG (GK1.5). Lymphocytes were electronically sorted for the further purification of naïve CD8 T cells (CD44$^{lo}$ CD25$^{lo}$CD8$^+$CD4$^-$).

Cells were stimulated either with irradiated splenocytes loaded with anti-CD3 (10 μg/mL), or plate-bound H57 (10 μg/mL) and anti-CD28 (5 μg/mL), then differentiated for five days in RPMI supplemented with 10% fetal bovine serum, 1% HEPES, 1% sodium pyruvate, 1% penicillin/ streptomycin, 1% L-glutamine, 1% non-essential amino acids, 0.3% β-mercaptoethanol, 100 U/mL IL-2, 100 mg/mL gentamicin, and 2 μg/mL doxycycline when necessary.

Prediction of miRNA Targets

Eomes was independently identified in an unbiased search of all ORFs in the mouse and humans genomes, for matches to an extended 9 bp let-7 seed, "TACTACCTC". This search utilized a hashing algorithm as described in 76 and identified 119 genes in the mouse genome, and 159 genes in the human genome that have one or more matches to the 9 bp let-7 seed in their ORF sequences. Interestingly, humans have three splice variants of Eomes, one of which lacks the exon containing the match to let-7, thus opening the possibility that Eomnes may escape let-7 repression in some cells by alternative splicing of the target sequence. This may require further investigation.

Luciferase Assay

NIH 3T3 cells were transfected with the pmirGLO vector (Promega) containing either the intact let-7 binding motif from Eomes, or a mutated version of this binding motif, or either intact antisense or mutated antisense seed regions of let-7b, let-7g, or let-7i using Lipofectamine and Plus reagent (Invitrogen). Luciferase activity was measured 48 hours later on a POLARstar Omega 96-well plate reader (BMG Labtech), using the Dual-Luciferase Reporter Assay System (Promega).

CellTrace Violet Proliferation Assay

Electronically sorted naïve CD8 T cells were stained with CellTrace Violet (Invitrogen) for 15 minutes at 37° C. Cells were stimulated using plate-bound H57 (10 μg/mL) and anti-CD28 (5 μg/mL), cultured for 72 hours, and analyzed by flow cytometry.

CellTrace Violet Cytotoxicity Assay

P14+ CD8 T cells were stimulated with H57 (10 μg/mL) and anti-CD28 (5 μg/mL) platebound antibodies, differentiated into CTLs for 5 days in the presence of IL-2, gentamicin, and 2 μg/mL doxycycline when appropriate. On day 5, live splenocytes were warmed for 10 minutes at 37° C., then stained with CellTrace Violet (Invitrogen) at two different concentrations (CTV$^{high}$ or CTV$^{low}$) for 15 minutes at 37° C. CTV$^{low}$ splenocytes were then loaded with either LCMV gp33-41 peptide (1 μM, GenScript) or LCMV np396-404 peptide (1 μM, GenScript) for 1 hour at 37° C., and are referred to below as "live experimental splenocytes". CTV$^{high}$ splenocytes remained peptide-free, and were used as a reference control, referred to below as "live control splenocytes". Equal amounts of both live experimental splenocytes and live control splenocytes were co-cultured with CTLs at different ratios for four to five hours. Cytotoxicity was assessed by flow cytometry.

Measured as the percent target lysis of live experimental splenocytes loaded with either target (gp33-41) or control (np396-404) peptide from the lymphocytic choriomeningitis virus. The following formula was used to calculate the percent target lysis:

$$\left(1-\left(\frac{A}{B}\times\frac{C}{D}\right)\right)\times 100$$

A—frequency of live experimental splenocytes co-cultured with CTLs; B—frequency of live control splenocytes co-cultured with CTLs; C—frequency of live control splenocytes incubated in the absence of CTLs; D—frequency of live experimental splenocytes incubated in the absence of CTLs. Lymphocytic choriomeningitis virus infection and T cell adoptive transfer $10\times10^3$ CD45.2+ donor cells were transferred i.v. into CD45.1+ congenic hosts. Mice were inoculated with $5\times10^4$ p.f.u. of LCMV Armstrong i.p. Spleens were harvested and processed 7 days post-infection.

Isolation of RNA and Quantitative PCR

RNA was isolated according to the manufacturer's instructions (QIAGEN miRNeasy), and genomic DNA removed using the DNA-free DNA removal kit (Ambion). mRNA encoding cDNA was synthesized using the SuperScript III Reverse Transcriptase kit (Invitrogen), while miRNA-encoding cDNA was synthesized using the Taqman MicroRNA Reverse Transcription kit (Applied Biosystems). SYBR Green quantitative PCR was performed using the Bioline SensiFAST SYBR Lo-Rox kit and Taqman quantitative PCR was performed using the Bioline SensiFAST Lo-Rox kit. Both SYBR Green and Taqman amplification primers (Integrated DNA Technologies, or Applied Biosystems) are listed in Table 1.

TABLE 1

| SYBR primers | Forward (5'-3') | Reverse (5'-3') |
|---|---|---|
| Cdc25a | ACAGCAGTCTACAGAGAATGGG (SEQ ID NO: 19) | GATGAGGTGAAAGGTGTCTTGG (SEQ ID NO: 36) |
| Ccnd2 | GAGTGGGAACTGGTAGTGTTG (SEQ ID NO: 20) | CGCACAGAGCGATGAAGGT (SEQ ID NO: 37) |
| Ccnf | GTAGGCGATAGGTCATACGGA (SEQ ID NO: 21) | ACAATGGATCACTACCCCGTG (SEQ ID NO: 38) |
| Cdk6 | GGCGTACCCACAGAAACCATA (SEQ ID NO: 22) | AGGTAAGGGCCATCTGAAAACT (SEQ ID NO: 39) |
| Glut1 | CAGTTCGGCTATAACACTGGTG (SEQ ID NO: 23) | GCCCCCGACAGAGAAGATG (SEQ ID NO: 40) |
| Glut3 | ATGGGGACAACGAAGGTGAC (SEQ ID NO: 24) | GTCTCAGGTGCATTGATGACTC (SEQ ID NO: 41) |
| Gpd2 | GAAGGGGACTATTCTTGTGGGT (SEQ ID NO: 25) | GGATGTCAAATTCGGGTGTGT (SEQ ID NO: 42) |
| Pfk1 | GGAGGCGAGAACATCAAGCC (SEQ ID NO: 26) | CGGCCTTCCCTCGTAGTGA (SEQ ID NO: 43) |
| Hk2 | TGATCGCCTGCTTATTCACGG (SEQ ID NO: 27) | AACCGCCTAGAAATCTCCAGA (SEQ ID NO: 44) |
| Tpi | CCAGGAAGTTCTTCGTTGGGG (SEQ ID NO: 28) | CAAAGTCGATGTAAGCGGTGG (SEQ ID NO: 45) |
| Pkm | GCCGCCTGGACATTGACTC (SEQ ID NO: 29) | CCATGAGAGAAATTCAGCCGAG (SEQ ID NO: 46) |
| Myc | AGTGCTGCATGAGGAGACAC (SEQ ID NO: 30) | GGTTTGCCTCTTCTCCACAG (SEQ ID NO: 47) |
| Tfap4 | GGAGAAGCTAGAGCGGGAAC (SEQ ID NO: 33) | TTTTGCCGGGATGTAGAGAC (SEQ ID NO: 48) |
| Zbtb32 | CCCACTCCAGGATCTTTTCCC (SEQ ID NO: 32) | TGACTCACACAGGTTGCCAG (SEQ ID NO: 49) |
| Prdm1 | GACGGGGGTACTTCTGTTCA (SEQ ID NO: 33) | GGCATTCTTGGGAACTGTGT (SEQ ID NO: 50) |
| Runx3d | GCGACATGCCTTCCAACAGC (SEQ ID NO: 34) | CTTAGCGCGCCGCTGTTCTCGC (SEQ ID NO: 51) |
| RPL13a | CGAGGCATGCTGCCCCACAA (SEQ ID NO: 35) | AGCAGGGACCACCATCCGCT (SEQ ID NO: 52) |
| AB Taqman Assay | | |
| Hes1 | Mm01342805_m1 | |
| Hey1 | Mm00468865_m1 | |
| Hey1 | Mm00516558_m1 | |
| Dtx1 | Mm00492297_m1 | |
| Ldha | Mm01612132_g1 | |
| Yars | Mm00480301_m1 | |
| let-7a | 377 | |
| let-7b | 378 | |
| let-7c | 379 | |
| let-7d | 2283 | |
| let-7e | 2406 | |
| let-7f | 382 | |
| let-7g | 2282 | |
| let-7i | 2221 | |
| U6 | 1973 | |
| IDT Taq Assay | | |
| Eomes | Mm.PT.58. 32833544 | |
| Tbx21 | Mm.PT.58. 5261453 | |
| Gzma | Mm.PT.58. 43238753 | |

TABLE 1-continued

| | |
|---|---|
| Gmzb | Mm.PT.58. 42155916 |
| Ifng | Mm.PT.58. 30096391 |
| Prf1 | Mm.PT.58. 41904164 |
| Rpl13a | Mm.PT.58. 43547045.g |

Tumor Transplantation

For P815 (ATCC) survival studies, 30×10$^6$ tumor cells were injected i.p. into host mice. For P815 tumor burden studies, 20×10$^6$ tumor cells were injected i.p. into host mice. Seven days post-injection, tumor burden was assessed by washing the peritoneum with PBS and counting the collected cells. Mice were fed with doxycycline for the duration of the study.

Statistical Analysis

P values were determined using a two-tailed Student's t-test.

Results let-7 miRNA expression maintains the quiescent state in naïve CD8 T cells.

Figure 12A:
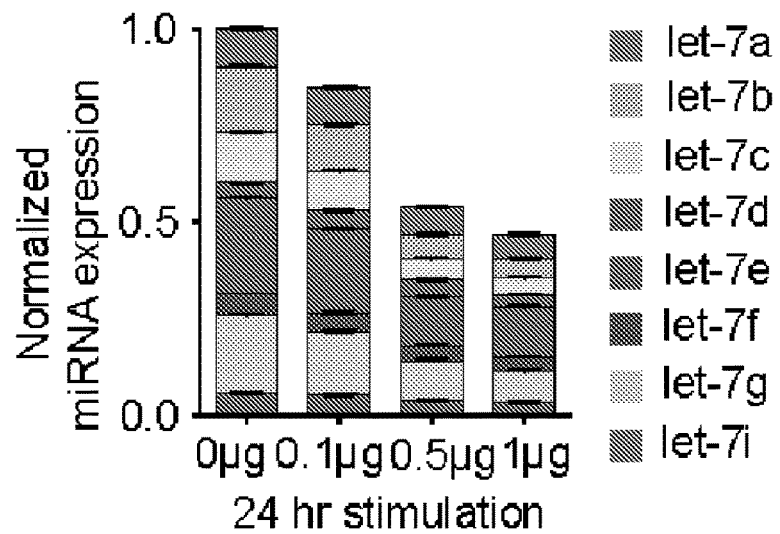
FIGS. 12A-D let-7 expression is necessary and sufficient to maintain the quiescent phenotype of CD8 T cells prior to TCR stimulation. (a) Quantitative RT-PCR analysis of individual let-7 miRNAs in naïve CD8 T cells stimulated with plate-bound anti-TCR (µg as indicated) and anti-CD28 (5 µg) for 24 hours, presented relative to results obtained for the small nuclear RNA (U6 control) and normalized to the unstimulated (0 µg) sample. (b) Quantitative RT-PCR analysis of individual let-7 miRNAs in naïve CD8 T cells stimulated with plate-bound anti-TCR (5 µg) and anti-CD28 (5 µg) over increasing periods of time as indicated, presented relative to results obtained for the small nuclear RNA (U6 control) and normalized to the unstimulated (0 h) sample. (c) Size analysis based on FSC (forward scatter) of naïve CD8 T cells from the spleens and lymph nodes of P14+ wild type and P14+ Lin28 Tg mice, both on Rag2$^{-/-}$ background, normalized to wild type. (d) Expression of Ki67 in naïve CD8 T cells from spleens and lymph nodes of P14$^+$ wild type and P14$^+$ Lin28 Tg mice, both on Rag2$^{-/-}$ background. *** $P<0.001$, compared with wild type using two tailed Student's t-test. Data are one experiment (a; mean and s.e.m. of technical triplicates) or one experiment representative of three independent experiments (b, c, d; mean and s.e.m. of three experiments).
Figure 12B:
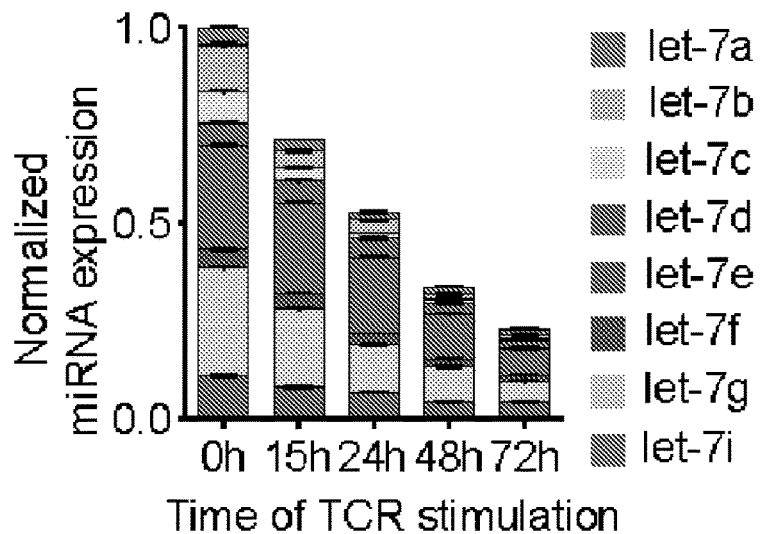

To explore the potential regulatory role of let-7 miRNAs in CD8 T cells, the expression levels of let-7 miRNA family members in naïve and activated CD8 T cells were determined. Surprisingly, the initially very high expression of let-7 miRNAs in naïve CD8 T cells was reduced by TCR signaling, and this downregulation was proportional to the strength and duration of TCR-stimulation (FIG. 12A, B). These results suggest that TCR-mediated signaling inhibits the expression of let-7 miRNAs during T cell activation.

Figure 12C:
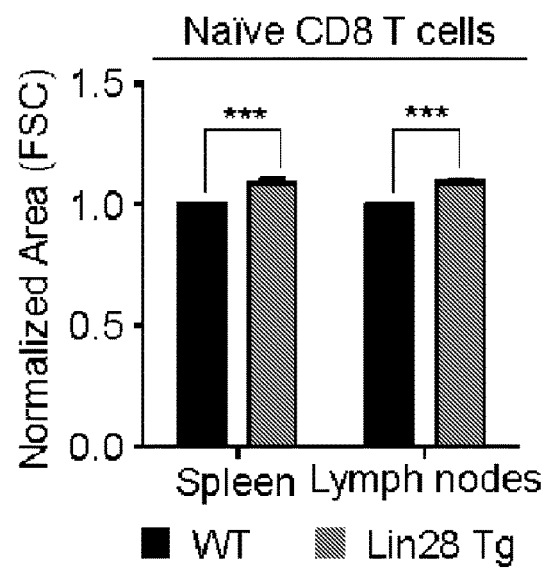
Figure 12D:
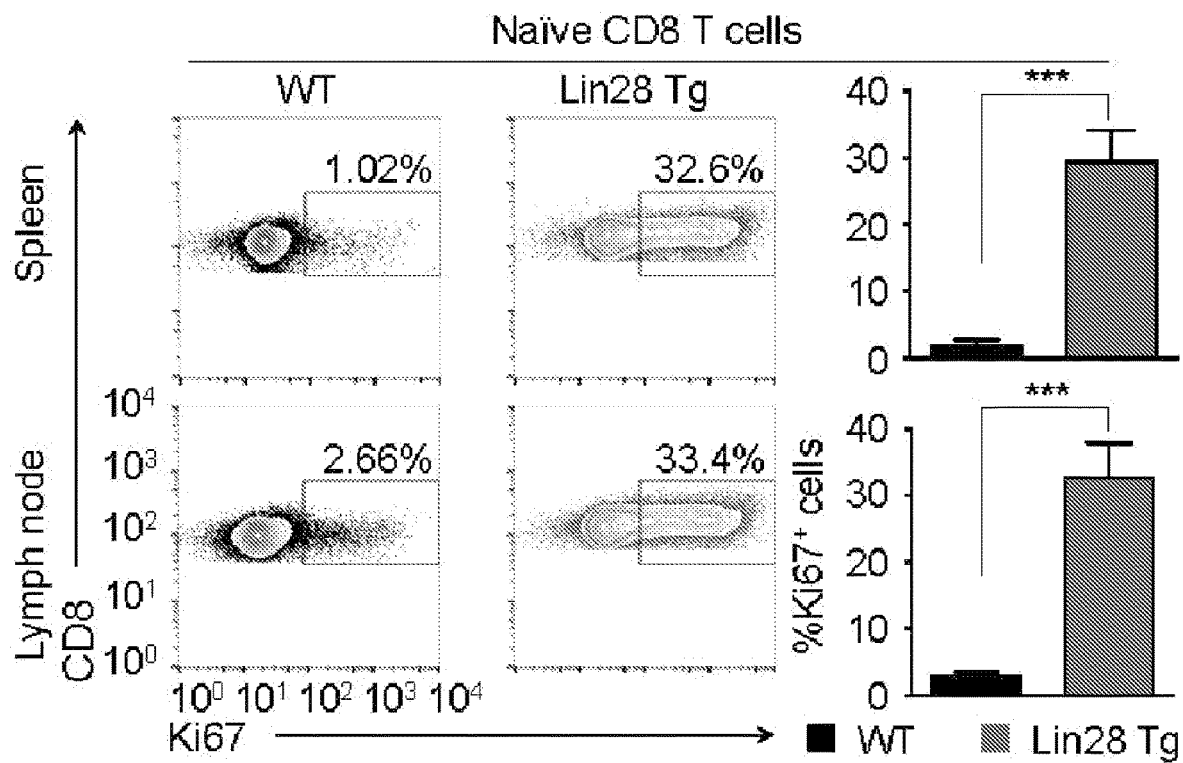

To determine the functional significance of let-7 expression in naïve CD8 lymphocytes, we examined let-7 deficient CD8 T cells from P14+ Lin28Tg Rag2−/− mice where T cell-specific expression of the Lin28 protein blocks let-7 biogenesis (19, 24) and P14 is a monoclonal T cell receptor specific to the lymphocytic choriomeningitis virus (LCMV) peptide gp33-41, presented in the context of H2Db molecules. In comparison to the wild type counterparts, let-7 deficient (Lin28 Tg) P14+ CD8 T cells were significantly larger in size, with a dramatically increased proportion of Ki67 positive cells, which is indicative of a loss of the quiescent state 25 (FIGS. 12C and D). In addition, surface expression of T cell activation markers, such as the IL-2 receptor beta-chain (CD122), and CD44 was also increased, while cells remained CD25 negative. Based on these results, it was concluded that the expression of let-7 miRNAs is needed to maintain the quiescent state in naïve CD8 T cells.

Figure 13A:
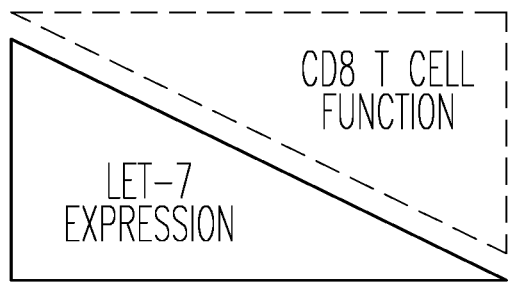
FIGS. 13A-E Inhibitory role of let-7 miRNA expression in CD8 T cell-mediated responses in vivo (a) Schematic representation of the hypothesis that let-7 expression inhibits the differentiation of CD8 T cells. (b) Quantification of the number of donor CD8 T cells from P14$^+$ wild type (n=3) or P14$^+$ let-7 Tg mice (n=3) in the spleens of congenic (CD45.1$^+$) host mice 7 days after cell transfer and LCMV Armstrong infection. (c) Surface expression of the activation marker KLRG1 on wild type host, and indicated donor cells (top). Expression of IFN-γ, and TNF-α in wild type host, and donor LCMV-specific CD8 T cells from the indicated mice, as determined by re-stimulation with the gp33 peptide, and subsequent intracellular staining (middle). Quantification of the % KLRG1$^+$, and % IFN-γ$^+$, TNF-α$^+$ populations in wild type host, and donor cells from the indicated mice (bottom). (d) Survival analysis of wild type (n=5) or let-7 Tg (n=5) mice injected i.p. with 30×10$^6$ P815 cells. (e) Quantification of the number of P815 tumor cells remaining in the peritoneal cavity 7 days after i.p. injection of 20×10$^6$ cells into either wild type (n=6), or let-7 Tg mice (n=5). n.s., not significant ($P>0.05$), * $P<0.05$,  $P<0.01$, and * $P<0.001$, compared with wild type using two-tailed Student's t-test (b, c, d) or one-tailed Student's t-test (e). Data are from one experiment representative of three independent experiments (b, c; mean and s.e.m. of technical triplicates) two experiments (d,e).

Let-7 miRNA Expression in CTLs Affects Both the Anti-Viral and Anti-Tumor Immune Responses TCR stimulation of naïve T cells leads to a rapid loss of the quiescent state and differentiation into effector cells. Given that the expression of let-7 miRNAs, which is needed for the maintenance of naïve CD8 T cells, is inhibited by TCR signaling (FIG. 12A, 1B), it was hypothesized that the downregulation of let-7 miRNAs in response to TCR stimulation is needed for the differentiation and function of effector CD8 T cells (FIG. 13A).

Figure 13B:
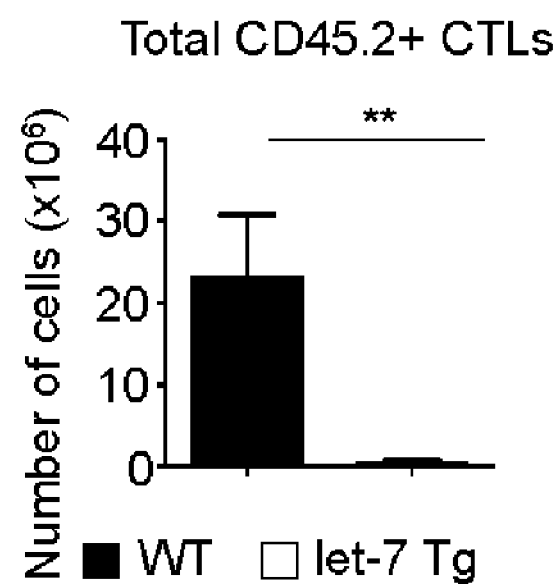
Figure 13C:
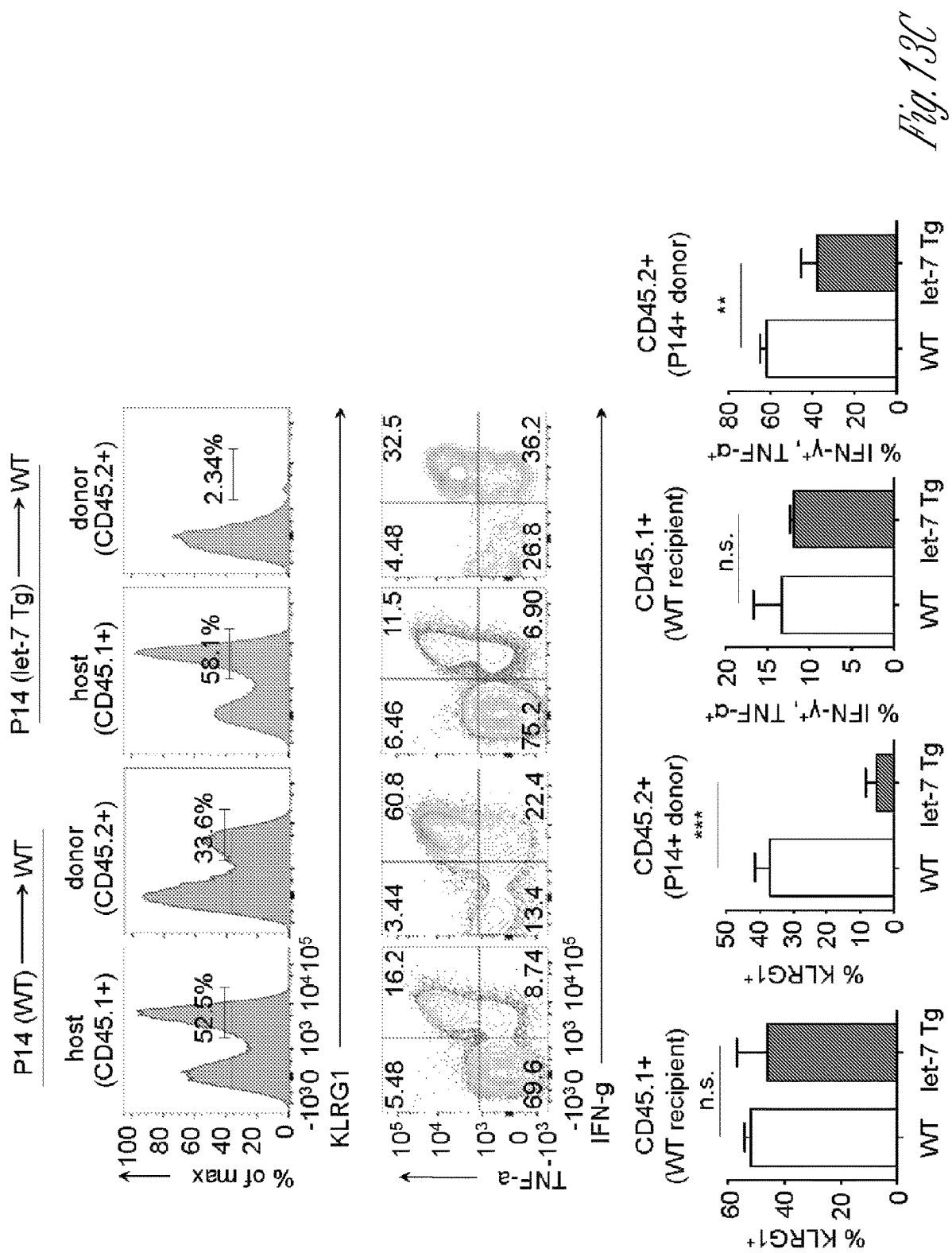

To determine whether TCR-mediated downregulation of let-7 miRNAs is required for CD8 T cell differentiation in vivo, we analyzed the fate of P14+ CD8 T cells with forced let-7 expression, where the doxycycline-inducible let-7g transgene (26) maintains let-7g miRNA expression in lymphocytes in the presence of doxycycline, even after TCR stimulation in response to acute viral infection with lymphocytic choriomeningitis virus (LCMV) Armstrong. Donor CD45.2+CD8+ T cells from P14+ and P14+ let-7 transgenic (let-7 Tg) mice were adoptively transferred into host congenic wild type CD45.1+ mice that were concurrently infected with LCMV, and the differentiation state of P14+ cells was assessed seven days post-injection. Interestingly, the recovery of donor CD8 T cells at the peak of the immune response revealed that P14+ let-7 Tg CD8 T cells failed to clonally expand (FIG. 13B). Furthermore, it was found that P14+ let-7 Tg CTLs lack the expression of KLRG1, an established marker of terminal effector CTLs (27-30). Additionally, KLRG1 is not a target of let-7. Further, let-7 Tg CTLs had a reduced frequency of IFN-γ+TNF-α+ cytokine double-producing cells (FIG. 13C), a hallmark of an effective CD8 T cell response (31-33). Thus, sustained let-7 expression following TCR activation severely impaired the clonal expansion and differentiation of CTLs in response to viral infection in vivo.

Figure 13D:
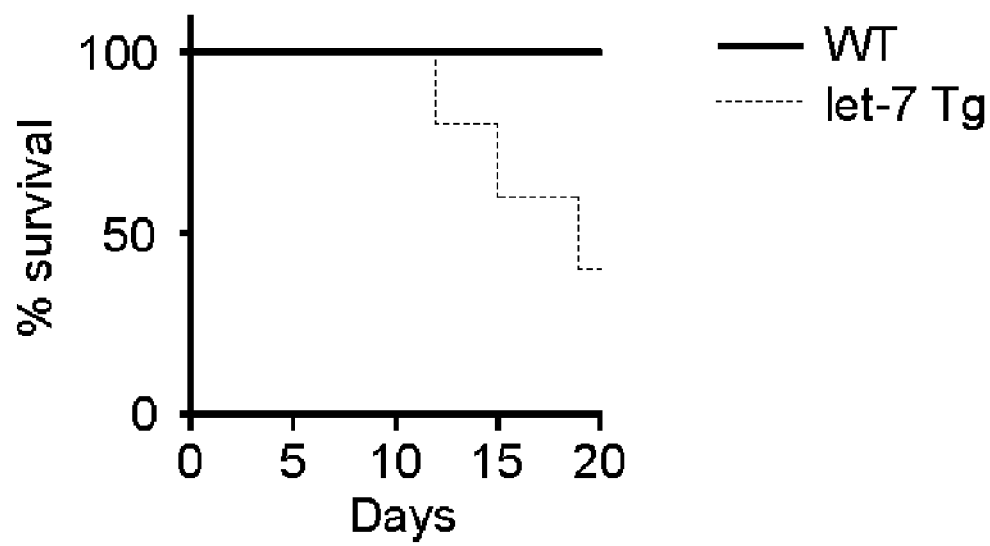
Figure 13E:
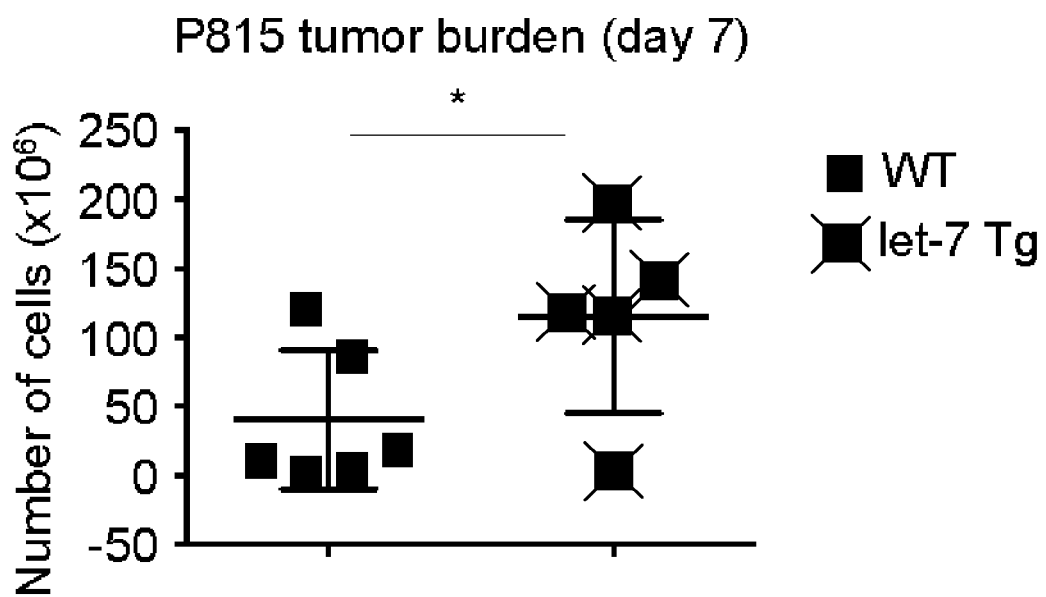

As the allogeneic response to foreign MHC is one of the most robust responses of the immune system, it was determined whether steady levels of let-7 in T cells would suppress the allogeneic response in vivo (34-35). In fact, when the cells of an allogeneic (H2-d haplotype) tumor, the P815 mastocytoma, were injected into wild type or let-7 Tg mice of H2-b haplotype, 60% of let-7 Tg mice were unable to effectively respond to, and clear the tumor (FIG. 13D). Additionally, at seven days post-injection, wild type mice retained on average 40×10$^6$ cancer cells in the peritoneal cavity, while let-7 Tg mice contained 115×10$^6$ cancer cells (FIG. 13E). It was concluded that CD8 T cells that maintained let-7 expression upon stimulation and differentiation had a compromised response to the alloantigen, and thus failed to reject P815 tumor cells. Taken together, the results demonstrate that the decrease in let-7 expression upon TCR activation is needed for the proper proliferation and differentiation of cytotoxic CD8 T cells in vivo.

Expression of Let-7 miRNAs in Activated CD8 T Cells Inhibits Proliferation and the Metabolic Switch To elucidate the underlying mechanisms of let-7 mediated suppression of CD8 T cell responses (FIG. 13), the impact of let-7 microRNAs on T cell clonal Expansion was first analyzed. Sorted naïve (CD44$^{lo}$CD25$^-$) CD8 T cells with different levels of let-7 expression (FIG. 13A) were activated with anti-CD3 in vitro for 3 days. Interestingly, let-7 Tg CD8 T cells proliferated less than their wild type counterparts, while let-7 deficient (Lin28 Tg) CD8 T cells exhibited enhanced proliferation (FIG. 14A). These results indicate that let-7 miRNAs negatively regulate clonal expansion of activated CD8 T cells, which is consistent with previous experiments in vivo (FIG. 13B). Thus, it was concluded that TCR-mediated downregulation of let-7 expression is needed for successful proliferation of activated CD8 T cells.

Figure 14C:
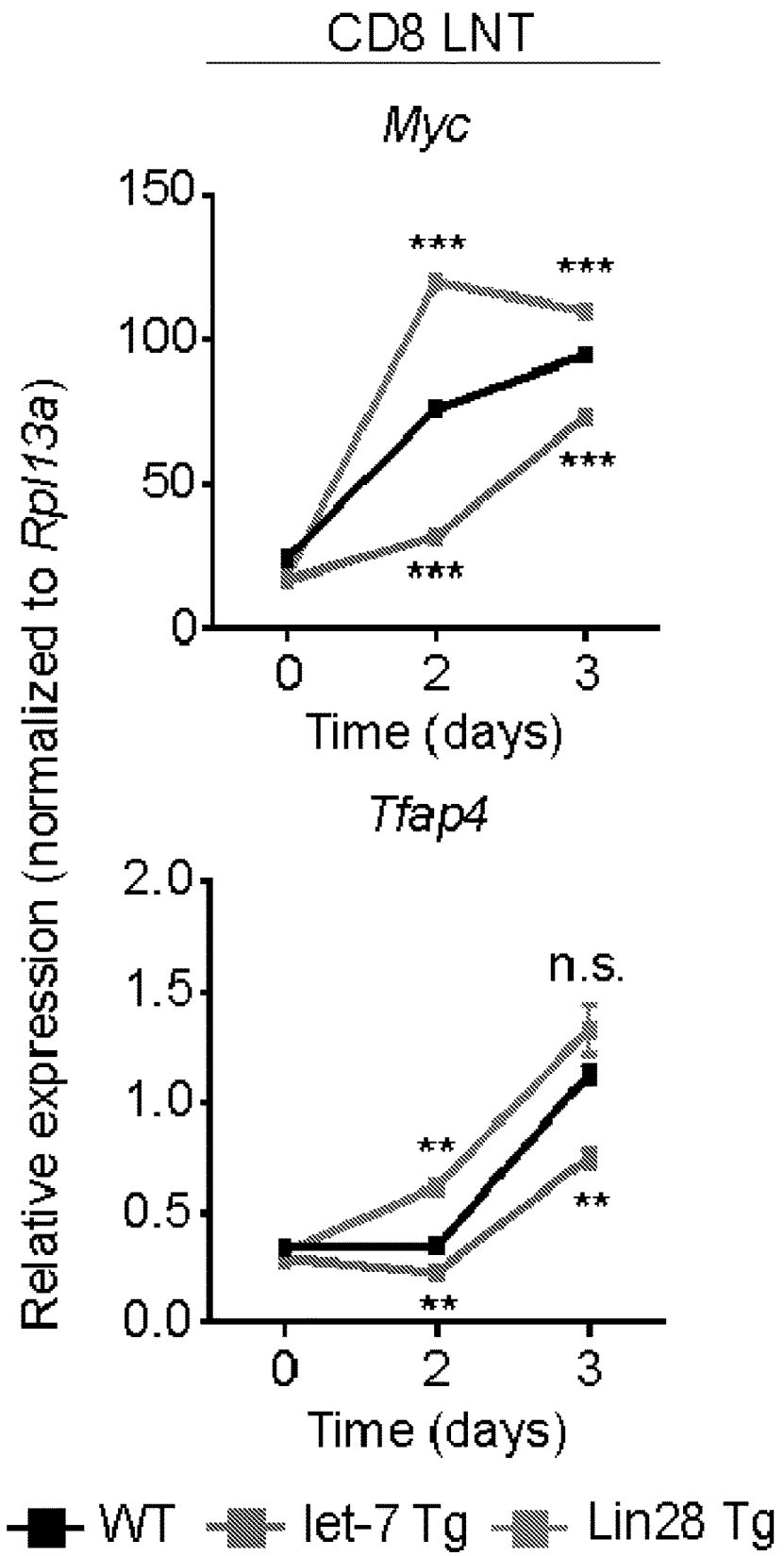

Let-7 miRNAs are well-documented tumor suppressors. It has been shown that let-7 inhibits proliferation in cancerous cells by directly targeting the mRNA of genes that are involved in the regulation of the cell cycle (36). In fact, the expression of some let-7 targets such as phosphatase cdc25a, kinase cdk6, and cyclin D2, was suppressed in activated let-7 Tg CD8 T cells, as compared to Lin28 Tg CD8 T cells where it was derepressed (FIG. 14B). It has been shown that let-7 may also regulate the transcription factor Myc, expression of which is upregulated upon T cell activation and is needed for CD8 T cell proliferation (3, 37-40). In fact, activated let-7 Tg CD8 T cells had reduced expression of Myc, whereas let-7-deficient (Lin28 Tg) CD8 T cells had increased Myc expression (FIG. 14C). To demonstrate that Myc activity was suppressed by let-7, we also analyzed the expression of a direct transcriptional target of Myc, the transcription factor AP4 (Tfap4), which sustains Myc-mediated effects in CD8 T cells during the later stages of differentiation when Myc expression is already low (41). Although AP4 is not a target of let-7, the expression of Tfap4 mRNA was significantly reduced in let-7 Tg CD8 T cells, and enhanced in Lin28 Tg CD8 T cells (FIG. 14C) suggesting that let-7 regulates Myc activity in CD8 T cells.

Figure 14D:
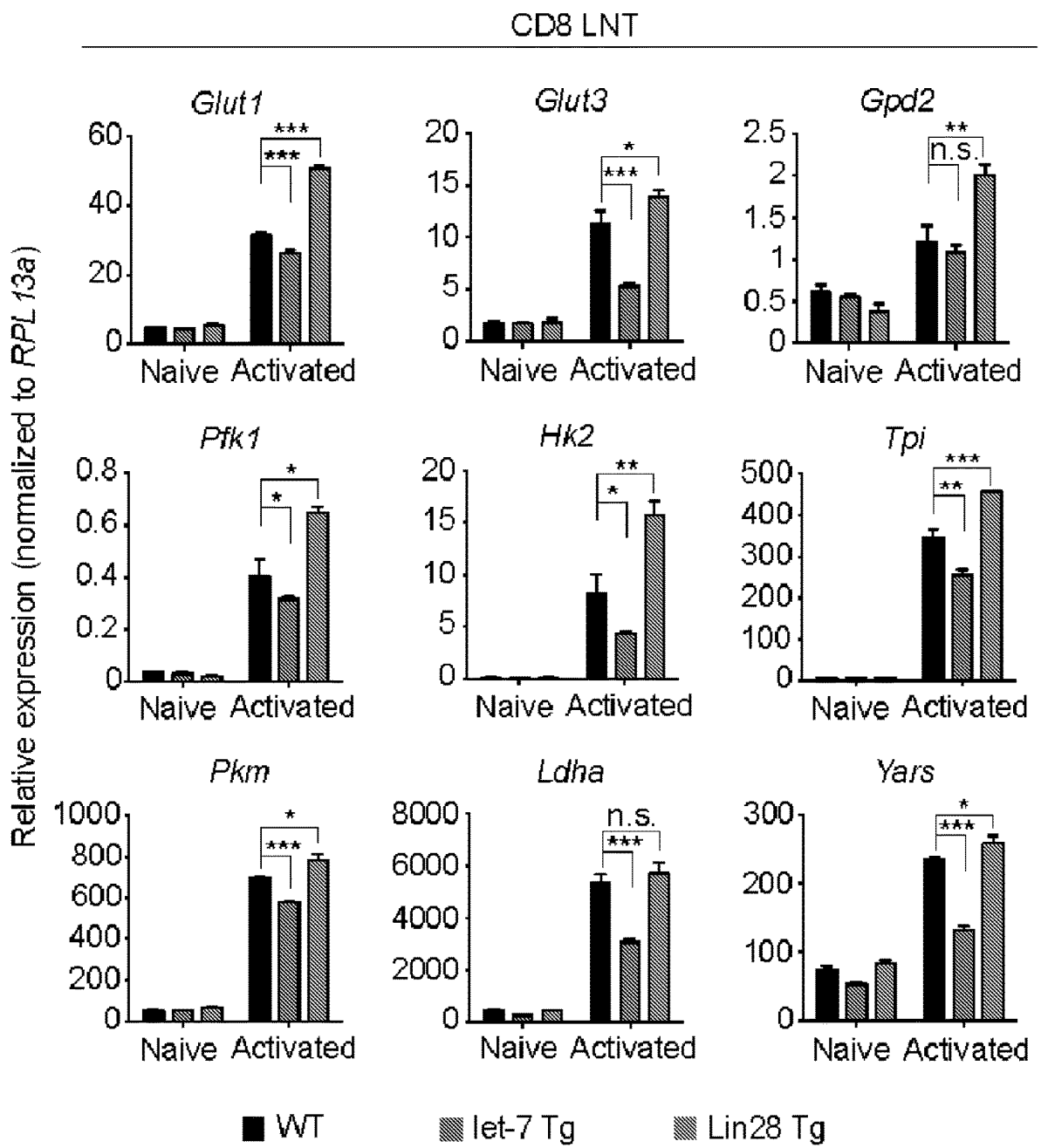

Another function of Myc in activated CD8 T cells is to support the proliferative burst through the metabolic reprogramming of lymphocytes from primarily oxidative phosphorylation (resting) to glycolysis (activated), as well as through an increase in protein synthesis (42-43). To test whether let-7 controls the metabolic switch in activated CD8 T cells through its regulation of Myc, we assessed the expression of key glucose transporters, glycolytic enzymes, and protein synthesis enzymes that have been established as direct targets of Myc in activated CD8 T cells (43). In fact, the expression of all tested targets was suppressed in let-7 transgenic CD8 T cells, and increased in let-7 deficient (Lin28 Tg) signaled lymphocytes, suggesting that let-7 expression likely controls Myc-dependent metabolic reprogramming of activated CD8 T cells (FIG. 14D). Taken together, these results demonstrate that let-7 miRNAs regulate the proliferation of activated CD8 T cells by modulating the expression and activity of genes that are involved in the regulation of the cell cycle and metabolic switch.

Let-7 Expression Regulates the Function of Differentiated CD8 T Cells

Figure 15A:
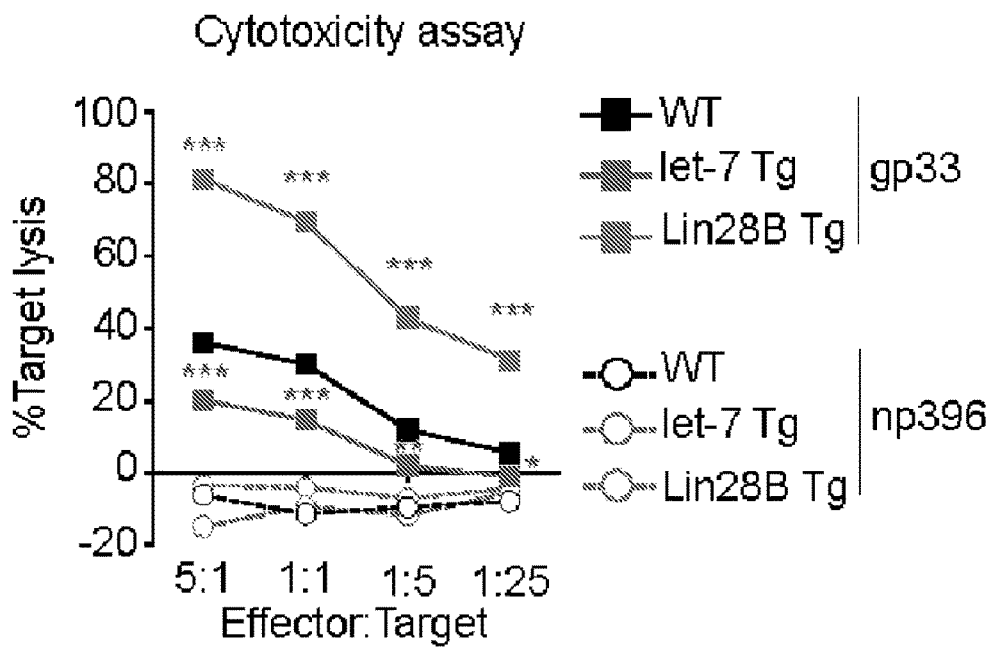
FIGS. 15A-F let-7 miRNAs negatively regulate differentiation and acquisition of effector function in CTLs (a, b) Cytotoxicity assay of differentiated CTLs from P14$^+$ wild type, P14$^+$ let-7 Tg, and P14$^+$ Lin28 Tg lymph nodes (a) or from P14$^+$ wild type (WT), or P14$^+$ let-7 Tg$^+$ Lin28 Tg$^+$ Rag2$^{-/-}$ (4Tg) lymphocytes co-cultured with either LCMV gp33 or LCMV np396 peptide pulsed splenocytes for 4-5 hours, either in the presence or absence of doxycycline (b). (c) Analysis of the internal complexity (FSC, forward scatter; SSC, side scatter) of effector (5 days after anti-CD3 stimulation) CD8 T cells generated from wild type, let-7 Tg, and Lin28 Tg lymphocytes (left) and quantification of SSC of CD8 T cells normalized to wild type. (d) Quantification of Granzyme A and Granzyme B-positive granules in wild type, let-7 Tg, and Lin28Tg CTLs via MilliPore Amnis ImageStream. (e) Quantitative RT-PCR analysis of effector molecule mRNA expression: Gzma (Granzyme A), Gzmb (Granzyme B), Prf1 (Perforin) in naïve and effector CD8 T cells from wild type, let-7 Tg, and Lin28 Tg lymph nodes, presented relative to expression of the ribosomal protein Rpl13a. (f) Staining (top, middle) and MFI (bottom) of Granzyme B, Interferon-γ, and Granzyme A in wild type, let-7 Tg, and Lin28 Tg effector CD8 T cells normalized to wild type. n.s., not significant ($P>0.05$), * $P<0.05$,  $P<0.01$, and * $P<0.001$, compared with wild type using two-tailed Student's t-test. Data are from one experiment representative of three experiments (a, b, e; mean and s.e.m. of technical triplicates, f; mean and s.e.m of three experiments).
Figure 15B:
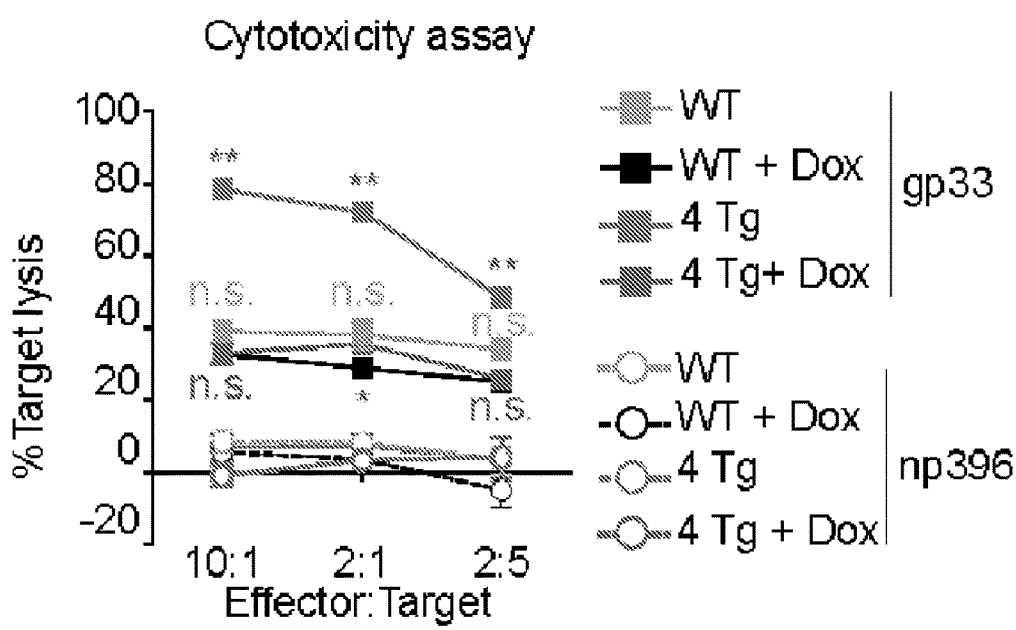

To identify whether let-7 mediated suppression of CD8 T cell immune responses is due to a failure to acquire effector function in addition to a proliferative defect, the cytotoxic activity of CTLs generated from P14+ wild type, P14+ let-7 Tg, and P14+ Lin28 Tg mice were assessed. In fact, the expression of the let-7 transgene in P14+ CTLs greatly diminished their cytotoxic activity (FIG. 15A). Alternatively, P14+ Lin28 Tg CTLs exhibited enhanced cytotoxicity (FIG. 15A), which could be reduced by restoring let-7 expression through the induction of the doxycycline-inducible let-7 transgene in P14+ Let-7 Tg Lin28 Tg (4 Tg) CTLs (FIG. 15B). Thus, it was demonstrated that TCR-mediated downregulation of let-7 microRNAs is needed for the acquisition of cytotoxic function in differentiating CD8 T cells.

Figure 15C:
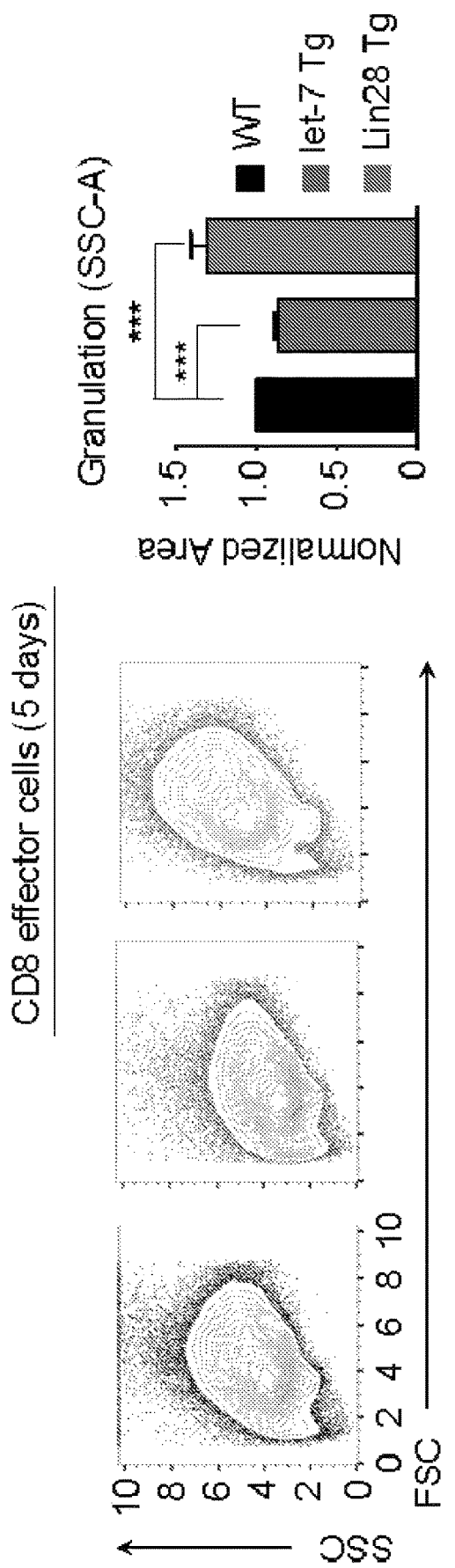
Figure 15D:
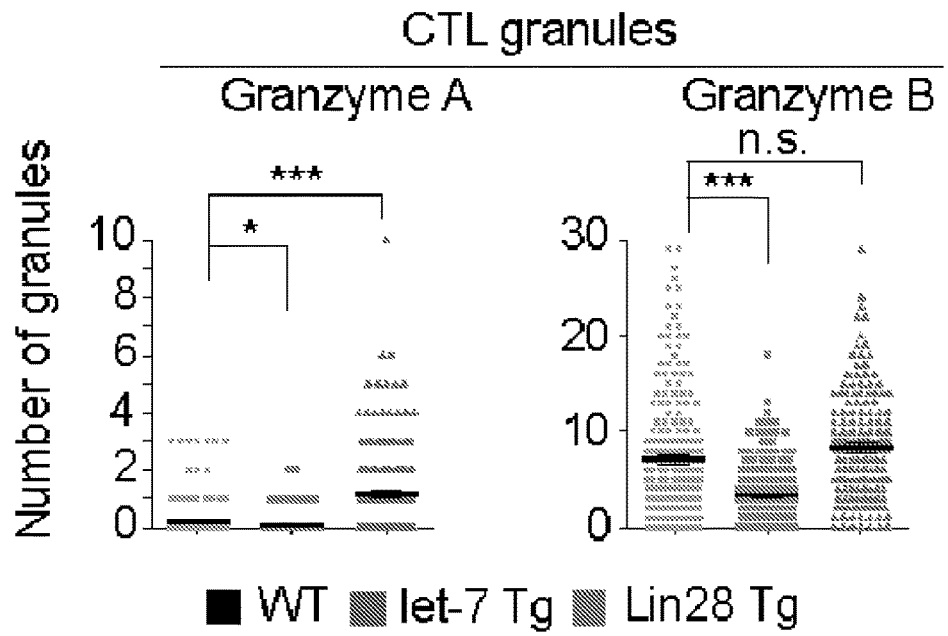

To investigate the mechanism of how let-7 miRNA expression impacts CD8 T cell function, the phenotype of in vitro generated effector CTLs from wild type, let-7 Tg, and Lin28 Tg mice were examined. Activated let-7 Tg CTLs had less internal complexity based on the intensity of side scatter (SSC) than wild type cells, whereas Lin28 Tg CD8 effector cells had significantly greater internal complexity (FIG. 15C), suggesting a change in the number of cytotoxic granules. Indeed, let-7 Tg CTLs contained fewer Granzyme A and Granzyme B positive granules than wild type CTLs, while Lin28 Tg CTLs had more (FIG. 15D). These results indicated that the expression of let-7 controls the quantity of cytotoxic granules produced during the differentiation of CTLs.

Figure 15E:
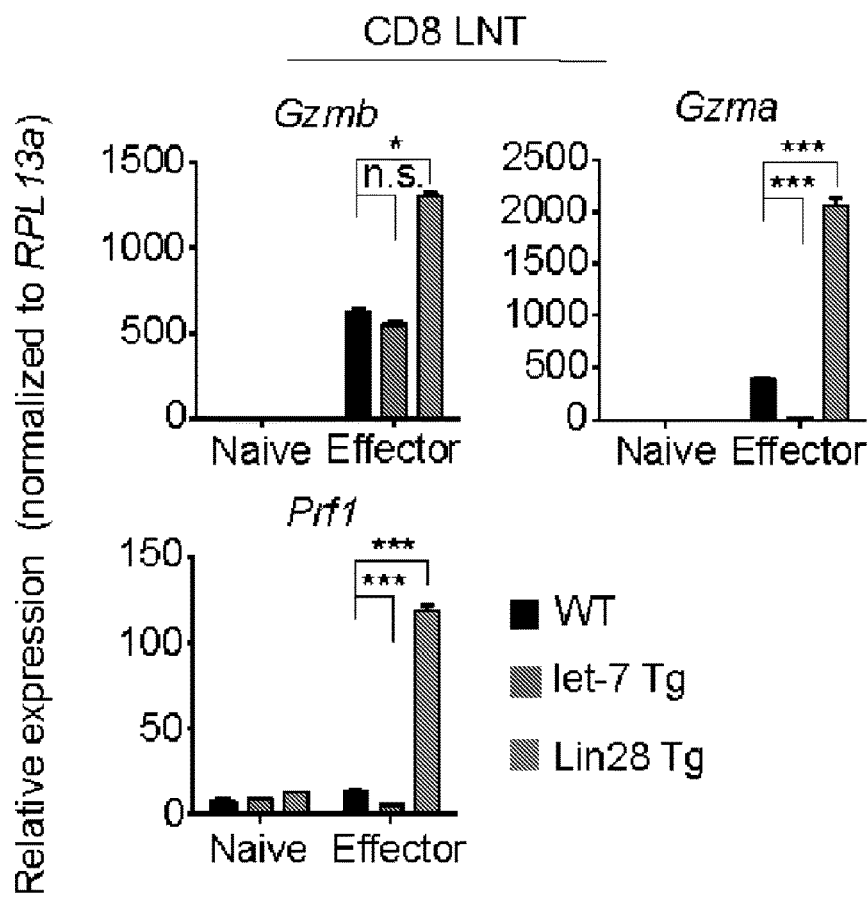
Figure 15F:
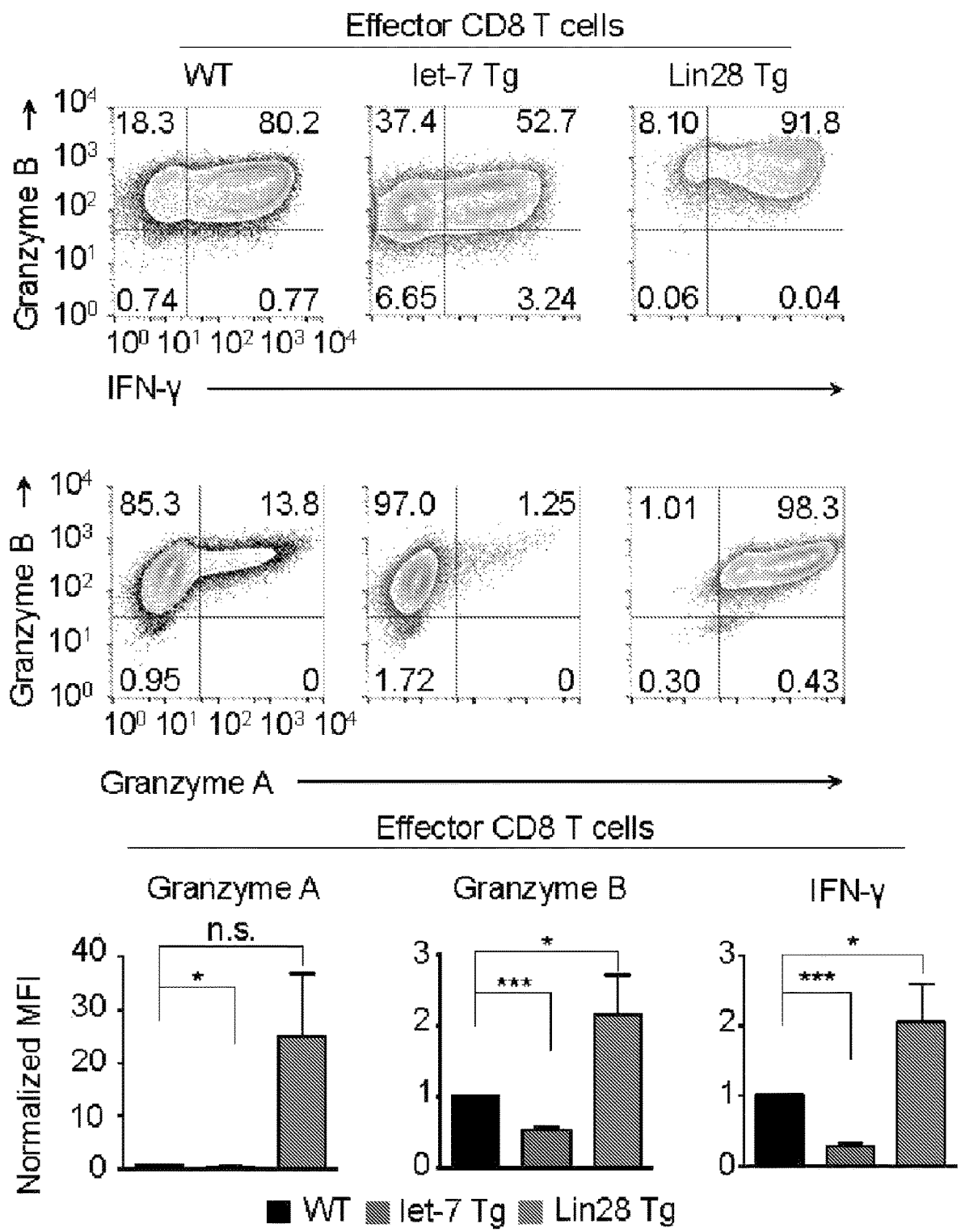

Next, to determine whether let-7 expression in CTLs influences the number of granules by controlling the expression of effector molecules, gene expression of Granzyme A (Gzma), Granzyme B (Gzmb), and Perforin (Prf1), the key cytolytic factors in cytotoxic granules (44-45), was measured. Let-7 Tg CTLs, which contained fewer cytotoxic granules, expressed less mRNA for Gzma, Gzmb, and Prf1, as compared to wild type cells, while Lin28 Tg (let-7 deficient) CTLs had higher expression of these effector molecules (FIG. 15E). The observed changes in mRNA expression of effector molecules, including Interferon-gamma (IFN-γ), were consistent at the protein level (FIG. 15F). Thus, it was concluded that let-7 microRNAs prevent the expression of cytolytic effector molecules in CTLs. Together, these data indicate that let-7 miRNAs negatively regulate CTL function by preventing the expression of important cytotoxic molecules.

Figure 16A:
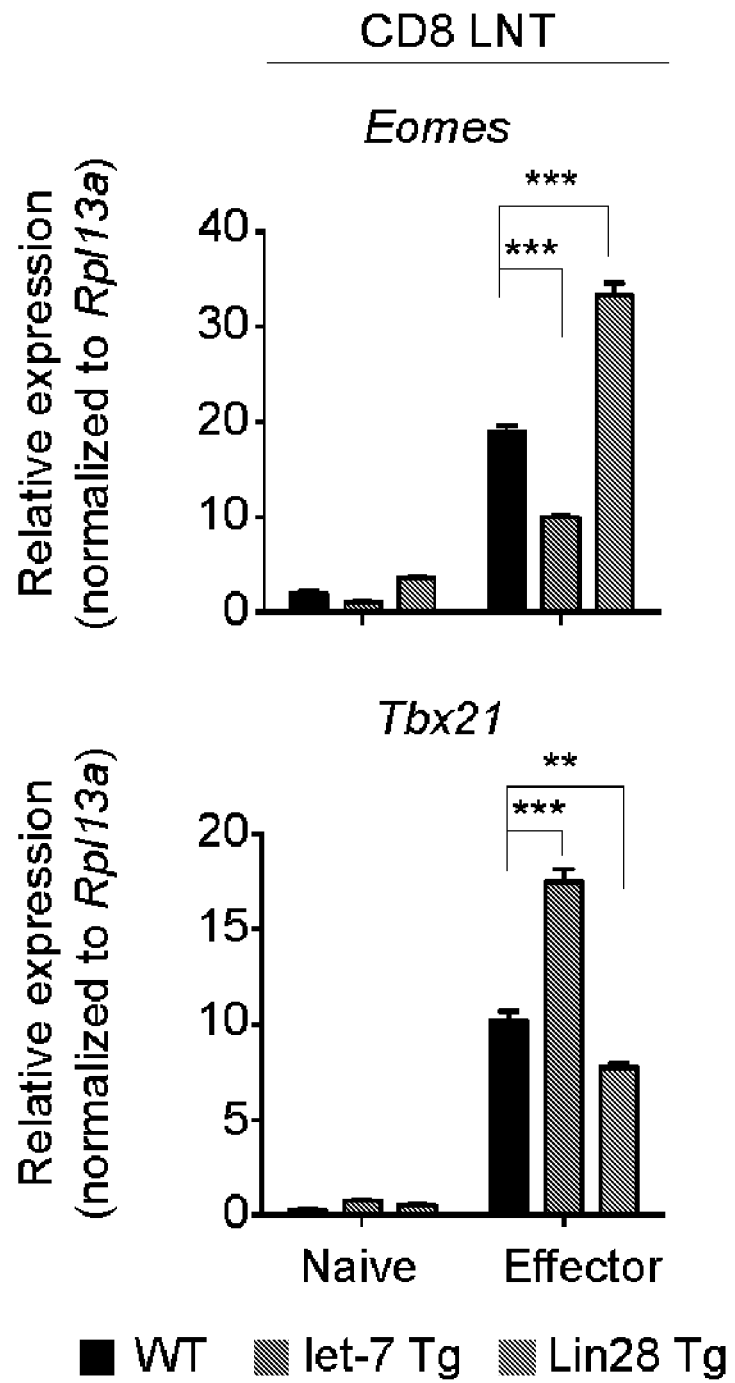
FIGS. 16A-D let-7 miRNAs directly target the mRNA of Eomes in activated CD8 T cells (a) Quantitative RT-PCR analysis of Eomes (Eomesodermin) and Tbx21 (T-bet) mRNA in naïve and effector CD8 T cells (5 days after anti-CD3 stimulation) generated from wild type, let-7 Tg, and Lin28 Tg lymphocytes, presented relative to the ribosomal protein Rpl13a. (b) Staining of Eomes and T-bet (left) and MFI of Eomes and T-bet (right) in wild type, let-7 Tg, and Lin28 Tg effector CD8 T cells, normalized to wild type. (c) Eomes mRNA, including the 3' and 5' untranslated regions (UTR) and the open reading frame (ORF) within which exists one let-7 binding site which we identified (top) and a sequence alignment of the mouse and human let-7 binding sites (middle). Included is the mutated sequence of the let-7 binding site in the mouse cDNA of Eomes (bottom) used in the luciferase reporter assay. (SEQ ID NOs: 53, 54 and 55) (d) Luciferase reporter assay of let-7 targeting of the Eomes ORF in NIH 3T3 fibroblasts transfected with a luciferase reporter containing either the intact or mutated sequence of the let-7 seed region from the Eomes ORF; the activity of the firefly luciferase was normalized to the Renilla luciferase control. n.s., not significant (P>0.05),  P<0.05,  P<0.01, and *** P<0.001, compared with wild type using two-tailed Student's t-test. Data are from one experiment representative of three independent experiments (a, b, d; mean and s.e.m. of technical triplicates (a,d) or three experiments (b)).
Figure 16B:
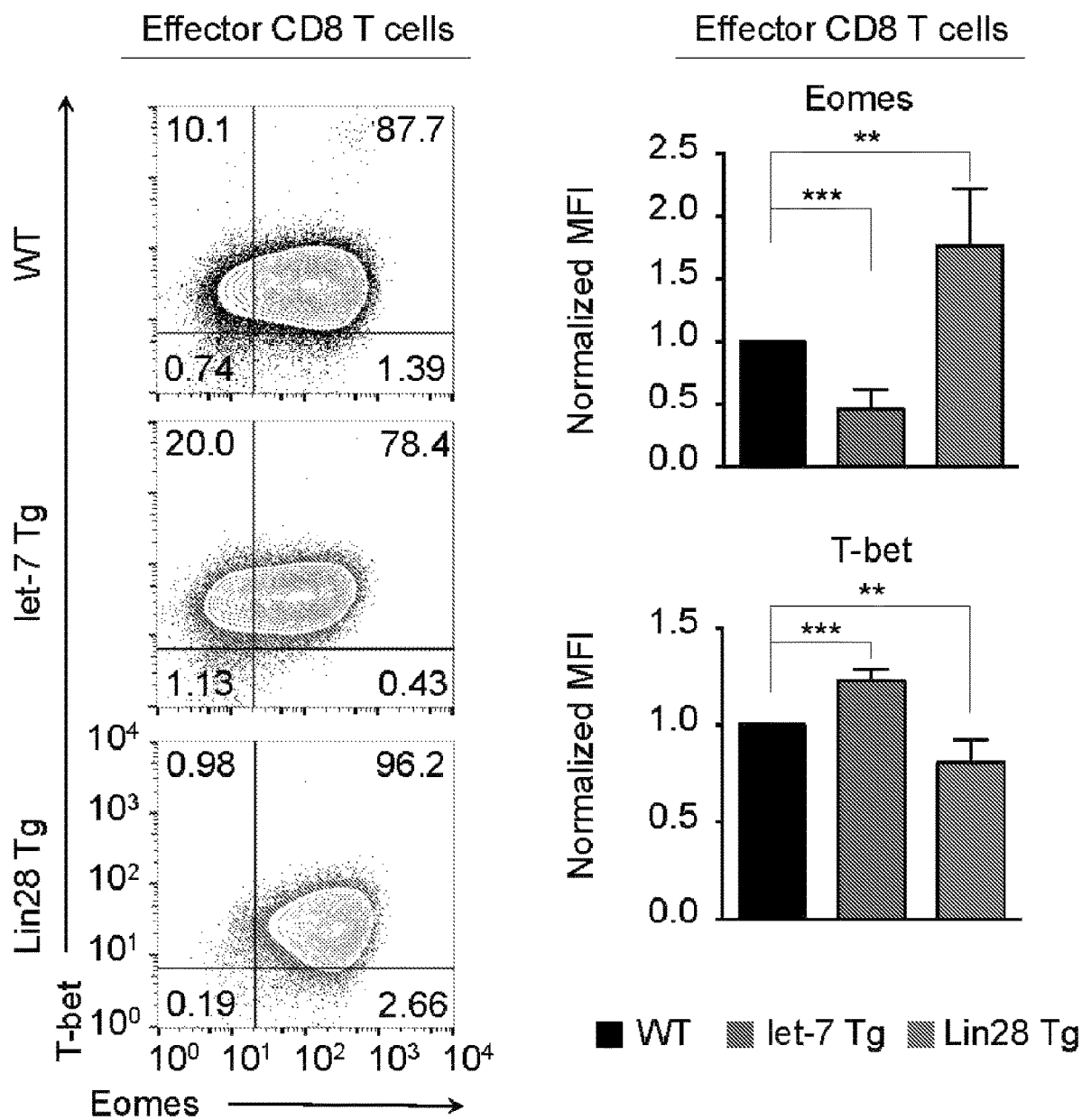
Figure 16C:
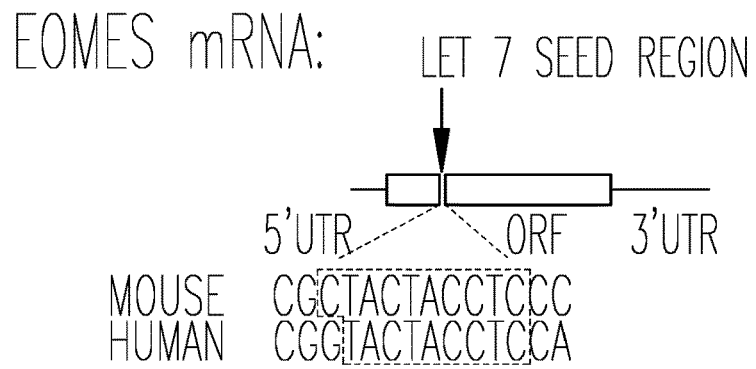

Let-7 miRNAs Directly Target the 'Master Regulator' Transcription Factor, Eomesodermin During CTL Differentiation To determine how let-7 regulates the differentiation and function of CTLs, the possibility that let-7 miRNAs may directly regulate the expression of effector molecules was considered. Although typical miRNA binding sites are found in the 3' untranslated regions (UTRs) of mRNA transcripts (46-48), the full length mRNA of Prf1, Gzma, Gzmb, and Ifng were analyzed, yet no let-7 binding sites were found. This suggested that let-7 may indirectly regulate the expression of these molecules by controlling more global regulators, such as transcription factors. It is known that the expression of effector molecules and cytotoxic function of CD8 T cells are tightly regulated by a group of transcription factors, including Eomesodermin (Eomes), T-bet, Notch-1 and Blimp-1 (2, 4, 49-52). To determine if these factors are regulated by let-7, their relative gene expression in CTLs with different levels of let-7 was assessed. The only transcription factor whose expression on both the mRNA and protein levels was reduced in let-7 transgenic CTLs, and enhanced in Lin28 Tg (let-7 deficient) CTLs, was Eomes (FIG. 16A, B). Of note, it was also found that T-bet expression inversely correlated with Eomes, suggesting that an Eomes dependent mechanism may control T-bet expression (FIG. 16A, B). These results demonstrate that let-7 miRNAs negatively regulate Eomes expression.

Figure 16D:
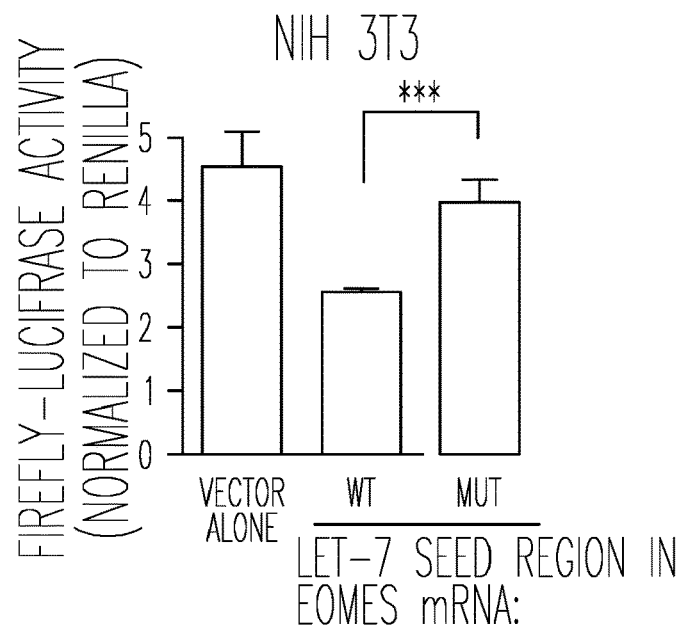

Next, it was determined whether let-7 miRNAs can target Eomes mRNA. Interestingly, there is no let-7 binding site located in the 3'UTR of Eomes, but rather a conserved binding motif within the open reading frame of Eomes mRNA was identified (FIG. 5C). To determine whether this binding site is functional, the 10-nucleotide mouse Eomes-let-7 binding motif was cloned into a dual luciferase vector. The vector was then transfected into NIH 3T3 fibroblasts, which have high endogenous expression of the let-7 family members. This resulted in a significant decrease in luciferase activity, indicating that let-7 can directly bind Eomes (FIG. 16D). When this sequence was mutated, disrupting the let-7 binding site, luciferase activity was restored, confirming that let-7 miroRNAs directly target Eomes mRNA (FIG. 16D).

Let-7 miRNAs Suppress CD8 T Cell Function Through Targeting Eomes

Figure 17A:
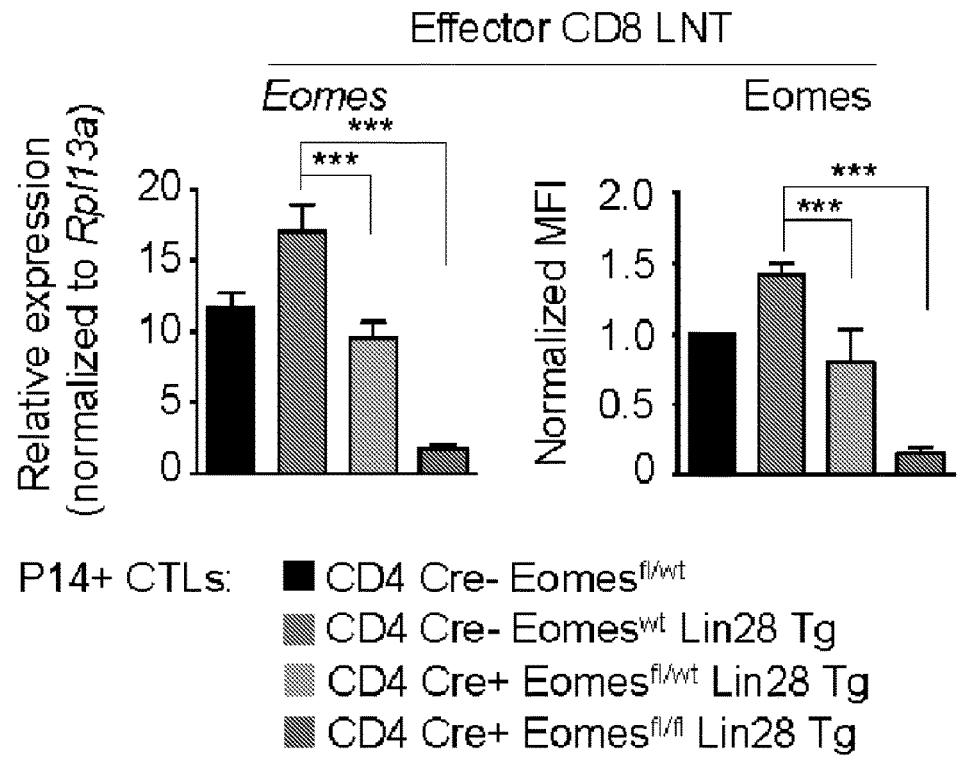
FIGS. 17A-D let-7 mediated-expression of Eomes controls the differentiation of CTLs (a) Quantitative RT-PCR analysis of Eomes mRNA, presented relative to the ribosomal protein Rpl13a (left) and MFI of Eomes expression, normalized to wild type (right), from CTLs generated from CD4-Cre-Eomes$^{fl/wt}$ P14$^+$, CD4-Cre$^-$ Eomes$^{wt}$ P14$^+$ Lin28 Tg, CD4 Cre$^+$ Eomes$^{fl/wt}$ P14+ Lin28 Tg, and CD4 Cre+ Eomes$^{fl/fl}$ P14$^+$ Lin28 Tg CD8 T cells. (b) Quantitative RT-PCR analysis of GzmA (Granzyme A) and Prf1 (Perforin) mRNA in effector CTLs generated from the indicated mice, presented relative to the expression of the ribosomal protein Rpll3a. (c) Staining of Granzyme A in CTLs generated from the the indicated mice. (d) Cytotoxicity assay demonstrating specific target lysis of differentiated P14$^+$ CTLs from the indicated mice, co-cultured with either LCMV gp33 or LCMV np396 peptide-pulsed splenocytes for 4-5 hours.  P<0.01, and * P<0.001, compared with Lin28 Tg using two-tailed Student's t-test. Data are from one experiment representative of two independent experiments (a; mean and s.e.m. of two experiments; b, d; mean and s.e.m. or technical triplicates).
Figure 17B:
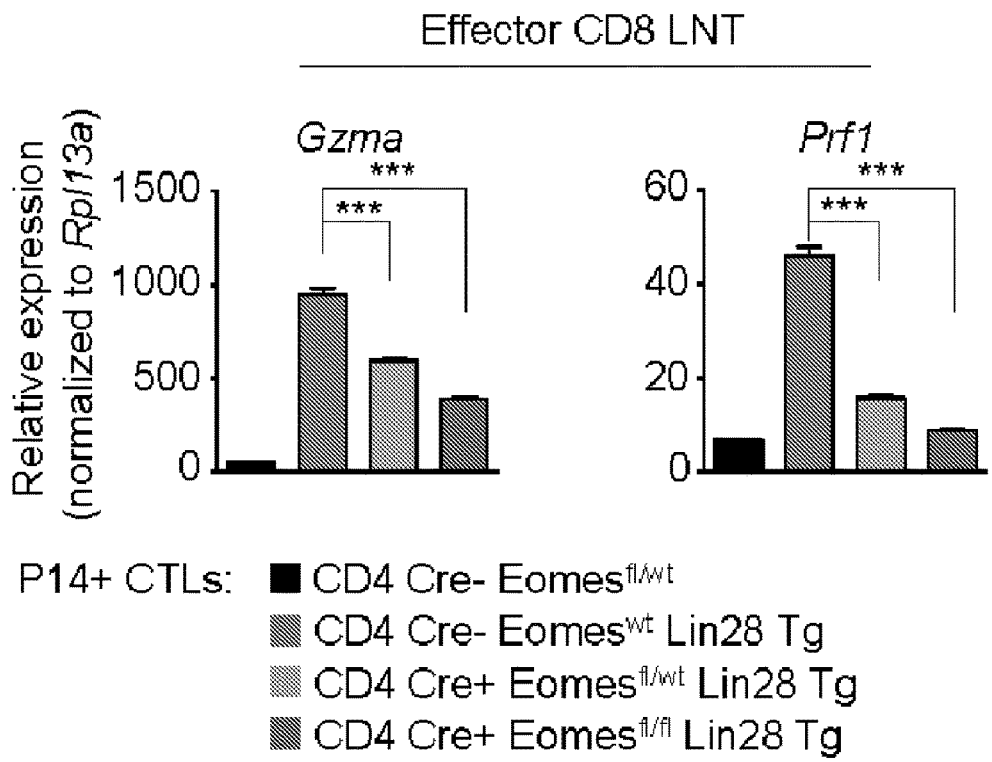
Figure 17C:
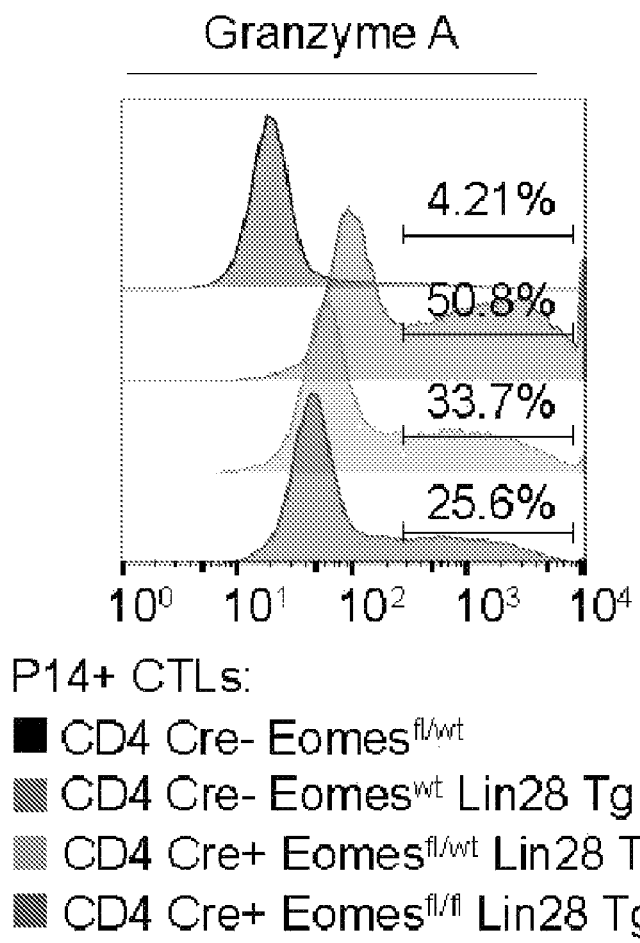

To ascertain whether let-7 controlled CD8 T cell differentiation and function through Eomes, Eomes expression in Lin28 Tg CTLs was depleted, expecting the reduction of enhanced cytotoxicity in let-7-deficient cells. T-cell specific deletion of either one or both alleles of Eomes in CTLs generated from P14+ CD4 Cre$^+$ Eomes$^{fl/wt}$ Lin28 Tg, and P14+ CD4 Cre$^+$ Eomes$^{fl/fl}$ Lin28 Tg T cells resulted in gradually decreased levels of Eomes (FIG. 17A). Any residual Eomes expression in CTLs derived from CD4Cre$^+$ Eomes$^{fl/fl}$ Lin28 Tg mice, was attributed to "escapees" of the conditional knockout. Consistent with previous results, (FIG. 15E, F) Lin28 Tg effector T cells expressed high levels of effector molecules at both the transcript and protein levels (FIG. 17B, C). The expression of the effector molecules Gzma, and Prf1 was reduced in a manner consistent with the expression of Eomes, where loss of Eomes ameliorated the enhanced expression of these effector molecules in Lin28 Tg effector cells (FIG. 17B, C).

Figure 17D:
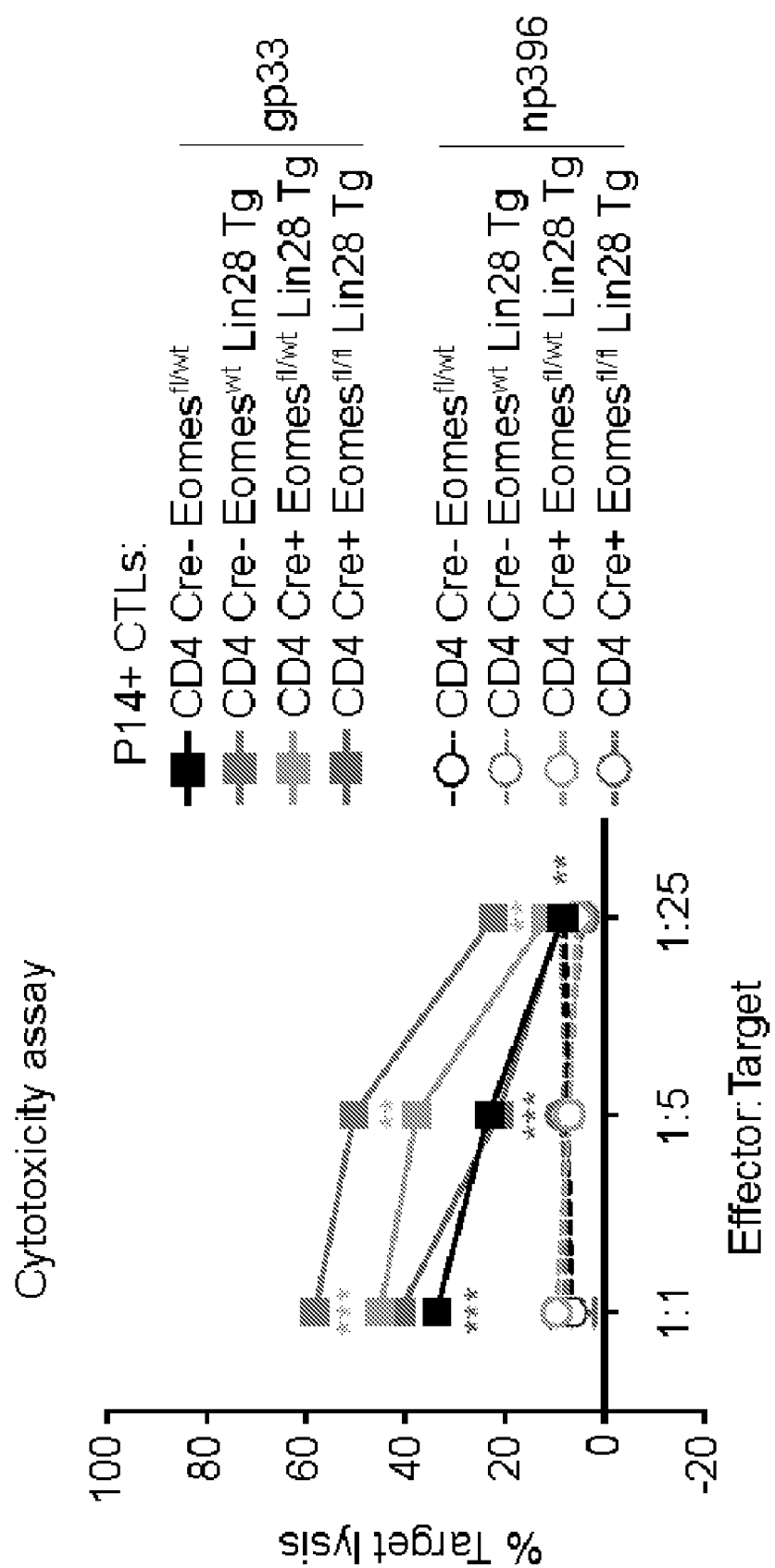

However, the expression of Granzyme B was not affected by loss of Eomes expression, suggesting Granzyme B may be more complexly regulated through other let-7-dependent, but Eomes-independent mechanisms. Ultimately, the loss of Eomes expression resulted in a moderate reduction of cytotoxic function, even in the absence of let-7 microRNAs (FIG. 17D). These results demonstrate that let-7-mediated suppression of Eomes is in part responsible for the compromised differentiation and cytotoxic function of let-7 Tg CTLs in vitro.

Thus, the data suggest a model in which the let-7 miRNAs act as a molecular control hub that drives CD8 T cell differentiation and function, in a manner dependent on the magnitude of TCR stimulation. Furthermore, it is proposed that modulation of let-7 miRNA expression in CD8 T cells provides an exciting, novel therapeutic application to control CTL responses.

DISCUSSION

The study provided herein has identified a role for the let-7 miRNAs in regulating the transition between naïve and effector stages of CD8 T cells. Specifically, let-7 expression is initially high in naïve T cells and, when absent, results in a loss of the quiescent phenotype in CD8 lymphocytes. Moreover, the entire family of let-7 miRNAs is downregulated upon antigen stimulation through the TCR, which is demonstrated as needed for the successful progression of CD8 T cell differentiation into CTLs. Therefore, the data suggest that let-7 expression keeps CD8 T cells in a naïve state and prevents CTL differentiation, while the magnitude of TCR-mediated downregulation of let-7 expression guides the proliferation, differentiation and the acquisition of effector function of CD8 T cells.

Let-7 microRNAs have been shown to play a role in early development, metabolism and cancer (26, 53-56). Recent studies have also implicated the importance of the let-7 miRNAs in the development, maintenance, and function of the immune system, including T cells (19, 20, 23). Using both gain-of-function experiments employing a let-7 Tg mouse capable of sustaining let-7 expression following TCR activation, and loss-of function experiments using a let-7 deficient mouse (Lin28 Tg), the study provided herein has corroborated these earlier reports, and has identified a novel role for let-7 in CD8 T cell differentiation and function.

Prior to antigen encounter, naïve CD8 T cells are maintained in a quiescent state, in which T cells have no effector function, are metabolically inactive and undergo minimal proliferation. It has been shown that the homeostasis of naïve T cells depends on the balance of two signals, the recognition of low affinity self-ligands by the TCR, and cytokine stimulation (57-61). Although it has become clear that the weak recognition of self-ligands is not enough for naïve T cells to lose the quiescent state, the molecular mechanism that prevents the spontaneous activation of T cells under these conditions is not fully understood. Here, it is demonstrated that the high expression of let-7 microRNAs is necessary to maintain CD8 T cells in a naïve state. In fact, it is observed that let-7 ablation in CD8 T cells leads to the loss of the quiescent phenotype, as indicated by exit from the G0 stage of the cell cycle, an overall increase of cell size, and the upregulation of activation markers such as CD122, and CD44 (25, 62). These experiments were conducted using CD8 T cells from P14+ Lin28 Tg Rag2−/− mice in order to prevent bystander effects from IL-4-producing PLZF+ cells present in Lin28 Tg Mice (19, 20, 63). It is concluded that the high expression of let-7 microRNAs prevents the spontaneous activation of naïve T cells.

Furthermore, it was found that the let-7 mediated "molecular brake" is released upon antigen stimulation, leading to the profound downregulation of all members of the let-7 microRNA family in activated CD8 T cells, depending on the strength of TCR stimulation. Using in vivo models to assess both anti-viral and anti-tumor immunity, it was demonstrated the importance of let-7 miRNAs in controlling CD8 T cell-mediated immune responses. Let-7 Tg CD8 T cells failed to proliferate in response to acute LCMV infection, and the few let-7 Tg cells that did respond exhibited a very weak effector phenotype, suggesting that downregulation of let-7 is important to both the proliferative burst of antigen-specific CD8 T cells upon encounter with viral antigen, and the differentiation of these cells in vivo. These results were further bolstered by the failure of let-7 Tg mice to reject allogeneic tumor, P815 mastocytoma. Altogether, the in vivo studies demonstrate the significance of let-7 downregulation in effector CD8 T cells, and suggest a novel level of control of immune responses that can be therapeutically targeted for treatment of infectious diseases, cancer and autoimmunity.

Antigen stimulation of T cells results in the increased biosynthesis that is needed to support the clonal expansion of antigen specific lymphocytes, and ultimately the acquisition of effector function. The hallmark of this process is a metabolic switch from oxidative phosphorylation to aerobic glycolysis (64, 65), as well as a concomitant increase in cell size, both of which have been reported to be controlled by Myc (41, 43, 66), the expression of which is rapidly induced upon antigen stimulation of CD8 T cells (33, 43, 66). Presumably due to the pro-apoptotic activity of Myc (67-69), its expression is transient, eventually receding during the later stages of CD8 T cell differentiation (3, 39). In the study, it is shown that let-7 suppresses the expression of Myc on the mRNA level, and consequently modulates the function of Myc in CD8 T cells, based on the assessment of established Myc targets, supporting the previous observation of Myc as a noncanonical target of let-7 miRNAs in cancer cells (38, 70). The results suggest that let-7 likely regulates the metabolic switch in activated CD8 T cells through Myc.

It was also found that the let-7 miRNAs may directly inhibit the proliferation of activated CD8 T cells by suppressing the expression of the cell cycle regulators Cdc25a, Ccnd2 and Cdk6, all of which are known let-7 targets (36). Since these factors have also been described as transcriptional targets of Myc (71-73) it cannot be ruled out that the possibility of more complex regulation where let-7 is not solely responsible for controlling their expression.

Moreover, it was demonstrated that let-7 mediated suppression of CD8 T cell immune responses is also due to modulation of the acquisition of effector function. It was noticed that the internal complexity of CTLs generated in vitro was diminished in the presence of forced let-7 expression, and subsequently determined that this was due to a reduction in the number of cytotoxic granules, as well as in the expression of effector molecules. It is thus concluded that let-7 functions as a molecular rheostat that quantifies TCR signaling to direct the CTL response upon antigen stimulation, in a similar fashion to other miRNAs, including miR-181 and the miR-17-92 cluster (12, 13, 18).

The molecular mechanisms through which let-7 acts to inhibit CTL differentiation was determined. It was found that Eomes is directly regulated by let-7 microRNAs, which can in part explain the block in the differentiation of CD8 T cells with forced let-7 expression. Yet, in contrast to previous studies on the differential roles of Eomes and T-bet in governing CD8 T cell function, it is shown that heightened expression of Eomes in effector T cells may be more important for effector function than previously thought (4, 62, 74). In fact, let-7/Eomes-double deficient CTLs had much reduced antigen-specific cytotoxicity in vitro. However, the data also suggests that Eomes is only a part of this "cytotoxic program", as deletion of Eomes only reduced cytotoxicity to the levels exhibited by wild type CTLs. This result implicates that other let-7-dependent, but Eomes-independent mechanisms are at play. Additionally, it was confirmed that Perforin, Granzyme B, and IFN-γ expression is controlled by Eomes (4) while also having identified Granzyme A as a probable target of Eomes. These results are consistent with the enhanced cytotoxicity exhibited by let-7 deficient CD8 T cells with increased Eomes expression. Also observed was previously reported reciprocal expression between T-bet and Eomes (62, 74, 75).

These results demonstrate that downregulation of let-7 upon TCR stimulation is a needed process in the determination of the magnitude of the CD8 T cell response in vivo, as let-7 miRNAs inhibit proliferation and differentiation by targeting cell cycle regulators, prevent metabolic reprogramming through the suppression of Myc, and repress the acquisition of effector function through Eomes dependent and independent mechanism. Thus, naïve CD8 T cells need let-7 miRNAs to remain quiescent, and only upon antigen stimulation through the TCR can this molecular "brake" be released. Based on these results, it is proposed that let-7 miRNAs act as a molecular control hub that translates TCR signaling to control CD8 T cell differentiation and function.

BIBLIOGRAPHY

1. Ward, P. S. & Thompson, C. B. Signaling in control of cell growth and metabolism. *Cold Spring Harb Perspect Biol* 4, a006783 (2012).
2. Backer, R. A. et al. A central role for Notch in effector CD8(+) T cell differentiation. *Nat Immunol* 15, 1143-51 (2014).
3. Best, J. A. et al. Transcriptional insights into the CD8(+) T cell response to infection and memory T cell formation. *Nat Immunol* 14, 404-12 (2013).
4. Pearce, E. L. et al. Control of effector CD8+ T cell function by the transcription factor Eomesodermin. *Science* 302, 1041-3 (2003).
5. Szabo, S. J. et al. A novel transcription factor, T-bet, directs Th1 lineage commitment. *Cell* 100, 655-69 (2000).
6. Bartel, D. P. MicroRNAs: target recognition and regulatory functions. *Cell* 136, 215-33 (2009).
7. Ha, M. & Kim, V. N. Regulation of microRNA biogenesis. *Nat Rev Mol Cell Biol* 15, 509-24 (2014).
8. Chen, C. Z., Li, L., Lodish, H. F. & Bartel, D. P. MicroRNAs modulate hematopoietic lineage differentiation. *Science* 303, 83-6 (2004).
9. Cobb, B. S. et al. A role for Dicer in immune regulation. *J Exp Med* 203, 2519-27 (2006).
10. Cobb, B. S. et al. T cell lineage choice and differentiation in the absence of the RNase III enzyme Dicer. *J Exp Med* 201, 1367-73 (2005).
11. Muljo, S. A. et al. Aberrant T cell differentiation in the absence of Dicer. *J Exp Med* 202, 261-9 (2005).
12. Henao-Mejia, J. et al. The microRNA miR-181 is a critical cellular metabolic rheostat essential for NKT cell ontogenesis and lymphocyte development and homeostasis. *Immunity* 38, 984-97 (2013).
13. Li, Q. J. et al. miR-181a is an intrinsic modulator of T cell sensitivity and selection. *Cell* 129, 147-61 (2007).
14. Ma, F. et al. The microRNA miR-29 controls innate and adaptive immune responses to intracellular bacterial infection by targeting interferon-gamma. *Nat Immunol* 12, 861-9 (2011).
15. Steiner, D. F. et al. MicroRNA-29 regulates T-box transcription factors and interferon-gamma production in helper T cells. *Immunity* 35, 169-81 (2011).
16. Zhang, N. & Bevan, M. J. Dicer controls CD8+ T-cell activation, migration, and survival. *Proc Natl Acad Sci USA* 107, 21629-34 (2010).
17. Katz, G. et al. T cell receptor stimulation impairs IL-7 receptor signaling by inducing expression of the microRNA miR-17 to target Janus kinase 1. *Sci Signal* 7, ra83 (2014).
18. Wu, T. et al. Temporal expression of microRNA cluster miR-17-92 regulates effector and memory CD8+ T-cell differentiation. *Proc Natl Acad Sci USA* 109, 9965-70 (2012).
19. Pobezinsky, L. A. et al. Let-7 microRNAs target the lineage-specific transcription factor PLZF to regulate terminal NKT cell differentiation and effector function. *NatImmunol* 16, 517-24 (2015).
20. Yuan, J., Nguyen, C. K., Liu, X., Kanellopoulou, C. & Muljo, S. A. Lin28b reprograms adult bone marrow hematopoietic progenitors to mediate fetal-like lymphopoiesis. *Science* 335, 1195-200 (2012).
21. Polikepahad, S. et al. Proinflammatory role for let-7 microRNAS in experimental asthma. *J Biol Chem* 285, 30139-49 (2010).
22. Swaminathan, S. et al. Differential regulation of the Let-7 family of microRNAs in CD4+ T cells alters IL-10 expression. *J Immunol* 188, 6238-46 (2012).
23. Okoye, I. S. et al. MicroRNA-containing T-regulatory-cell-derived exosomes suppress pathogenic T helper 1 cells. *Immunity* 41, 89-103 (2014).
24. Piskounova, E. et al. Lin28A and Lin28B inhibit let-7 microRNA biogenesis by distinct mechanisms. *Cell* 147, 1066-79 (2011).
25. Cuylen, S. et al. Ki-67 acts as a biological surfactant to disperse mitotic chromosomes. *Nature* 535, 308-12 (2016).
26. Zhu, H. et al. The Lin28/let-7 axis regulates glucose metabolism. *Cell* 147, 81-94 (2011).
27. Dominguez, C. X. et al. The transcription factors ZEB2 and T-bet cooperate to program cytotoxic T cell terminal differentiation in response to LCMV viral infection. *J Exp Med* 212, 2041-56 (2015).
28. Joshi, N. S. et al. Inflammation directs memory precursor and short-lived effector CD8(+) T cell fates via the graded expression of T-bet transcription factor. *Immunity* 27, 281-95 (2007).
29. Thimme, R. et al. Increased expression of the NK cell receptor KLRG1 by virus specific CD8 T cells during persistent antigen stimulation. *J Virol* 79, 12112-6 (2005).

30. Voehringer, D. et al. Viral infections induce abundant numbers of senescent CD8 T cells. *J Immunol* 167, 4838-43 (2001).
31. Kaech, S. M., Hemby, S., Kersh, E. & Ahmed, R. Molecular and functional profiling of memory CD8 T cell differentiation. *Cell* 111, 837-51 (2002).
32. Wherry, E. J. & Ahmed, R. Memory CD8 T-cell differentiation during viral infection. *J Virol* 78, 5535-45 (2004).
33. Williams, M. A. & Bevan, M. J. Effector and memory CTL differentiation. *Annu Rev Immunol* 25, 171-92 (2007).
34. Felix, N. J. & Allen, P. M. Specificity of T-cell alloreactivity. *Nat Rev Immunol* 7, 942-53 (2007).
35. Jankovic, V., Remus, K., Molano, A. & Nikolich-Zugich, J. T cell recognition of an engineered MHC class I molecule: implications for peptide-independent alloreactivity. *J Immunol* 169, 1887-92 (2002).
36. Johnson, C. D. et al. The let-7 microRNA represses cell proliferation pathways in human cells. *Cancer Res* 67, 7713-22 (2007).
37. Iritani, B. M. et al. Modulation of T-lymphocyte development, growth and cell size by the Myc antagonist and transcriptional repressor Mad 1. *EMBO J* 21, 4820-30 (2002).
38. Kim, H. H. et al. HuR recruits let-7/RISC to repress c-Myc expression. *Genes Dev* 23, 1743-8 (2009).
39. Nie, Z. et al. c-Myc is a universal amplifier of expressed genes in lymphocytes and embryonic stem cells. *Cell* 151, 68-79 (2012).
40. Verbist, K. C. et al. Metabolic maintenance of cell asymmetry following division in activated T lymphocytes. *Nature* 532, 389-93 (2016).
41. Chou, C. et al. c-Myc-induced transcription factor AP4 is required for host protection mediated by CD8+ T cells. *Nat Immunol* 15, 884-93 (2014).
42. Chain, C. M., Driessens, G., O'Keefe, J. P. & Gajewski, T. F. Glucose deprivation inhibits multiple key gene expression events and effector functions in CD8+ T cells. *Eur J Immunol* 38, 2438-50 (2008).
43. Wang, R. et al. The transcription factor Myc controls metabolic reprogramming upon T lymphocyte activation. *Immunity* 35, 871-82 (2011).
44. Hayes, M. P., Berrebi, G. A. & Henkart, P. A. Induction of target cell DNA release by the cytotoxic T lymphocyte granule protease granzyme A. *J Exp Med* 170, 933-46 (1989).
45. Lancki, D. W., Hsieh, C. S. & Fitch, F. W. Mechanisms of lysis by cytotoxic T lymphocyte clones. Lytic activity and gene expression in cloned antigen-specific CD4+ and CD8+ T lymphocytes. *J Immunol* 146, 3242-9 (1991).
46. Lai, E. C. Micro RNAs are complementary to 3' UTR sequence motifs that mediate negative post-transcriptional regulation. *Nat Genet* 30, 363-4 (2002).
47. Reinhart, B. J. et al. The 21-nucleotide let-7 RNA regulates developmental timing in *Caenorhabditis elegans*. *Nature* 403, 901-6 (2000).
48. Wightman, B., Ha, I. & Ruvkun, G. Posttranscriptional regulation of the heterochronic gene lin-14 by lin-4 mediates temporal pattern formation in *C. elegans*. *Cell* 75, 855-62 (1993).
49. Cho, O. H. et al. Notch regulates cytolytic effector function in CD8+ T cells. *J Immunol* 182, 3380-9 (2009).
50. Kallies, A., Xin, A., Belz, G. T. & Nutt, S. L. Blimp-1 transcription factor is required for the differentiation of effector CD8(+) T cells and memory responses. *Immunity* 31, 283-95 (2009).
51. Rutishauser, R. L. et al. Transcriptional repressor Blimp-1 promotes CD8(+) T cell terminal differentiation and represses the acquisition of central memory T cell properties. *Immunity* 31, 296-308 (2009).
52. Szabo, S. J. et al. Distinct effects of T-bet in TH1 lineage commitment and IFNgamma production in CD4 and CD8 T cells. *Science* 295, 338-42 (2002).
53. Abbott, A. L. et al. The let-7 MicroRNA family members mir-48, mir-84, and mir-241 function together to regulate developmental timing in *Caenorhabditis elegans*. *Dev Cell* 9, 403-14 (2005).
54. Bussing, I., Slack, F. J. & Grosshans, H. let-7 microRNAs in development, stem cells and cancer. *Trends Mol Med* 14, 400-9 (2008).
55. Roush, S. & Slack, F. J. The let-7 family of microRNAs. *Trends Cell Biol* 18, 505-16 (2008).
56. Yu, F. et al. let-7 regulates self-renewal and tumorigenicity of breast cancer cells. *Cell* 131, 1109-23 (2007).
57. Goldrath, A. W. et al. Cytokine requirements for acute and Basal homeostatic proliferation of naïve and memory CD8+ T cells. *J Exp Med* 195, 1515-22 (2002).
58. Kamimura, D. & Bevan, M. J. Naïve CD8+ T cells differentiate into protective memory-like cells after IL-2 anti-IL-2 complex treatment in vivo. *J Exp Med* 204, 1803-12 (2007).
59. Kieper, W. C., Burghardt, J. T. & Surh, C. D. A role for TCR affinity in regulating naïve T cell homeostasis. *J Immunol* 172, 40-4 (2004).
60. Kieper, W. C. et al. Overexpression of interleukin (IL)-7 leads to IL-15-independent generation of memory phenotype CD8+ T cells. *J Exp Med* 195, 1533-9 (2002).
61. Kimura, M. Y. et al. IL-7 signaling must be intermittent, not continuous, during CD8(+) T cell homeostasis to promote cell survival instead of cell death. *Nat Immunol* 14, 143-51 (2013).
62. Intlekofer, A. M. et al. Effector and memory CD8+ T cell fate coupled by T-bet and eomesodermin. *Nat Immunol* 6, 1236-44 (2005).
63. Weinreich, M. A., Odumade, O. A., Jameson, S. C. & Hogquist, K. A. T cells expressing the transcription factor PLZF regulate the development of memorylike CD8+ T cells. *Nat Immunol* 11, 709-16 (2010).
64. Frauwirth, K. A. et al. The CD28 signaling pathway regulates glucose metabolism. *Immunity* 16, 769-77 (2002).
65. Frauwirth, K. A. & Thompson, C. B. Regulation of T lymphocyte metabolism. *J Immunol* 172, 4661-5 (2004).
66. Grumont, R. et al. The mitogen-induced increase in T cell size involves PKC and NFAT activation of Rel/NF-kappaB-dependent c-myc expression. *Immunity* 21, 19-30 (2004).
67. Askew, D. S., Ihle, J. N. & Cleveland, J. L. Activation of apoptosis associated with enforced myc expression in myeloid progenitor cells is dominant to the suppression of apoptosis by interleukin-3 or erythropoietin. *Blood* 82, 2079-87 (1993).
68. Evan, G. I. et al. Induction of apoptosis in fibroblasts by c-myc protein. *Cell* 69, 119-28 (1992).
69. Fanidi, A., Harrington, E. A. & Evan, G. I. Cooperative interaction between c-myc and bcl-2 proto-oncogenes. *Nature* 359, 554-6 (1992).
70. Sampson, V. B. et al. MicroRNA let-7a down-regulates MYC and reverts MYC induced growth in Burkitt lymphoma cells. *Cancer Res* 67, 9762-70 (2007).
71. Bouchard, C. et al. Direct induction of cyclin D2 by Myc contributes to cell cycle progression and sequestration of p27. *EMBO J* 18, 5321-33 (1999).

72. Galaktionov, K., Chen, X. & Beach, D. Cdc25 cell-cycle phosphatase as a target of c-myc. *Nature* 382, 511-7 (1996).
73. Mateyak, M. K., Obaya, A. J. & Sedivy, J. M. c-Myc regulates cyclin D-Cdk4 and—Cdk6 activity but affects cell cycle progression at multiple independent points. *Mol Cell Biol* 19, 4672-83 (1999).
74. Chang, J. T., Wherry, E. J. & Goldrath, A. W. Molecular regulation of effector and memory T cell differentiation. *Nat Immunol* 15, 1104-15 (2014).
75. Nayar, R. et al. TCR signaling via Tec kinase ITK and interferon regulatory factor 4 (IRF4) regulates CD8+ T-cell differentiation. *Proc Natl Acad Sci USA* 109, E2794-802 (2012).
76. Markstein, M., Markstein, P., Markstein, V. & Levine, M. S. Genome-wide analysis of clustered Dorsal binding sites identifies putative target genes in the *Drosophila* embryo. *Proc Natl Acad Sci USA* 99, 763-8 (2002).
77. Probst, H. C. et al. Immunodominance of an antiviral cytotoxic T cell response is shaped by the kinetics of viral protein expression. *J Immunol* 171, 5415-22 (2003).

All publications, patents, and patent applications mentioned in this specification are herein incorporated by reference to the same extent as if each individual publication, patent, or patent application was specifically and individually indicated to be incorporated by reference. In the event that the definition of a term incorporated by reference conflicts with a term defined herein, this specification shall control.

What is claimed is:

1. A method to treat cancer comprising administering to a subject in need thereof an effective amount of a composition comprising T cells wherein the T cells have decreased expression of let7 as compared to wild-type T cells, wherein the let7 expression is decreased by RNAi, shRNA, microRNA, knock out, LIN28 inhibitory protein or mutation of let7.

2. The method of claim 1, further comprising administering at least one or more additional cancer treatments.

3. The method of claim 2, where the one or more additional treatments comprise chemotherapy, radiation, immunotherapy, and/or suppression immunotherapy.

4. A method to treat infectious disease comprising administering to a subject in need thereof an effective amount of a composition comprising T cells wherein the T cells have decreased expression of let7 as compared to wild-type T cells, wherein the let7 expression is decreased by RNAi, shRNA, microRNA, knock out, LIN28 inhibitory protein or mutation of let7.

5. The method of claim 4, further comprising administering at least one or more additional infectious disease treatments.

6. The method of claim 5, where the one or more additional treatments comprise antibiotic, antiviral, antifungal, antiprotozoal, and/or anthelminthic treatments.

7. A method to increase cytotoxic activity of cytotoxic T lymphocytes (CTLs) comprising decreasing the level of let7 expression in said CTLs, wherein the let7 expression is decreased by RNAi, shRNA, microRNA, knock out, LIN28 inhibitory protein or mutation of let7.

* * * * *

SEQUENCE LISTING

```
<160> NUMBER OF SEQ ID NOS: 55

<210> SEQ ID NO 1
<211> LENGTH: 22
<212> TYPE: RNA
<213> ORGANISM: Homo sapiens

<400> SEQUENCE: 1
ugagguagua gguuguauag uu                                                22

<210> SEQ ID NO 2
<211> LENGTH: 22
<212> TYPE: RNA
<213> ORGANISM: Homo sapiens

<400> SEQUENCE: 2
ugagguagua gguugugugg uu                                                22

<210> SEQ ID NO 3
<211> LENGTH: 22
<212> TYPE: RNA
<213> ORGANISM: Homo sapiens

<400> SEQUENCE: 3
ugagguagua gguuguaugg uu                                                22

<210> SEQ ID NO 4
<211> LENGTH: 22
<212> TYPE: RNA
<213> ORGANISM: Homo sapiens

<400> SEQUENCE: 4
agagguagua gguugcauag uu                                                22

<210> SEQ ID NO 5
<211> LENGTH: 22
<212> TYPE: RNA
<213> ORGANISM: Homo sapiens

<400> SEQUENCE: 5
ugagguagga gguuguauag uu                                                22

<210> SEQ ID NO 6
<211> LENGTH: 22
<212> TYPE: RNA
<213> ORGANISM: Homo sapiens

<400> SEQUENCE: 6
```

```
ugagguagua gauuguauag uu                                           22

<210> SEQ ID NO 7
<211> LENGTH: 22
<212> TYPE: RNA
<213> ORGANISM: Homo sapiens

<400> SEQUENCE: 7
ugagguagua guuuguacag uu                                           22

<210> SEQ ID NO 8
<211> LENGTH: 22
<212> TYPE: RNA
<213> ORGANISM: Homo sapiens

<400> SEQUENCE: 8
ugagguagua guuugugcug uu                                           22

<210> SEQ ID NO 9
<211> LENGTH: 22
<212> TYPE: RNA
<213> ORGANISM: Homo sapiens

<400> SEQUENCE: 9
ugagguagua aguuguauug uu                                           22

<210> SEQ ID NO 10
<211> LENGTH: 22
<212> TYPE: RNA
<213> ORGANISM: Mus musculus

<400> SEQUENCE: 10
ugagguagua gguuguauag uu                                           22

<210> SEQ ID NO 11
<211> LENGTH: 22
<212> TYPE: RNA
<213> ORGANISM: Mus musculus

<400> SEQUENCE: 11
ugagguagua gguugugugg uu                                           22

<210> SEQ ID NO 12
<211> LENGTH: 22
<212> TYPE: RNA
<213> ORGANISM: Mus musculus

<400> SEQUENCE: 12
ugagguagua gguuguaugg uu                                           22

<210> SEQ ID NO 13
<211> LENGTH: 22
<212> TYPE: RNA
<213> ORGANISM: Mus musculus

<400> SEQUENCE: 13
agagguagua gguugcauag uu                                           22

<210> SEQ ID NO 14
<211> LENGTH: 22
<212> TYPE: RNA
<213> ORGANISM: Mus musculus

<400> SEQUENCE: 14
```

-continued ugagguagga gguuguauag uu					22

<210> SEQ ID NO 15
<211> LENGTH: 22
<212> TYPE: RNA
<213> ORGANISM: Mus musculus

<400> SEQUENCE: 15
ugagguagua gauuguauag uu					22

<210> SEQ ID NO 16
<211> LENGTH: 22
<212> TYPE: RNA
<213> ORGANISM: Mus musculus

<400> SEQUENCE: 16
ugagguagua guuuguacag uu					22

<210> SEQ ID NO 17
<211> LENGTH: 22
<212> TYPE: RNA
<213> ORGANISM: Mus musculus

<400> SEQUENCE: 17
ugagguagua guuugugcug uu					22

<210> SEQ ID NO 18
<211> LENGTH: 22
<212> TYPE: RNA
<213> ORGANISM: Mus musculus

<400> SEQUENCE: 18
ugagguagua aguuguauug uu					22

<210> SEQ ID NO 19
<211> LENGTH: 22
<212> TYPE: DNA
<213> ORGANISM: Artificial Sequence
<220> FEATURE:
<223> OTHER INFORMATION: A synthetic primer

<400> SEQUENCE: 19
acagcagtct acagagaatg gg					22

<210> SEQ ID NO 20
<211> LENGTH: 21
<212> TYPE: DNA
<213> ORGANISM: Artificial Sequence
<220> FEATURE:
<223> OTHER INFORMATION: A synthetic primer

<400> SEQUENCE: 20
gagtgggaac tggtagtgtt g					21

<210> SEQ ID NO 21
<211> LENGTH: 21
<212> TYPE: DNA
<213> ORGANISM: Artificial Sequence
<220> FEATURE:
<223> OTHER INFORMATION: A synthetic primer

<400> SEQUENCE: 21
gtaggcgata ggtcatacgg a					21

<210> SEQ ID NO 22
<211> LENGTH: 21
<212> TYPE: DNA
<213> ORGANISM: Artificial Sequence
<220> FEATURE:
<223> OTHER INFORMATION: A synthetic primer

<400> SEQUENCE: 22
ggcgtaccca cagaaaccat a                                              21

<210> SEQ ID NO 23
<211> LENGTH: 22
<212> TYPE: DNA
<213> ORGANISM: Artificial Sequence
<220> FEATURE:
<223> OTHER INFORMATION: A synthetic primer

<400> SEQUENCE: 23
cagttcggct ataacactgg tg                                             22

<210> SEQ ID NO 24
<211> LENGTH: 20
<212> TYPE: DNA
<213> ORGANISM: Artificial Sequence
<220> FEATURE:
<223> OTHER INFORMATION: A synthetic primer

<400> SEQUENCE: 24
atggggacaa cgaaggtgac                                                20

<210> SEQ ID NO 25
<211> LENGTH: 22
<212> TYPE: DNA
<213> ORGANISM: Artificial Sequence
<220> FEATURE:
<223> OTHER INFORMATION: A synthetic primer

<400> SEQUENCE: 25 gaagggggact attcttgtgg gt                                            22

<210> SEQ ID NO 26
<211> LENGTH: 20
<212> TYPE: DNA
<213> ORGANISM: Artificial Sequence
<220> FEATURE:
<223> OTHER INFORMATION: A synthetic primer

<400> SEQUENCE: 26
ggaggcgaga acatcaagcc                                                20

<210> SEQ ID NO 27
<211> LENGTH: 21
<212> TYPE: DNA
<213> ORGANISM: Artificial Sequence
<220> FEATURE:
<223> OTHER INFORMATION: A synthetic primer

<400> SEQUENCE: 27
tgatcgcctg cttattcacg g                                              21

<210> SEQ ID NO 28
<211> LENGTH: 21
<212> TYPE: DNA
<213> ORGANISM: Artificial Sequence
<220> FEATURE:
<223> OTHER INFORMATION: A synthetic primer

```
<400> SEQUENCE: 28
ccaggaagtt cttcgttggg g                                              21

<210> SEQ ID NO 29
<211> LENGTH: 19
<212> TYPE: DNA
<213> ORGANISM: Artificial Sequence
<220> FEATURE:
<223> OTHER INFORMATION: A synthetic primer

<400> SEQUENCE: 29
gccgcctgga cattgactc                                                 19

<210> SEQ ID NO 30
<211> LENGTH: 20
<212> TYPE: DNA
<213> ORGANISM: Artificial Sequence
<220> FEATURE:
<223> OTHER INFORMATION: A synthetic primer

<400> SEQUENCE: 30
agtgctgcat gaggagacac                                                20

<210> SEQ ID NO 31
<211> LENGTH: 20
<212> TYPE: DNA
<213> ORGANISM: Artificial Sequence
<220> FEATURE:
<223> OTHER INFORMATION: A synthetic primer

<400> SEQUENCE: 31
ggagaagcta gagcgggaac                                                20

<210> SEQ ID NO 32
<211> LENGTH: 21
<212> TYPE: DNA
<213> ORGANISM: Artificial Sequence
<220> FEATURE:
<223> OTHER INFORMATION: A synthetic primer

<400> SEQUENCE: 32
cccactccag gatcttttcc c                                              21

<210> SEQ ID NO 33
<211> LENGTH: 20
<212> TYPE: DNA
<213> ORGANISM: Artificial Sequence
<220> FEATURE:
<223> OTHER INFORMATION: A synthetic primer

<400> SEQUENCE: 33
gacgggggta cttctgttca                                                20

<210> SEQ ID NO 34
<211> LENGTH: 20
<212> TYPE: DNA
<213> ORGANISM: Artificial Sequence
<220> FEATURE:
<223> OTHER INFORMATION: A synthetic primer

<400> SEQUENCE: 34
gcgacatgcc ttccaacagc                                                20

<210> SEQ ID NO 35
```

<210> SEQ ID NO 35
<211> LENGTH: 20
<212> TYPE: DNA
<213> ORGANISM: Artificial Sequence
<220> FEATURE:
<223> OTHER INFORMATION: A synthetic primer

<400> SEQUENCE: 35
cgaggcatgc tgccccacaa                                                       20

<210> SEQ ID NO 36
<211> LENGTH: 22
<212> TYPE: DNA
<213> ORGANISM: Artificial Sequence
<220> FEATURE:
<223> OTHER INFORMATION: A synthetic primer

<400> SEQUENCE: 36
gatgaggtga aggtgtctt gg                                                     22

<210> SEQ ID NO 37
<211> LENGTH: 19
<212> TYPE: DNA
<213> ORGANISM: Artificial Sequence
<220> FEATURE:
<223> OTHER INFORMATION: A synthetic primer

<400> SEQUENCE: 37
cgcacagagc gatgaaggt                                                        19

<210> SEQ ID NO 38
<211> LENGTH: 21
<212> TYPE: DNA
<213> ORGANISM: Artificial Sequence
<220> FEATURE:
<223> OTHER INFORMATION: A synthetic primer

<400> SEQUENCE: 38
acaatggatc actaccccgt g                                                     21

<210> SEQ ID NO 39
<211> LENGTH: 22
<212> TYPE: DNA
<213> ORGANISM: Artificial Sequence
<220> FEATURE:
<223> OTHER INFORMATION: A synthetic primer

<400> SEQUENCE: 39
aggtaagggc catctgaaaa ct                                                    22

<210> SEQ ID NO 40
<211> LENGTH: 19
<212> TYPE: DNA
<213> ORGANISM: Artificial Sequence
<220> FEATURE:
<223> OTHER INFORMATION: A synthetic primer

<400> SEQUENCE: 40
gcccccgaca gagaagatg                                                        19

<210> SEQ ID NO 41
<211> LENGTH: 22
<212> TYPE: DNA
<213> ORGANISM: Artificial Sequence
<220> FEATURE:
<223> OTHER INFORMATION: A synthetic primer

<400> SEQUENCE: 41

-continued gtctcaggtg cattgatgac tc                                              22

<210> SEQ ID NO 42
<211> LENGTH: 21
<212> TYPE: DNA
<213> ORGANISM: Artificial Sequence
<220> FEATURE:
<223> OTHER INFORMATION: A synthetic primer

<400> SEQUENCE: 42
ggatgtcaaa ttcgggtgtg t                                               21

<210> SEQ ID NO 43
<211> LENGTH: 19
<212> TYPE: DNA
<213> ORGANISM: Artificial Sequence
<220> FEATURE:
<223> OTHER INFORMATION: A synthetic primer

<400> SEQUENCE: 43
cggccttccc tcgtagtga                                                  19

<210> SEQ ID NO 44
<211> LENGTH: 21
<212> TYPE: DNA
<213> ORGANISM: Artificial Sequence
<220> FEATURE:
<223> OTHER INFORMATION: A synthetic primer

<400> SEQUENCE: 44
aaccgcctag aaatctccag a                                               21

<210> SEQ ID NO 45
<211> LENGTH: 21
<212> TYPE: DNA
<213> ORGANISM: Artificial Sequence
<220> FEATURE:
<223> OTHER INFORMATION: A synthetic primer

<400> SEQUENCE: 45
caaagtcgat gtaagcggtg g                                               21

<210> SEQ ID NO 46
<211> LENGTH: 22
<212> TYPE: DNA
<213> ORGANISM: Artificial Sequence
<220> FEATURE:
<223> OTHER INFORMATION: A synthetic primer

<400> SEQUENCE: 46
ccatgagaga aattcagccg ag                                              22

<210> SEQ ID NO 47
<211> LENGTH: 20
<212> TYPE: DNA
<213> ORGANISM: Artificial Sequence
<220> FEATURE:
<223> OTHER INFORMATION: A synthetic primer

<400> SEQUENCE: 47
ggtttgcctc ttctccacag                                                 20

<210> SEQ ID NO 48
<211> LENGTH: 20
<212> TYPE: DNA

```
<213> ORGANISM: Artificial Sequence
<220> FEATURE:
<223> OTHER INFORMATION: A synthetic primer

<400> SEQUENCE: 48
ttttgccggg atgtagagac                                                   20

<210> SEQ ID NO 49
<211> LENGTH: 20
<212> TYPE: DNA
<213> ORGANISM: Artificial Sequence
<220> FEATURE:
<223> OTHER INFORMATION: A synthetic primer

<400> SEQUENCE: 49
tgactcacac aggttgccag                                                   20

<210> SEQ ID NO 50
<211> LENGTH: 20
<212> TYPE: DNA
<213> ORGANISM: Artificial Sequence
<220> FEATURE:
<223> OTHER INFORMATION: A synthetic primer

<400> SEQUENCE: 50
ggcattcttg ggaactgtgt                                                   20

<210> SEQ ID NO 51
<211> LENGTH: 22
<212> TYPE: DNA
<213> ORGANISM: Artificial Sequence
<220> FEATURE:
<223> OTHER INFORMATION: A synthetic primer

<400> SEQUENCE: 51
cttagcgcgc cgctgttctc gc                                                22

<210> SEQ ID NO 52
<211> LENGTH: 20
<212> TYPE: DNA
<213> ORGANISM: Artificial Sequence
<220> FEATURE:
<223> OTHER INFORMATION: A synthetic primer

<400> SEQUENCE: 52
agcagggacc accatccgct                                                   20

<210> SEQ ID NO 53
<211> LENGTH: 14
<212> TYPE: DNA
<213> ORGANISM: Homo sapiens

<400> SEQUENCE: 53
cgctactacc tccc                                                         14

<210> SEQ ID NO 54
<211> LENGTH: 14
<212> TYPE: DNA
<213> ORGANISM: Mus musculus

<400> SEQUENCE: 54
cggtactacc tcca                                                         14

<210> SEQ ID NO 55
<211> LENGTH: 13
```

```
<212> TYPE: DNA
<213> ORGANISM: Artificial Sequence
<220> FEATURE:
<223> OTHER INFORMATION: A synthetic primer

<400> SEQUENCE: 55
cgcttaacct ccc                                                      13
```